United States Patent
Skolc et al.

(10) Patent No.: US 9,975,873 B2
(45) Date of Patent: May 22, 2018

(54) ISOINDOLINE DERIVATIVES

(71) Applicant: UCB Biopharma SPRL, Brussels (BE)

(72) Inventors: David Skolc, Brussels (BE); Ali Ates, Brussels (BE); Eric Jnoff, Brussels (BE); Anne Valade, Brussels (BE); Benoit Mathieu, Brussels (BE); Zara Sands, Brussels (BE)

(73) Assignee: UCB BIOPHARMA SPRL, Brussels (BE)

( * ) Notice: Subject to any disclaimer, the term of this patent is extended or adjusted under 35 U.S.C. 154(b) by 0 days. days.

(21) Appl. No.: 15/517,769

(22) PCT Filed: Oct. 6, 2015

(86) PCT No.: PCT/EP2015/073057
§ 371 (c)(1),
(2) Date: Apr. 7, 2017

(87) PCT Pub. No.: WO2016/055482
PCT Pub. Date: Apr. 14, 2016

(65) Prior Publication Data
US 2017/0313677 A1  Nov. 2, 2017

(30) Foreign Application Priority Data
Oct. 8, 2014 (EP) ..................... 14188150

(51) Int. Cl.
C07D 401/06 (2006.01)
A61K 31/4035 (2006.01)
C07D 209/44 (2006.01)
C07D 487/04 (2006.01)

(52) U.S. Cl.
CPC ......... C07D 401/06 (2013.01); C07D 209/44 (2013.01); C07D 487/04 (2013.01); *A61K 31/4035* (2013.01)

(58) Field of Classification Search
CPC ..................... C07D 401/06; A61K 31/4035
See application file for complete search history.

*Primary Examiner* — Golam M Shameem
(74) *Attorney, Agent, or Firm* — McDonnell Boehnen Hulbert & Berghoff LLP

(57) ABSTRACT

The present invention relates to isoindoline derivatives according to formula (I), which are Positive Allosteric Modulators of D1 and accordingly of benefit as pharmaceutical agents for the treatment of diseases in which D1 receptors play a role.

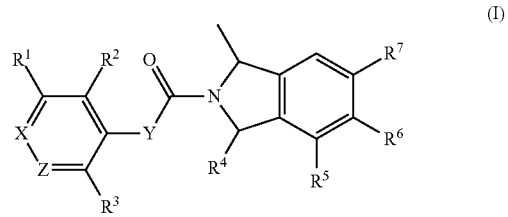

(I)

20 Claims, No Drawings

ISOINDOLINE DERIVATIVES

This application is the US national phase under 35 U.S.C. § 371 of international application PCT/EP2015/073057, filed Oct. 6, 2015, which claims priority to European application EP 14188150.8, filed Oct. 8, 2014.

FIELD OF THE INVENTION

The invention relates to isoindoline derivatives and their use in therapy. In particular the present invention relates to pharmacologically active substituted isoindoline derivatives and analogs thereof. More particularly, the present invention relates to substituted 1,3-dihydroisoindolin-2(1H)-yl derivatives and analogs thereof.

The compounds according to the present invention are D1 Positive Allosteric Modulators and accordingly of benefit as pharmaceutical agents for the treatment of diseases in which D1 receptors play a role.

BACKGROUND OF THE INVENTION

The monoamine dopamine acts via two families of GPCRs to modulate motor function, reward mechanisms, cognitive processes and other physiological functions. Specifically, dopamine acts upon neurons via D1-like, comprising dopamine D1 and D5, receptors which couple mainly to the $G_s$ G-protein and thereby stimulate cAMP production, and D2-like, which comprise D2, D3 and D4, receptors which couple to $G_{i/q}$ G-proteins and which attenuate cAMP production. These receptors are widely expressed in different brain regions. In particular, D1 receptors are involved in numerous physiological functions and behavioural processes. D1 receptors are, for instance, involved in synaptic plasticity, cognitive function and goal-directed motor functions, but also in reward processes. Due to their role in several physiological/neurological processes, D1 receptors have been implicated in a variety of disorders including cognitive and negative symptoms in schizophrenia, cognitive impairment related to classical antipsychotic therapy, impulsivity, attention disorder with hyperactivity (ADHD), Parkinson's disease and related movement disorders, Huntington's disease, dementia with Lewy Body, Alzheimer's disease, age-related cognitive decline, mild cognitive impairment (MCI), drug addiction, sleep disorders and apathy.

It has proven difficult to develop orally-bioavailable small molecules targeting D1 receptors. D1 agonists developed so far are characterized by a catechol moiety and their clinical use has therefore been limited to invasive therapies. Achieving sufficient selectivity has also been challenging due to the high degree of homology in the ligand binding site between dopamine receptors subtypes (e.g. dopamine D1 and D5). Also, D1 agonists are associated with potentially limiting adverse events including dyskinesia and hypotension. In addition, the use of D1 receptor agonists has been associated with the development of tolerance in animal models.

There is therefore a need to design new agents that do not contain a catechol moiety and that could modulate D1 receptors at a novel site to improve selectivity and reduce some side effects. There has been much interest in the identification of allosteric modulators of GPCRs, both as tools to understand receptor mechanisms and as potential therapeutic agents. GPCRs represent the largest family of cell-surface receptors and a large number of marketed drugs directly activate or block signaling pathways mediated by these receptors. However, for some GPCRs (e.g. peptide receptors), it has been proven challenging to develop small molecules or to achieve sufficient selectivity due to the high degree of homology in the ligand binding site between subtypes (e.g. dopamine D1 and D5 or D2 and D3). Accordingly, much drug research has shifted to the identification of small molecules which target sites distinct from the orthosteric natural agonist. Ligands which bind to these sites induce a conformational change in the GPCR thereby allosterically modulating the receptor function. Allosteric ligands have a diverse range of activities including the ability to potentiate (positive allosteric modulator, PAM) or attenuate (negative allosteric modulator, NAM) the effects of the endogenous ligand, by affecting affinity and/or efficacy. As well as subtype selectivity, allosteric modulators can present other potential advantages from a drug discovery perspective such as a lack of direct effect or intrinsic efficacy; only potentiating the effect of the native transmitter where and when it is released; reduced propensity for inducing desensitization arising from constant exposure to an agonist as well as reduced propensity to induce target-related side-effects.

SUMMARY OF THE INVENTION

The compounds according to the present invention potentiate the effect of D1 agonists, or the endogenous ligand on D1 receptors, i.e. dopamine, through an allosteric mechanism, and are therefore D1 positive allosteric modulators (D1 PAM).

The compounds in accordance with the present invention, being D1 PAM, are therefore beneficial in the treatment and/or prevention of diseases in which D1 plays a role. Such diseases include cognitive and negative symptoms in schizophrenia, cognitive impairment related to classical antipsychotic therapy, impulsivity, attention disorder with hyperactivity (ADHD), Parkinson's disease and related movement disorders, Huntington's disease, dementia with Lewy Body, Alzheimer's disease, age-related cognitive decline, mild cognitive impairment (MCI), drug addiction, sleep disorders and apathy.

The present invention provides, in particular, isoindoline derivatives and analogs thereof which are beneficial for the treatment and/or prevention of diseases in which D1 receptors play a role.

DETAILED DESCRIPTION OF THE INVENTION

The present invention provides a compound of formula (I), or a pharmaceutically acceptable salt thereof,

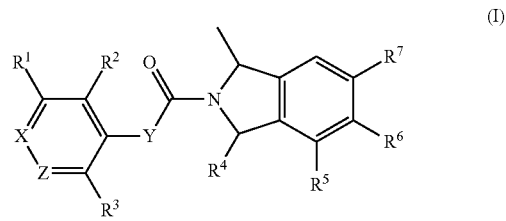

wherein $R^1$ is hydrogen, halogen, cyano or hydroxy; $C_{1-6}$ alkyl, $C_{1-6}$ alkoxy, $C_{1-6}$ alkylsulfanyl, $C_{1-6}$ alkylsulfinyl, $C_{1-6}$ alkylsulfonyl, ($C_{1-6}$-alkylsulfonyl)amino or ($C_{1-6}$-alkylsulfonyl)amino($C_{1-6}$alkyl), any of which groups may be substituted by one or more substituents;

$R^2$ is hydrogen, cyano, halogen; or $C_{1-6}$ alkyl, $C_{1-6}$ alkoxy, $C_{1-6}$ alkylsulfanyl, $C_{1-6}$ alkylsulfinyl, $C_{1-6}$ alkylsulfonyl, $C_{1-6}$ alkylsulfonylamino, ($C_{1-6}$ alkylsulfonyl)amino($C_{1-6}$ alkyl), $C_{1-6}$ alkylamido, ($C_{1-6}$ alkylacyl)amino, ($C_{1-6}$ alkylacyl)amino($C_{1-6}$ alkyl), or heteroaryl, any of which groups may be substituted by one or more substituents; or $R^1$ and $R^2$ are linked together to form with the adjacent aromatic group a bicycle of formula (i):

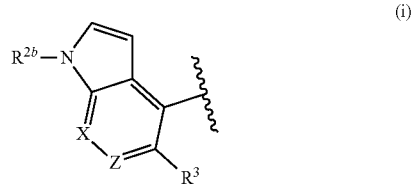

wherein $R^{2b}$ is hydrogen or $C_{1-6}$ alkylsulfonyl;
$R^3$ is halogen, $C_{1-6}$ alkyl, $C_{1-6}$ alkoxy or cyano;
$R^4$ is hydrogen, halogen, $C_{1-6}$ alkyl, hydroxy, $C_{1-6}$ alkoxy, $C_{1-6}$ alkylsulfonyl, $C_{1-6}$ alkoxycarbonyloxy or $C_{1-6}$ alkylaminocarbonyloxy;
$R^5$ is hydrogen, cyano, hydroxy or nitro; or $C_{1-6}$ alkyl; or $C_{1-6}$ alkoxy, $C_{1-6}$-alkylsulfonyl, $C_{1-6}$-alkylsulfonylamino; $C_{1-6}$-alkylsulfonylamino($C_{1-6}$ alkyl), heterocycle, $C_{1-6}$ alkylacylamino, $C_{1-6}$ alkylacylamino($C_{1-6}$ alkyl); $C_{1-6}$ alkylureido($C_{1-6}$ alkyl); $C_{1-6}$alkylcarbamate($C_{1-6}$ alkyl); amido; $C_{1-6}$alkoxycarbonyl, $C_{1-6}$alkoxycarbonyloxy($C_{1-6}$alkyl); amino group; N-cyano-S—($C_{1-6}$-alkyl)sulfonimidoyl, N,S-(di-$C_{1-6}$-alkyl)sulfonimidoyl, aminosulfinyl; $C_{1-6}$-alkylsulfinyl; aminosulfonyl; (di-$C_{1-6}$-alkyl)(oxido)-$\lambda^6$-sulfanylidene-amino; amino($C_{1-6}$ alkyl), amido($C_{1-6}$ alkyl) or amido($C_{1-6}$ alkoxy); any of which groups may be optionally substituted by one or more substituents;
$R^6$ is hydrogen or cyano;
$R^7$ is either hydrogen or ($C_{1-6}$-alkylsulfonyl)amino;
X is either $CR^9$ or N; wherein $R^9$ is hydrogen, halogen or $C_{1-6}$-alkyl substituted by hydroxyl;
Z is CH or N; and
Y is $CH_2$ or NH.

The present invention also provides a compound of formula (I) as defined above or a pharmaceutically acceptable salt thereof, for use in therapy.

In another aspect, the present invention also provides a compound of formula (I) as defined above, or a pharmaceutically acceptable salt thereof, for use in the treatment and/or prevention of diseases and disorders in which D1 receptors play a role.

In another aspect, the present invention provides a compound of formula (I) as defined above, or a pharmaceutically acceptable salt thereof for use in the treatment and/or prevention of cognitive and negative symptoms in schizophrenia, cognitive impairment related to classical antipsychotic therapy, impulsivity, attention disorder with hyperactivity (ADHD), Parkinson's disease and related movement disorders, Huntington's disease, dementia with Lewy Body, Alzheimer's disease, age-related cognitive decline, mild cognitive impairment (MCI), drug addiction, sleep disorders and apathy.

In a particular aspect, the present invention provides a compound of formula (I) as defined above, or a pharmaceutically acceptable salt thereof for use in the treatment and/or prevention of Parkinson's disease.

In a further aspect, the present invention provides for the use of a compound of formula (I) as defined above, or a pharmaceutically acceptable salt thereof, for the manufacture of a medicament useful for the treatment and/or prevention of diseases and disorders in which D1 receptors play a role.

In another further aspect, the present invention provides for the use of a compound of formula (I) as defined above, or a pharmaceutically acceptable salt thereof, for the manufacture of a medicament useful for the treatment and/or prevention of cognitive and negative symptoms in schizophrenia, cognitive impairment related to classical antipsychotic therapy, impulsivity, attention disorder with hyperactivity (ADHD), Parkinson's disease and related movement disorders, Huntington's disease, dementia with Lewy Body, Alzheimer's disease, age-related cognitive decline, mild cognitive impairment (MCI), drug addiction, sleep disorders and apathy.

In a particular aspect, the present invention provides for the use of a compound of formula (I) as defined above, or a pharmaceutically acceptable salt thereof, for the manufacture of a medicament useful for the treatment and/or prevention of Parkinson's disease, The present invention also provides a method for the treatment and/or prevention of diseases and disorders for which the administration of D1 positive allosteric modulator is indicated, which comprises administering to a patient in need of such treatment an effective amount of a compound of formula (I) as defined above, or a pharmaceutically acceptable salt thereof.

In another aspect, the present invention provides a method for the treatment and/or prevention of cognitive and negative symptoms in schizophrenia, cognitive impairment related to classical antipsychotic therapy, impulsivity, attention disorder with hyperactivity (ADHD), Parkinson's disease and related movement disorders, Huntington's disease, dementia with Lewy Body, Alzheimer's disease, age-related cognitive decline, mild cognitive impairment (MCI), drug addiction, sleep disorders and apathy, which comprises administering to a patient in need of such treatment an effective amount of a compound of formula (I) as defined above, or a pharmaceutically acceptable salt thereof.

In a particular aspect, the present invention provides a method for the treatment and/or prevention of Parkinson's Disease, which comprises administering to a patient in need of such treatment an effective amount of a compound of formula (I) as defined above, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one, two or three substituents. Examples of substituents include "$C_{1-6}$ alkyl", "$C_{3-8}$ cycloalkyl", "amino", "acyl", "acyloxy", "acylamino", "amido", "alkoxycarbonyl", "ureido", "carbamate", "aryl", "heterocycle", "heteroaryl", "heterocycloalkyl", "sulfanyl", "sulfinyl", "sulfonyl", "alkoxy", "sulfanyl", "sulphoximines", "halogen", trihalomethyl, cyano, hydroxy and the like. Suitable substitutents for each particular groups of compounds formula (I) are further described herein after in the present specification.

The present invention includes within its scope salts of the compounds of formula (I) above. For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in Handbook of Pharmaceutical Salts: Properties, Selection and Use, ed. P. H. Stahl & C. G. Wermuth, Wiley-VCH, 2002.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see Pharmaceutical Salts and Co-crystals, ed. J. Wouters & L. Quere, RSC Publishing, 2012).

The term "hydrogen", as used herein encompasses all isotopic forms of hydrogen atom. Therefore each individual hydrogen atom present in formula (I), or in the formulae depicted hereinafter, may be present as a $^1H$, $^2H$ (deuterium) or $^3H$ (tritium) atom, preferably $^1H$.

The term "hydroxy", as used herein, represents a group of formula —OH.

"Halogen" refers to fluoro, chloro, bromo and iodo atoms.

"Cyano" refers to —CN.

"Nitro" refers to —NO$_2$.

"$C_{1-6}$ alkyl" or "$C_{1-4}$ alkyl" refers to an alkyl group which represents saturated, monovalent hydrocarbon radicals having straight (unbranched) or branched moities or combinations thereof, and containing 1 to 6 carbon atoms, or 1 to 4 carbon atoms. Examples of $C_{1-4}$ alkyl groups are methyl, ethyl, n-propyl, isopropyl, n-butyl, isobutyl, tert-butyl. "$C_{1-4}$" or "$C_{1-6}$ alkyl" groups may be substituted by one or more substituents selected from halogen, hydroxy, cyano, amido, alkoxy, sulfonylamino. Particular alkyl groups according to the present invention include methyl, ethyl, 2,2,2-trifluoroethyl, propyl.

The term "$C_{1-6}$-alkyl hydroxy" or "(hydroxy)$C_{1-6}$-alkyl", as used herein, refers to an alkyl as defined above substituted by one or more "hydroxy". Example of $C_{1-6}$-alkyl hydroxy group according to the present invention is hydroxymethyl.

"$C_{1-6}$ alkoxy" refers to a group of formula —O—R where R is a substituted or unsubstituted "$C_{1-6}$ alkyl". Example of alkoxy groups according to the present invention is methoxy, 2-(methylamino)-2-oxoethoxy or 2-(dimethylamino)-2-oxoethoxy.

"$C_{3-8}$ cycloalkyl" refers to a saturated carbocyclic group of from 3 to 8 carbon atoms having a single ring (e.g., cyclohexyl) or multiple condensed rings (e.g., norbornyl). Cycloalkyl include cyclopropyl, cyclobutyl, cyclopentyl, cyclohexyl, and the like.

"Aryl" refers to an unsaturated aromatic carbocyclic group of from 6 to 14 carbon atoms having a single ring (e.g., phenyl) or multiple condensed rings (e.g., naphthyl). The "aryl" groups may be unsubstituted or substituted by 1 to 3 substituents independently selected from $C_{1-4}$ alkyl, $C_{1-4}$ alkoxy, halogen, cyano, amido, hydroxy or heterocycle. Aryl include phenyl and the like.

"Heterocycle" refers to a saturated or unsaturated ring system containing, in addition to carbon atoms, at least one hetero atom, such as nitrogen, oxygen and/or sulfur. "Heterocycle" includes both "heteroaryl" and "heterocycloalkyl". Unsaturated heterocycles include dihydroimidazolyl, in particular 1-(methylsulfonyl)-4,5-dihydro-1H-imidazol-2-yl.

"Heteroaryl" refers to a monocyclic heteroaromatic, or a bicyclic or a tricyclic fused-ring heteroaromatic group. Particular examples of heteroaromatic groups include optionally substituted pyridyl, oxazolyl, pyrazolyl, or triazolyl. Examples of heteroaryl groups according to the present invention are 1-methyl-1H-pyrazol-3-yl, 1-methyl-1H-pyrazol-5-yl, 1H-1,2,4-triazol-3-yl.

"Heterocycloalkyl" refers to a $C_{3-8}$ cycloalkyl group according to the definition above, in which 1 to 3 carbon atoms are replaced by hetero atoms chosen from the group consisting of O, S, NR, R being defined as hydrogen, acyl or $C_{1-6}$ alkyl. Preferred heterocycloalkyl include pyrrolidinyl, piperidinyl, morpholinyl, tetrahydropyranyl, and the like. Examples of heterocycloalkyl groups according to the present invention are pyrrolidin-1-yl, piperidin-1-yl, azetidin-1-yl, and tetrahydro-2H-pyran-4-yl.

"Amino group" refers to the group —NRR' where each R, R' is independently hydrogen, "$C_{1-6}$ alkyl", "$C_{3-8}$ cycloalkyl", "heterocycle", "aryl" and where R and R', together with the nitrogen atom to which they are attached, can optionally form a 3-8-membered heterocycloalkyl ring. "$C_{1-6}$ alkylamino" refers to the group NRR' wherein R is H or $C_{1-6}$ alkyl and R' is $C_{1-6}$ alkyl. Examples of amino groups according to the present invention are amino (—NH$_2$), methylamino and dimethylamino.

"Amido" refers to the group —C(=O)NRR' where each R, R' is independently hydrogen, "$C_{1-6}$ alkyl", "$C_{3-8}$ cycloalkyl", "heterocycle", "aryl", and where R and R', together with the nitrogen atom to which they are attached, can optionally form a 3-8-membered heterocycloalkyl ring. "$C_{1-6}$ alkylamido" refers to the group —C(=O)NRR' wherein R is H or "$C_{1-6}$ alkyl" and R' is "$C_{1-6}$ alkyl". "Heterocyclylamido" refers to the group —C(=O)NRR' wherein one of R or R' is an "heterocycle". "$C_{3-8}$ heterocycloalkylamido" refers to the group —C(=O)NRR' wherein R and R', together with the nitrogen atom to which they are attached, can optionally form a 3-8-membered heterocycloalkyl ring. Examples of amido groups according to the present invention are carbamoyl, methylcarbamoyl, dimethylcarbamoyl.

"Acyl" refers to the group —C(=O)R where R is "$C_{1-6}$ alkyl", "$C_{3-8}$ cycloalkyl", "heterocycle" or "aryl". "$C_{1-6}$ alkylacyl" refers to the group —C(=O)R where R is "$C_{1-6}$ alkyl". Example of acyl group according to the present invention is acetyl.

"Acylamino" refers to the group —NHC(=O)R where R is "$C_{1-6}$ alkyl", "$C_{3-8}$ cycloalkyl", "heterocycle" or "aryl". "($C_{1-6}$-alkylacyl)amino" refers to the group —NHC(=O)R where R is "$C_{1-6}$ alkyl". Example of acylamino group according to the present invention is acetamido.

The term "alkoxycarbonyl" refers to the group —C(O)OR wherein R includes "$C_{1-6}$ alkyl", "$C_{3-8}$ cycloalkyl", "heterocycle" or "aryl". "$C_{1-6}$ alkoxycarbonyl" refers to the group —C(O)OR wherein R is "$C_{1-6}$ alkyl". Example of alkoxycarbonyl according to the present invention is methoxycarbonyl.

"Alkoxycarbonyloxy" refers to the group —OC(O)OR wherein R includes "$C_{1-6}$ alkyl", "$C_{3-8}$ cycloalkyl", "heterocycle" or "aryl". "$C_{1-6}$ alkoxycarbonyloxy" refers to the group —OC(O)OR wherein R is "$C_{1-6}$ alkyl".

"Aminocarbonyloxy" refers to the group —OC(O)NRR' wherein R and R' are defined as above for amino groups. "$C_{1-6}$ aminocarbonyloxy" refers to the group —OC(O)NRR' wherein R is H or "$C_{1-6}$ alkyl" and R' is "$C_{1-6}$ alkyl".

"Sulfonyl" as used herein refers to a group of formula "—SO$_2$—R" wherein R is "$C_{1-6}$ alkyl", "$C_{3-8}$ cycloalkyl", "heterocycle" or "aryl". "$C_{1-6}$ alkylsulfonyl" refers to a sulfonyl group wherein R is a "$C_{1-6}$ alkyl". Examples of sulfonyl group according to the present invention are methylsulfonyl and (tetrahydro-2H-pyran-4-ylmethyl)sulfonyl.

"Sulfinyl" refers to group of formula "—S(O)—R" wherein R is "$C_{1-6}$ alkyl", "$C_{3-8}$ cycloalkyl", "heterocycle" or "aryl". "$C_{1-6}$ alkylsulfinyl" refers to a sulfinyl group wherein R is "$C_{1-6}$ alkyl".

"Sulfanyl" refers to group of formula "—S—R" wherein R is "$C_{1-6}$ alkyl", "$C_{3-8}$ cycloalkyl", "heterocycle" or "aryl". "$C_{1-6}$ alkylsulfanyl" refers to a sulfanyl group wherein R is "$C_{1-6}$ alkyl".

"Sulfonylamino" as used herein refers to a group of formula —NRSO$_2$—R' wherein R and R' are as defined here above for the amino group. "($C_{1-6}$-alkylsulfonyl)amino" refers to a group of formula —NHSO$_2$—R' wherein R' is "$C_{1-6}$ alkyl". Example of sulfonylamino group according to the present invention is (methylsulfonyl)amino.

"$C_{1-6}$-alkyl sulfonylamino" refers to "$C_{1-6}$ alkyl" having a sulfonylamino as defined here above as substituent. Example is [(methylsulfonyl)amino]methyl.

"Aminosulfonyl" as used herein refers to a group of formula —SO$_2$—NRR' wherein R and R' are as defined here above for the amino group. "$C_{1-6}$ alkylaminosulfonyl" refers to an aminosulfonyl group wherein R is H or "$C_{1-6}$ alkyl" and R' is "$C_{1-6}$ alkyl". "Heterocyclylaminosulfonyl" refers to the group —SO$_2$—NRR' wherein one of R or R' is an "heterocycle". "$C_{3-8}$-heterocycloalkylaminosulfonyl" refers to the group —SO$_2$—NRR' wherein R and R', together with the nitrogen atom to which they are attached, can optionally form a 3-8-membered heterocycloalkyl ring. Example of aminosulfonyl groups according to the present invention are sulfamoyl, methylsulfamoyl (also referred to as methylaminosulfonyl), ethylsulfamoyl (also referred to as ethylaminosulfonyl), (2,2,2-trifluoroethyl)sulfamoyl (also referred to as (2,2,2-trifluoroethyl)aminosulfonyl, propan-2-ylsulfamoyl (also referred to as isopropylaminosulfonyl), pyrrolidin-1-ylsulfonyl, piperidin-1-ylsulfonyl, azetidin-1-ylsulfonyl, (1-methyl-1H-pyrazol-3-yl)sulfamoyl, (1-methyl-1H-pyrazol-5-yl)sulfamoyl, 1H-1,2,4-triazol-3-ylsulfamoyl.

"Aminosulfinyl" as used herein refers to a group of formula —SO—NRR' wherein R and R' are as defined here above for the amino group. "$C_{1-6}$ alkylaminosulfinyl" refers to an aminosulfonyl group wherein R is hydrogen or "$C_{1-6}$ alkyl" and R' is "$C_{1-6}$ alkyl".

"Oxo" as used herein refers to =O.

"Ureido" as used herein refers to a group of formula —NHC(O)NRR' wherein R and R' are as defined here above for the amino group. Example of ureido is (methoxycarbonyl)amino. "$C_{1-6}$ alkylureido" refers to a group of formula —NHC(O)NRR' wherein R is hydrogen or "$C_{1-6}$ alkyl" and R' is "$C_{1-6}$ alkyl".

"Carbamate", as used herein, refers to a group of formula —NRC(O)OR' wherein R and R' are as defined here above for the amino group. "$C_{1-6}$ alkylcarbamate" refers to a group of formula —NRC(O)OR' wherein R is hydrogen or "$C_{1-6}$ alkyl" and R' is "$C_{1-6}$ alkyl".

"$C_{1-6}$-alkyl carbamate" as used herein refers to a "$C_{1-6}$ alkyl" substituted by a carbamate as defined here above.

"N-cyano-S—($C_{1-6}$-alkyl)sulfonimidoyl" refers to a group of formula —SR(O)(N—CN) wherein R is "$C_{1-6}$ alkyl".

"N,S-(di-$C_{1-6}$-alkyl)sulfonimidoyl" refers to a group of formula —SR(O)(N—R') wherein R and R' are "$C_{1-6}$ alkyl".

"(Di-$C_{1-6}$-alkyl)(oxido)-$\lambda^6$-sulfanylidene-amino" refers to a group of formula —N=S(O)RR' wherein R and R' are "$C_{1-6}$ alkyl" or R and R' together with the S atom form a "$C_{3-8}$ heterocycloalkyl".

In one aspect, the present invention provides a compound of formula (I), or a pharmaceutically acceptable salt thereof,

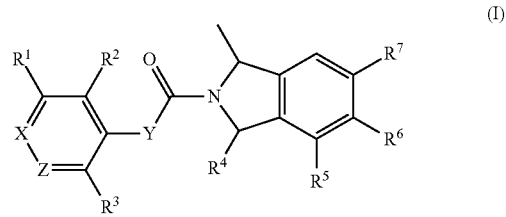

(I)

wherein
R$^1$ is hydrogen, halogen, hydroxy, $C_{1-6}$-alkyl optionally substituted by hydroxy or ($C_{1-6}$-alkylsulfonyl)amino, $C_{1-6}$ alkoxy, $C_{1-6}$ alkylsulfanyl, $C_{1-6}$ alkylsulfinyl, $C_{1-6}$alkylsulfonyl or ($C_{1-6}$-alkylsulfonyl)amino;

R$^2$ is hydrogen, halogen, cyano, $C_{1-6}$ alkyl unsubstituted or substituted by one or more halogens or hydroxy, $C_{1-6}$ alkoxy, $C_{1-6}$ alkylsulfanyl, $C_{1-6}$ alkylsulfinyl, $C_{1-6}$ alkylsulfonyl, $C_{1-6}$ alkylamido, or a group of formula —CH$_2$R$^{2a}$, —NHR$^{2a}$ or —CH$_2$NHR$^{2a}$ wherein R$^{2a}$ is selected from $C_{1-6}$ alkylacyl or $C_{1-6}$ alkylsulfonyl;

or R$^1$ and R$^2$ are linked together to form with the adjacent aromatic group a bicycle of formula (i):

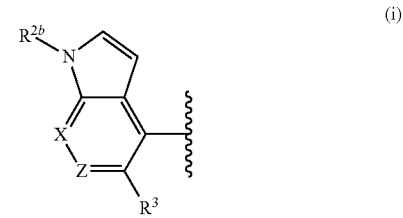

(i)

wherein R$^{2b}$ is hydrogen or $C_{1-6}$ alkylsulfonyl;
R$^3$ is halogen, $C_{1-6}$ alkyl or $C_{1-6}$ alkoxy;
R$^4$ is hydrogen, halogen, $C_{1-6}$ alkyl, hydroxy, $C_{1-6}$ alkoxy, $C_{1-6}$ alkylsulfonyl, $C_{1-6}$ alkoxycarbonyloxy or $C_{1-6}$ aminocarbonyloxy;
R$^5$ is hydrogen, cyano, hydroxy, amino, nitro, $C_{1-6}$ alkoxy optionally substituted by $C_{1-6}$ alkylamido, carbamoyl, ($C_{1-6}$-alkylacyl)amino, sulfamoyl, $C_{1-6}$ alkylsulfinyl, $C_{1-6}$ alkylaminosulfinyl, $C_{1-6}$ alkylsulfonyl optionally substituted by heterocycle or $C_{1-6}$ alkoxy, N-cyano-S—($C_{1-6}$-alkyl)sulfonimidoyl, N,S-(di-$C_{1-6}$-alkyl)sulfonimidoyl, (di-$C_{1-6}$-alkyl)(oxido)-$\lambda^6$-sulfanylidene-amino, ($C_{1-6}$-alkylsulfonyl)amino; or R$^5$ is $C_{1-6}$ alkyl mono- or polysubstituted by hydroxy, halogen, $C_{1-6}$ alkylsulfanyl, $C_{1-6}$ alkylsulfonyl, ($C_{1-6}$-alkylsulfonyl)amino, ($C_{1-6}$-alkylacyl)amino, $C_{1-6}$ alkylureido, $C_{1-6}$ alkylcarbamate, $C_{1-6}$ alkoxycarbonyloxy; or R$^5$ is an heterocycle optionally mono- or polysubstituted by $C_{1-6}$ alkyl or $C_{1-6}$ alkylsulfonyl; or R$^5$ is an amido group selected from $C_{1-6}$ alkylamido optionally mono- or polysubstituted by halogen, substituted or unsubstituted heterocyclylamido, $C_{3-8}$ heterocycloalkylamido optionally mono- or polysubstituted by $C_{1-6}$ alkyl, halogens or hydroxy; or R$^5$ is an aminosulfonyl group selected from $C_{1-6}$ alkylaminosulfonyl optionally substituted by one or more halogens or cyano, heterocyclylaminosulfonyl or $C_{3-8}$ heterocycloalkylaminosulfonyl optionally substituted by one or more halogens;
R$^6$ is hydrogen or cyano;
R$^7$ is either hydrogen or ($C_{1-6}$-alkylsulfonyl)amino;

X is either $CR^9$ or N, wherein $R^9$ is hydrogen, halogen or $C_{1-6}$-alkyl hydroxy;
Z is CH or N; and
Y is either $CH_2$ or NH.

Suitably, $R^1$ is hydrogen, halogen, or hydroxy; or $C_{1-6}$ alkyl, $C_{1-6}$ alkoxy or ($C_{1-6}$-alkylsulfonyl)amino($C_{1-6}$alkyl), any of which groups may be substituted by one or more substitutents.

In a first embodiment, $R^1$ is hydrogen. In a second embodiment, $R^1$ is halogen. In a third embodiment, $R^1$ is hydroxy. In a fourth embodiment, $R^1$ is optionally substituted $C_{1-6}$ alkyl. In a first aspect of that embodiment, $R^1$ is $C_{1-6}$ alkyl. In a second aspect of this embodiment, $R^1$ is methyl. In another aspect of this embodiment, $R^1$ is $C_{1-6}$ alkyl substituted by hydroxy. In a particular aspect of this embodiment, $R^1$ is hydroxymethyl. In a fifth embodiment, $R^1$ is optionally substituted $C_{1-6}$ alkoxy. In one aspect of this embodiment, $R^1$ is $C_{1-6}$ alkoxy. In a particular aspect of said embodiment, $R^1$ is methoxy. In a seventh embodiment, $R^1$ is optionally substituted ($C_{1-6}$-alkylsulfonyl)amino($C_{1-6}$alkyl). In one aspect of this embodiment, $R^1$ is ($C_{1-6}$-alkylsulfonyl)amino($C_{1-6}$alkyl). In a particular aspect of this embodiment, $R^1$ is (methylsulfonyl)amino(methyl).

Particular optional substituents on $R^1$ include hydroxy.

In one specific embodiment, $R^1$ is hydrogen, hydroxy, $C_{1-6}$ alkyl optionally substituted by hydroxy or ($C_{1-6}$-alkylsulfonyl)amino or $C_{1-6}$ alkoxy.

In another specific embodiment, $R^1$ is hydrogen, hydroxy, methyl, hydroxymethyl, methoxy, [(methylsulfonyl)amino]methyl.

In a further embodiment, $R^1$ is hydrogen or hydroxymethyl.

Suitably, $R^2$ is cyano or halogen; or $C_{1-6}$ alkyl, which group may be substituted by one or more substituents.

In a first embodiment, $R^2$ is cyano. In a second embodiment, $R^2$ is halogen. In a first aspect of this embodiment, $R^2$ is chloro. In a second aspect of this embodiment, $R^2$ is iodo. In a third aspect of this embodiment, $R^2$ is bromo. In a third embodiment, $R^2$ is optionally substituted $C_{1-6}$ alkyl. In one aspect of this embodiment, $R^2$ is $C_{1-6}$ alkyl. In a particular aspect of this embodiment, $R^2$ is methyl. In another aspect of this embodiment, $R^2$ is $C_{1-6}$ alkyl substituted by hydroxy. In a particular aspect of this embodiment, $R^2$ is hydroxymethyl.

Particular optional substituents on $R^2$ include hydroxy.

In one particular embodiment, $R^2$ is halogen, cyano, amino, or $C_{1-6}$ alkyl optionally substituted by hydroxy.

In a further specific embodiment, $R^2$ is chloro, iodo, bromo, cyano, methyl or hydroxymethyl.

Suitably, $R^2$ is halogen or cyano.

In a first embodiment, $R^2$ is halogen. In one aspect of this embodiment, $R^2$ is chloro. In a second embodiment, $R^2$ is cyano.

In a particular embodiment, $R^2$ is chloro or cyano.

Particularly, $R^2$ is chloro.

Alternatively, $R^1$ and $R^2$ are linked together to form with the adjacent aromatic group a bicycle of formula (i):

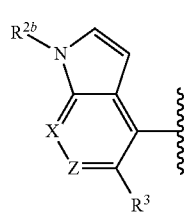

(i)

wherein $R^{2b}$ is hydrogen.

In a specific embodiment, $R^1$ and $R^2$ are linked together to form with the adjacent aromatic group a 1H-pyrrolo[2,3-b]pyridin-4-yl group.

Suitably, $R^3$ is halogen or cyano.

In a first embodiment, $R^3$ is halogen. In one aspect of this embodiment, $R^3$ is chloro. In a second embodiment, $R^3$ is cyano.

In a particular embodiment, $R^3$ is chloro or cyano.

In a preferred embodiment, $R^3$ is chloro.

In one specific embodiment, $R^4$ is hydrogen.

Suitably, $R^5$ is hydrogen, hydroxy or nitro; or $C_{1-6}$ alkyl; $C_{1-6}$ alkoxy, $C_{1-6}$-alkylsulfonyl, $C_{1-6}$-alkylsulfonylamino; $C_{1-6}$-alkylsulfonylamino($C_{1-6}$ alkyl), heterocycle, $C_{1-6}$ alkylacylamino; amido; $C_{1-6}$alkoxycarbonyl, amino group; aminosulfonyl; (di-$C_{1-6}$-alkyl)(oxido)-$\lambda^6$-sulfanylidene-amino or amido($C_{1-6}$ alkoxy); any of which groups may be optionally substituted by one or more substituents.

In a first embodiment, $R^5$ is hydrogen. In a second embodiment, $R^5$ is hydroxy. In a third embodiment, $R^5$ is nitro.

In a fourth embodiment, $R^5$ is optionally substituted $C_{1-6}$ alkyl. In one aspect of this embodiment, $R^5$ is optionally substituted methyl. In one aspect of this embodiment, $R^5$ is optionally substituted ethyl.

In a fifth embodiment, $R^5$ is optionally substituted $C_{1-6}$ alkoxy. In one aspect of this embodiment, $R^5$ is optionally substituted methoxy.

In a sixth embodiment, $R^5$ is optionally substituted $C_{1-6}$-alkylsulfonyl. In first aspect of this embodiment, $R^5$ is optionally substituted methylsulfonyl.

In a seventh embodiment, $R^5$ is optionally substituted $C_{1-6}$-alkylsulfonylamino. In one aspect of this embodiment, $R^5$ is optionally substituted methylsulfonylamino.

In an eighth embodiment, $R^5$ is $C_{1-6}$-alkylsulfonylamino ($C_{1-6}$ alkyl). In first aspect of this embodiment, $R^5$ is optionally substituted methylsulfonylaminomethyl.

In a ninth embodiment, $R^5$ is an optionally substituted heterocycle. In one aspect of this embodiment $R^5$ is optionally substituted heteroaryl. In a particular aspect of this embodiment, $R^5$ is optionally substituted pyrazolyl, In a tenth embodiment, $R^5$ is optionally substituted $C_{1-6}$ alkylacylamino. In one aspect of this embodiment, $R^5$ is methylcarbonylamino.

In a eleventh embodiment, $R^5$ is optionally substituted amido. In a first aspect of this embodiment, $R^5$ is carbamoyl.

In a twelfth embodiment, $R^5$ is optionally substituted $C_{1-6}$alkoxycarbonyl. In one aspect, $R^5$ is methoxycarbonyl.

In a thirteenth embodiment, $R^5$ is an optionally substituted amino group. In one aspect of this embodiment, $R^5$ is amino.

In a fourteenth embodiment; $R^5$ is optionally substituted aminosulfonyl. In a first aspect of this embodiment, $R^5$ is optionally substituted $C_{1-6}$ alkylaminosulfonyl. In a second aspect of this embodiment, $R^5$ is optionally substituted heterocyclylaminosulfonyl. In a third aspect of this embodiment, $R^5$ is optionally substituted $C_{3-8}$heterocycloalkylaminosulfonyl In a fifteenth embodiment, $R^5$ is optionally substituted (di-$C_{1-6}$-alkyl)(oxido)-$\lambda^6$-sulfanylidene-amino. In one aspect of this embodiment, $R^5$ is (di-methyl)(oxido)-$\lambda^6$-sulfanylidene-amino.

In a sixteenth embodiment, $R^5$ is optionally substituted amido($C_{1-6}$ alkoxy). In one aspect of this embodiment, $R^5$ is optionally substituted $C_{1-6}$ alkylamido($C_{1-6}$ alkoxy). In a particular aspect of this embodiment, $R^5$ is optionally substituted $C_{1-6}$ alkylamidomethoxy. In one specific embodiment, $R^5$ is hydrogen, cyano, hydroxy, amino, nitro, $C_{1-6}$ alkoxy optionally substituted by $C_{1-6}$ alkylamido, $C_{1-6}$ alkoxycarbonyl, carbamoyl, ($C_{1-6}$-alkylacyl)amino, $C_{1-6}$ alkylsulfonyl optionally substituted by a heterocycle, ($C_{1-6}$-alkylsulfonyl)amino; or $R^5$ is $C_{1-6}$ alkyl mono- or polysubstituted by hydroxy; or $R^5$ is an aminosulfonyl group selected from $C_{1-6}$ alkylaminosulfonyl optionally substituted by one or more halogens, heterocyclylaminosulfonyl or $C_{3-8}$ heterocycloalkylaminosulfonyl.

Typically, $R^5$ is hydrogen, hydroxy or nitro; or methyl, ethyl, methoxy, methylsulfonyl, methylsulfonylamino, methylsulfonylaminomethyl; pyrazolyl, methylcarbonylamino, carbamoyl, methoxycarbonyl, amino; $C_{1-6}$ alkylaminosulfonyl, heterocyclylaminosulfonyl, $C_{3-8}$heterocycloalkylaminosulfonyl, (di-methyl)(oxido)-$\lambda^6$-sulfanylidene-amino, methylaminocarbonylmethoxy, or dimethylaminocarbonylmethoxy, which groups may be optionally substituted by one or more substitutents.

Typical examples of optional substituents on $R^5$ include one, two or three substituents independently selected from halogen, hydroxy, oxo, $C_{1-6}$ alkyl, tetrahydropyranyl, and trifluoromethyl.

Illustrative examples of optional substitutents on $R^5$ include one, two or three substitutents independently selected from fluoro, hydroxy, oxo, methyl, isopropyl, tetrahydropyranyl and trifluromethyl.

In another specific embodiment, $R^5$ is hydrogen, cyano, hydroxy, amino, nitro, $C_{1-6}$ alkoxy optionally substituted by $C_{1-6}$ alkylamido, $C_{1-6}$ alkoxycarbonyl, carbamoyl, ($C_{1-6}$-alkylacyl)amino, $C_{1-6}$ alkylsulfonyl optionally substituted by tetrahydropyranyl, ($C_{1-6}$-alkylsulfonyl)amino; or $R^5$ is $C_{1-6}$-alkyl hydroxy or $C_{1-6}$-alkyl sulfonylamino; $C_{1-6}$ alkylaminosulfonyl optionally substituted by one or more halogens, substituted or unsubstituted 1H-pyrazol-3-ylsulfamoyl, substituted or unsubstituted 1H-pyrazol-5-ylsulfamoyl, substituted or unsubstituted 1H-1,2,4-triazol-3-ylsulfamoyl substituted or unsubstituted pyrrolidin-1-ylsulfonyl, substituted or unsubstituted azetidin-1-ylsulfonyl, substituted or unsubstituted piperidin-1-ylsulfonyl.

In a particular embodiment, $R^5$ is hydrogen, $C_{1-6}$-alkyl hydroxy, ($C_{1-6}$-alkylsulfonyl)amino; or $C_{1-6}$ alkylaminosulfonyl optionally substituted by one or more halogens.

Suitably, $R^5$ is hydrogen, hydroxy, nitro; (trifluoro)(hydroxyl)ethyl, (hydroxy)methyl, methoxy, methylsulfonyl, methylsulfonylamino, methylsulfonylaminomethyl; pyrazolyl, methylcarbonylamino, carbamoyl, methoxycarbonyl, amino; methylaminosulfonyl; isopropylaminosulfonyl, ethylaminosulfonyl, (trifluromethyl)methylaminosufonyl, triazolylaminosulfonyl, (methyl)pyrazolylaminosulfonyl, (tetrahydropyranyl)methylsulfonyl, pyrrolidinylaminosulfonyl, piperidinylaminosulfonyl, azetidinylaminosulfonyl, (di-methyl)(oxido)-$\lambda^6$-sulfanylidene-amino, methylaminocarbonylmethoxy, or dimethylaminocarbonylmethoxy.

Examples of $R^5$ groups according to the invention are hydrogen, hydroxy, amino, nitro, methoxy, 2-(methylamino)-2-oxoethoxy, 2-(dimethylamino)-2-oxoethoxy, hydroxymethyl, methoxycarbonyl, acetamido, (methylsulfonyl)amino, [(methylsulfonyl)amino]methyl, carbamoyl, azetidin-1-ylsulfonyl, pyrrolidin-1-ylsulfonyl, piperidin-1-ylsulfonyl, methylsulfonyl, (tetrahydro-2H-pyran-4-ylmethyl)sulfonyl, methylsulfamoyl, ethylsulfamoyl, (2,2,2-trifluoroethyl)sulfamoyl, propan-2-ylsulfamoyl, (1-methyl-1H-pyrazol-3-yl)sulfamoyl, 1H-1,2,4-triazol-3-ylsulfamoyl or (1-methyl-1H-pyrazol-5-yl)sulfamoyl. Additional examples of $R^5$ groups according to the invention, include (di-methyl)(oxido)-$\lambda^6$-sulfanylidene-amino, 1H-pyrazolyl, or 2,2,2-trifluoro-1-hydroxy-ethyl, Particularly, $R^5$ is hydrogen, hydroxymethyl, (methylsulfonyl)amino, [(methylsulfonyl)amino]methyl, methylsulfamoyl, ethylsulfamoyl, (2,2,2-trifluoroethyl)sulfamoyl, propan-2-ylsulfamoyl, (di-methyl)(oxido)-$\lambda^6$-sulfanylideneamino, 1H-pyrazolyl, or 2,2,2-trifluoro-1-hydroxy-ethyl.

In a specific embodiment, $R^5$ groups are selected from hydrogen, hydroxymethyl, (methylsulfonyl)amino, [(methylsulfonyl)amino]methyl, methylsulfamoyl, ethylsulfamoyl, (2,2,2-trifluoroethyl)sulfamoyl and propan-2-ylsulfamoyl.

In another specific embodiment, $R^5$ is hydrogen, hydroxymethyl, (methylsulfonyl)amino, methylsulfamoyl, 2,2,2-trifluoro-1-hydroxy-ethyl or (di-methyl)(oxido)$\lambda^6$-sulfanylidene-amino.

In a particularly preferred embodiment, $R^5$ groups may be selected from hydrogen, hydroxymethyl, (methylsulfonyl)amino or methylsulfamoyl.

In one specific embodiment, $R^6$ is hydrogen.
In one specific embodiment, $R^7$ is hydrogen.
In one specific embodiment, X is either $CR^9$ or N, wherein $R^9$ is hydrogen.
In one specific embodiment, X is CH.
In another specific embodiment, X is N.
In one specific embodiment, Z is CH.
In one specific embodiment, Y is $CH_2$.
In another specific embodiment, Y is NH.
In a particular embodiment, the 1-methyl-1,3-dihydroisoindolin-2(1H)-yl has the (S) configuration.
In another particular embodiment, the 1-methyl-1,3-dihydroisoindolin-2(1H)-yl I has the (R) configuration.
In a particular embodiment, the present invention relates to isoindoline derivatives according to formula I,

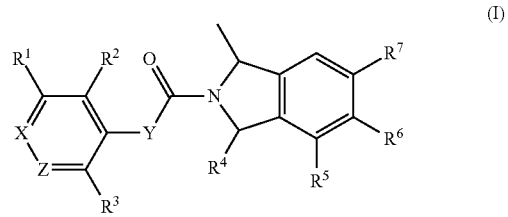

(I)

wherein
$R^1$ is hydrogen, hydroxy, $C_{1-6}$ alkyl optionally substituted by hydroxy or ($C_{1-6}$-alkyl-sulfonyl)amino, or $C_{1-6}$ alkoxy;
$R^2$ is halogen, cyano, amino, or $C_{1-6}$ alkyl optionally substituted by hydroxyl;
or $R^1$ and $R^2$ are linked together to form with the adjacent aromatic group a bicycle of formula (i):

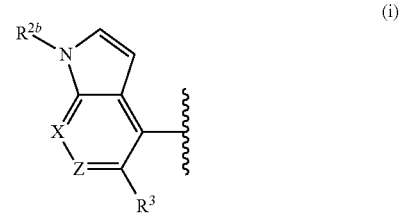

(i)

wherein $R^{2b}$ is hydrogen;
$R^3$ is halogen;
$R^4$ is hydrogen;
$R^5$ is hydrogen, cyano, hydroxy, amino, nitro, $C_{1-6}$ alkoxy optionally substituted by $C_{1-6}$ alkylamido, $C_{1-6}$ alkoxycarbonyl, carbamoyl, ($C_{1-6}$-alkylacyl)amino, $C_{1-6}$ alkylsulfonyl optionally substituted by tetrahydropyranyl, ($C_{1-6}$-alkylsulfonyl)amino; or $R^5$ is $C_{1-6}$-alkyl hydroxy, $C_{1-6}$-alkyl sulfonylamino, $C_{1-6}$ alkylaminosulfonyl optionally substituted by one or more halogens, substituted or unsubstituted 1H-pyrazol-3-ylsulfamoyl, substituted or unsubstituted 1H-pyrazol-5-ylsulfamoyl, substituted or unsubstituted 1H-1,2,4-triazol-3-ylsulfamoyl, substituted or unsubstituted pyrrolidin-1-ylsulfonyl, substituted or unsubstituted azetidin-1-ylsulfonyl, substituted or unsubstituted piperidin-1-ylsulfonyl;

$R^6$ is hydrogen or cyano;
$R^7$ is hydrogen;
X is either CH or N, wherein $R^9$ is hydrogen;
Z is CH or N; and
Y is either $CH_2$ or NH.

A particular sub-class of compounds of formula (I) according to the present invention is represented by isoindoline derivatives of formula I-A,

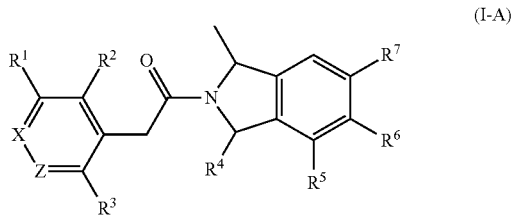

(I-A)

wherein $R^1$, $R^2$, $R^3$, $R^4$, $R^5$, $R^6$, $R^7$, X and Z are as defined above for compounds of formula I.

A particular sub-group of compounds of formula (I-A) is represented by compound of formula (IA-A),

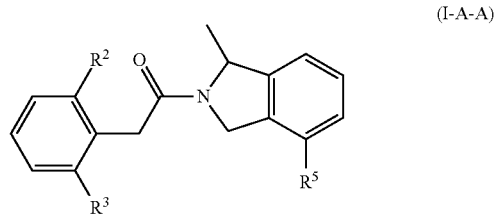

(I-A-A)

wherein $R^2$, $R^3$ and $R^5$ are as defined above.

Suitably, the present invention relates to compounds of formula (I-A-A) wherein
$R^2$ and $R^3$ are independently halogen or cyano, and
$R^5$ is hydrogen, hydroxy or nitro; or $C_{1-6}$ alkyl; $C_{1-6}$ alkoxy, $C_{1-6}$-alkylsulfonyl, $C_{1-6}$-alkylsulfonylamino; $C_{1-6}$-alkylsulfonylamino($C_{1-6}$ alkyl), heterocycle, $C_{1-6}$ alkylacylamino; amido; $C_{1-6}$alkoxycarbonyl, amino group; aminosulfonyl; (di-$C_{1-6}$-alkyl)(oxido)-$\lambda^6$-sulfanylidene-amino or amido ($C_{1-6}$ alkoxy); any of which groups may be optionally substituted by one or more substituents.

In one embodiment, $R^2$ represents halogen. In a particular aspect of this embodiment, $R^2$ represents chloro. In another embodiment, $R^2$ represents cyano.

In one embodiment, $R^3$ represents halogen. In a particular aspect of this embodiment, $R^3$ represents chloro. In another embodiment, $R^3$ represents cyano.

In a first embodiment, $R^5$ is hydrogen. In a second embodiment, $R^5$ is hydroxy. In a third embodiment, $R^5$ is nitro.

In a fourth embodiment, $R^5$ is optionally substituted $C_{1-6}$ alkyl. In one aspect of this embodiment, $R^5$ is optionally substituted methyl. In one aspect of this embodiment, $R^5$ is optionally substituted ethyl.

In a fifth embodiment, $R^5$ is optionally substituted $C_{1-6}$ alkoxy. In one aspect of this embodiment, $R^5$ is optionally substituted methoxy.

In a sixth embodiment, $R^5$ is optionally substituted $C_{1-6}$-alkylsulfonyl. In first aspect of this embodiment, $R^5$ is optionally substituted methylsulfonyl.

In a seventh embodiment, $R^5$ is optionally substituted $C_{1-6}$-alkylsulfonylamino. In one aspect of this embodiment, $R^5$ is optionally substituted methylsulfonylamino.

In an eighth embodiment, $R^5$ is $C_{1-6}$-alkylsulfonylamino ($C_{1-6}$ alkyl). In first aspect of this embodiment, $R^5$ is optionally substituted methylsulfonylaminomethyl.

In a ninth embodiment, $R^5$ is an optionally substituted heterocycle. In one aspect of this embodiment $R^5$ is optionally substituted heteroaryl. In a particular aspect of this embodiment, $R^5$ is optionally substituted pyrazolyl.

In a tenth embodiment, $R^5$ is optionally substituted $C_{1-6}$ alkylacylamino. In one aspect of this embodiment, $R^5$ is methylcarbonylamino.

In an eleventh embodiment, $R^5$ is optionally substituted amido. In a first aspect of this embodiment, $R^5$ is carbamoyl.

In a twelfth embodiment, $R^5$ is optionally substituted $C_{1-6}$alkoxycarbonyl. In one aspect, $R^5$ is methoxycarbonyl.

In a thirteenth embodiment, $R^5$ is an optionally substituted amino group. In one aspect of this embodiment, $R^5$ is amino.

In a fourteenth embodiment; $R^5$ is optionally substituted aminosulfonyl. In a first aspect of this embodiment, $R^5$ is optionally substituted $C_{1-6}$ alkylaminosulfonyl. In a second aspect of this embodiment, $R^5$ is optionally substituted heterocyclylaminosulfonyl. In a third aspect of this embodiment, $R^5$ is optionally substituted $C_{3-8}$heterocycloalkylaminosulfonyl In a fifteenth embodiment, $R^5$ is optionally substituted (di-$C_{1-6}$-alkyl)(oxido)-$\lambda^6$-sulfanylidene-amino. In one aspect of this embodiment, $R^5$ is (di-methyl)(oxido)-$\lambda^6$-sulfanylidene-amino.

In a sixteenth embodiment, $R^5$ is optionally substituted amido($C_{1-6}$ alkoxy). In one aspect of this embodiment, $R^5$ is optionally substituted $C_{1-6}$ alkylamido($C_{1-6}$ alkoxy). In a particular aspect of this embodiment, $R^5$ is optionally substituted $C_{1-6}$ alkylamidomethoxy.

In a particular embodiment, $R^5$ is hydrogen, cyano, hydroxy, amino, nitro, $C_{1-6}$ alkoxy optionally substituted by $C_{1-6}$ alkylamido, $C_{1-6}$ alkoxycarbonyl, carbamoyl, ($C_{1-6}$-alkylacyl)amino, $C_{1-6}$ alkylsulfonyl optionally substituted by tetrahydropyranyl, ($C_{1-6}$-alkylsulfonyl)amino; or $R^5$ is $C_{1-6}$-alkyl hydroxy or $C_{1-6}$-alkyl sulfonylamino; $C_{1-6}$ alkylaminosulfonyl optionally substituted by one or more halogens, substituted or unsubstituted 1H-pyrazol-3-ylsulfamoyl, substituted or unsubstituted 1H-pyrazol-5-ylsulfamoyl, substituted or unsubstituted 1H-1,2,4-triazol-3-ylsulfamoyl substituted or unsubstituted pyrrolidin-1-ylsulfonyl, substituted or unsubstituted azetidin-1-ylsulfonyl, substituted or unsubstituted piperidin-1-ylsulfonyl.

Specific examples of $R^5$ include hydrogen, hydroxymethyl, (methylsulfonyl)amino, [(methylsulfonyl)amino] methyl, methylsulfamoyl, ethylsulfamoyl, (2,2,2-trifluoroethyl)sulfamoyl, propan-2-ylsulfamoyl, (di-methyl)(oxido)-$\lambda^6$-sulfanylidene-amino, 1H-pyrazolyl, and 2,2,2-trifluoro-1-hydroxy-ethyl.

Another particular sub-class of compounds of formula (I) according to the present invention is represented by isoindoline derivatives of formula I-B,

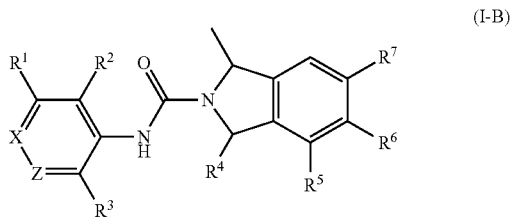

(I-B)

wherein $R^1$, $R^2$, $R^3$, $R^4$, $R^5$, $R^6$, $R^7$, X and Z are defined as above for compounds of formula I.

Specific novel compounds in accordance with the present invention include each of the compounds whose preparation is described in the accompanying Examples, and pharmaceutically acceptable salts, solvates thereof, and co-crystals thereof.

Therefore, in a particular aspect, the present invention relates to compounds of formula (I) which are those selected from the group consisting of:

2-(2,6-dichlorophenyl)-1-(1-methyl-1,3-dihydro-2H-isoindol-2-yl)ethanone;
2-(2,6-dichlorophenyl)-1-[(1S)-1-methyl-1,3-dihydro-2H-isoindol-2-yl]ethanone;
2-(2,6-dichlorophenyl)-1-[(1R)-1-methyl-1,3-dihydro-2H-isoindol-2-yl]ethanone;
2-(2-chloro-6-iodophenyl)-1-(1-methyl-1,3-dihydro-2H-isoindol-2-yl)ethanone;
2-(2,4-dichloropyridin-3-yl)-1-(1-methyl-1,3-dihydro-2H-isoindol-2-yl)ethanone;
2-(2,6-dichlorophenyl)-1-(1-methyl-4-nitro-1,3-dihydro-2H-isoindol-2-yl)ethanone;
3-chloro-2-{2-[(1S)-1-methyl-1,3-dihydro-2H-isoindol-2-yl]-2-oxoethyl}benzonitrile;
2-(3,5-dichloro-2-methylpyridin-4-yl)-1-[(1S)-1-methyl-1,3-dihydro-2H-isoindol-2-yl]ethanone;
2-(3-bromo-5-chloropyridin-4-yl)-1-[(1S)-1-methyl-1,3-dihydro-2H-isoindol-2-yl]ethanone;
2-(5-chloro-1H-pyrrolo[2,3-b]pyridin-4-yl)-1-[(1S)-1-methyl-1,3-dihydro-2H-isoindol-2-yl]ethanone;
2-(3,5-dichloro-2-methoxypyridin-4-yl)-1-[(1S)-1-methyl-1,3-dihydro-2H-isoindol-2-yl]ethanone;
2-(3,5-dichloropyridin-4-yl)-1-[(1S)-1-methyl-1,3-dihydro-2H-isoindol-2-yl]ethanone;
N-{(1S)-2-[(2,6-dichlorophenyl)acetyl]-1-methyl-2,3-dihydro-1H-isoindol-4-yl}methanesulfonamide;
1-[(1S)-4-amino-1-methyl-1,3-dihydro-2H-isoindol-2-yl]-2-(2,6-dichlorophenyl)ethanone;
methyl 2-[(2,6-dichlorophenyl)acetyl]-1-methyl-2,3-dihydro-1H-isoindole-4-carboxylate;
2-[2,6-dichloro-3-(hydroxymethyl)phenyl]-1-(1-methyl-1,3-dihydro-2H-isoindol-2-yl)ethanone;
2-[2,6-dichloro-3-(hydroxymethyl)phenyl]-1-[(1S)-1-methyl-1,3-dihydro-2H-isoindol-2-yl]ethanone;
2-(2,6-dichlorophenyl)-1-(4-hydroxy-1-methyl-1,3-dihydro-2H-isoindol-2-yl)ethanone;
2-[(2,6-dichlorophenyl)acetyl]-1-methyl-2,3-dihydro-1H-isoindole-4-carboxamide;
N-{2-[(2,6-dichlorophenyl)acetyl]-1-methyl-2,3-dihydro-1H-isoindol-4-yl}acetamide;
2-({2-[(2,6-dichlorophenyl)acetyl]-1-methyl-2,3-dihydro-1H-isoindol-4-yl}oxy)-N-methylacetamide;
2-({2-[(2,6-dichlorophenyl)acetyl]-1-methyl-2,3-dihydro-1H-isoindol-4-yl}oxy)-N,N-dimethylacetamide;
2-(2,6-dichlorophenyl)-1-(4-methoxy-1-methyl-1,3-dihydro-2H-isoindol-2-yl)ethanone;
(1S)-2-[(2,6-dichlorophenyl)acetyl]-N,1-dimethyl-2,3-dihydro-1H-isoindole-4-sulfonamide;
2-[(2,6-dichlorophenyl)acetyl]-1-methyl-2,3-dihydro-1H-isoindole-5-carbonitrile2-[2-chloro-6-(hydroxymethyl)phenyl]-1-[(1S)-1-methyl-1,3-dihydro-2H-isoindol-2-yl]ethanone;
2-(2,6-dichlorophenyl)-1-[(1R)-4-(hydroxymethyl)-1-methyl-1,3-dihydro-2H-isoindol-2-yl]ethanone;
2-(2,6-dichlorophenyl)-1-[(1S)-4-(hydroxymethyl)-1-methyl-1,3-dihydro-2H-isoindol-2-yl]ethanone;
3,5-dichloro-4-{2-[(1S)-1-methyl-1,3-dihydro-2H-isoindol-2-yl]-2-oxoethyl}pyridin-2(1H)-one;
2-(2,6-dichlorophenyl)-1-[1-methyl-4-(methylsulfonyl)-1,3-dihydro-2H-isoindol-2-yl]ethanone;
2-(2,6-dichlorophenyl)-1-[(1S)-1-methyl-4-(pyrrolidin-1-ylsulfonyl)-1,3-dihydro-2H-isoindol-2-yl]ethanone;
2-(2,6-dichlorophenyl)-1-[(1S)-1-methyl-4-(piperidin-1-ylsulfonyl)-1,3-dihydro-2H-isoindol-2-yl]ethanone;
1-[(1S)-4-(azetidin-1-ylsulfonyl)-1-methyl-1,3-dihydro-2H-isoindol-2-yl]-2-(2,6-dichlorophenyl)ethanone;
(1S)-2-[(2,6-dichlorophenyl)acetyl]-1-methyl-N-(propan-2-yl)-2,3-dihydro-1H-isoindole-4-sulfonamide;
(1S)-2-[(2,6-dichlorophenyl)acetyl]-N-ethyl-1-methyl-2,3-dihydro-1H-isoindole-4-sulfonamide;
(1S)-2-[(2,6-dichlorophenyl)acetyl]-1-methyl-N-(2,2,2-trifluoroethyl)-2,3-dihydro-1H-isoindole-4-sulfonamide;
(1S)-2-[(2,6-dichlorophenyl)acetyl]-1-methyl-N-(1-methyl-1H-pyrazol-3-yl)-2,3-dihydro-1H-isoindole-4-sulfonamide;
(1S)-2-[(2,6-dichlorophenyl)acetyl]-1-methyl-N-(4H-1,2,4-triazol-3-yl)-2,3-dihydro-1H-isoindole-4-sulfonamide;
(1S)-2-[(2,6-dichlorophenyl)acetyl]-1-methyl-N-(1-methyl-1H-pyrazol-5-yl)-2,3-dihydro-1H-isoindole-4-sulfonamide;
N-({2-[(2,6-dichlorophenyl)acetyl]-1-methyl-2,3-dihydro-1H-isoindol-4-yl}methyl)methanesulfonamide;
N-(2,4-dichloro-3-{2-[(1S)-1-methyl-1,3-dihydro-2H-isoindol-2-yl]-2-oxoethyl}benzyl)methanesulfonamide;
2-(2,6-dichlorophenyl)-1-{(1S)-1-methyl-4-[(tetrahydro-2H-pyran-4-ylmethyl)sulfonyl]-1,3-dihydro-2H-isoindol-2-yl}ethanone;
(1S)—N-(2,6-dichlorophenyl)-1-methyl-1,3-dihydro-2H-isoindole-2-carboxamide;
(1S)—N-(2-chloro-6-methylphenyl)-1-methyl-1,3-dihydro-2H-isoindole-2-carboxamide;
2-(2,6-dichlorophenyl)-1-[(1S)-4-{[dimethyl(oxido)-$\lambda^6$-sulfanylidene]amino}-1-methyl-1,3-dihydro-2H-isoindol-2-yl]ethanone;
2-(2,6-dichlorophenyl)-1-[(1S)-1-methyl-4-(1H-pyrazol-4-yl)-1,3-dihydro-2H-isoindol-2-yl]ethanone;
2-(5-chloro-1H-indol-4-yl)-1-[(1S)-1-methyl-1,3-dihydro-2H-isoindol-2-yl]ethanone; and
3-chloro-2-(2-{(1S)-1-methyl-4-[2,2,2-trifluoro-1-hydroxyethyl]-1,3-dihydro-2H-isoindol-2-yl}-2-oxoethyl)benzonitrile.

Compounds according to the present invention may be used in monotherapy or combination therapy.

As used herein, the term «combination therapy» refers to the administration of the compound of Formula I together with at least one additional pharmaceutical or medicinal agent (e.g antiparkinsonian or antischizophrenia agent), either in a sequential or simultaneous way.

The present invention includes the use of a combination of a compound of Formula I and one or more additional pharmaceutically active agent(s). If a combination of active agents is administered, then they may be administered sequentially or simultaneously, in separate dosage forms or combined in a single dosage form.

Various pharmaceutically active agents may be selected for use in conjunction with the compound of Formula I, depending on the disease, disorder or condition to be treated.

Pharmaceutically active agents that may be used in combination with the compositions of the present invention include, without limitation:

Levodopa (or its methyl or ethyl ester), alone or in combination with a DOPA decarboxylase inhibitor (e.g. carbidopa (SINEMET®, CARBILEV®, PARCOPA®));

N-methyl-D-aspartate (NMDA) receptor antagonists such as memantine (NAMENDA®, AXURA®, EBIXA®) or amantadine (SYMMETREL®);

Monoamine oxidase (MAO) inhibitors such as selegiline (EMSAM®, ZELAPAR®) or rasagiline (AZILATECT®);

Catechol-O-methyl transferase (COMT) inhibitors like entacapone (COMTAN®, STALEVO®) or tolcapone (TASMAR®);

Dopamine receptor agonists such as ropinirole (REQUIP®, REPREVE®, RONIROL®, ADARTEL®), pramipexole (MIRAPEX®, MIRAPEXIN®, SIFROL®), rotigotine (NEUPRO®), piribedil (TRASTAL®, TRIVASTAN®, PRONORAN®), apomorphine (APOKYN®);

Adenosine 2A antagonist such as istradefylline (NOURIAST®);

Anticholinergics like benztropine (COGENTIN®); and

Acetylcholinesterase inhibitors such as donepezil hydrochloride (ARICEPT®, MEMAC®), rivastigmine (EXELON®, NIMVASTID®).

Examples of additional therapeutic agents or classes include, without limitation: antipsychotics (anti-schizophrenia) like paliperidone, bifeprunox, ziprasidone, risperidone, aripiprazole, olanzapine and quietapine; anti-depressant-like norepinephrine reuptake inhibitors, selective serotonin reuptake inhibitors (SSRIs), serotonin and noradrenaline reuptake inhibitors (SNRIs), tertiary or secondary amine tricyclics (amitriptyline, clomipramine, desipramine, imipramine); anti-anxiety like benzodiazepines (alprazolam, clonazepam, diazepam, lorazepam);

Stimulants like methylphenidate, dextroamphetamine, modafinil, atomoxetine, clonidine; and sedative-hypnotic agents like zolpidem, eszopiclone, ramelteon.

The "pharmaceutically acceptable salts" according to the invention include therapeutically active, non-toxic acid or base salt forms which the compounds of formula I are able to form.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, oxalic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The invention also relates to all stereoisomeric forms such as enantiomeric and diastereoisomeric forms of the compounds of formula I or mixtures thereof (including all possible mixtures of stereoisomers). Deuterated variants in any position are comprised as well in formula (I)

With respect to the present invention reference to a compound or compounds is intended to encompass that compound in each of its possible isomeric forms and mixtures thereof, unless the particular isomeric form is referred to specifically.

Compounds according to the present invention may exist in different polymorphic forms. Although not explicitly indicated in the above formula, such forms are intended to be included within the scope of the present invention.

Some of the compounds of formula I may also exist in tautomeric forms. Such forms although not explicitly indicated in the above formula are intended to be included within the scope of the present invention. Examples of tautomers include keto (CH$_2$C=O)⇌enol (CH=CHOH) tautomers or amide (NHC=O)↔hydroxyimine (N=COH) tautomers. Formula (I) and the formulae depicted hereinafter are intended to represent all individual tautomers and all possible mixtures thereof, unless stated or shown otherwise.

The invention also includes within its scope pro-drug forms of the compounds of formula I and its various sub-scopes and sub-groups.

Activity in any of the above-mentioned indications can of course be determined by carrying out suitable clinical trials in a manner known to a person skilled in the relevant art for the particular indication and/or in the design of clinical trials in general.

For treating diseases, compounds of formula I or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula I or a pharmaceutically acceptable salt thereof in combination with a pharmaceutically acceptable diluent or carrier.

To prepare a pharmaceutical composition according to the invention, one or more of the compounds of formula I or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula I in compositions for oral administration is at least 0.5% by weight and can be up to 80% by weight with respect to the total weight of the composition.

In accordance with the invention it has also been found that the compounds of formula I or the pharmaceutically acceptable salts thereof can be administered alone or in combination with other pharmaceutically active ingredients. Non-limiting examples of such additional compounds which can be cited for use in combination with the compounds according to the invention are antivirals, antispastics (e.g. baclofen), antiemetics, antimanic mood stabilizing agents, analgesics (e.g. aspirin, ibuprofen, paracetamol), narcotic analgesics, topical anesthetics, opioid analgesics, lithium salts, antidepressants (e.g. mianserin, fluoxetine, trazodone), tricyclic antidepressants (e.g. imipramine, desipramine), anticonvulsants (e.g. valproic acid, carbamazepine, phenytoin), antipsychotics (e.g. risperidone, haloperidol), neuroleptics, benzodiazepines (e.g. diazepam, clonazepam), phenothiazines (e.g. chlorpromazine), calcium channel blockers, amphetamine, clonidine, lidocaine, mexiletine, capsaicin, caffeine, quetiapine, serotonin antagonists, β-blockers, antiarrhythmics, triptans, ergot derivatives and amantadine.

In compositions for parenteral administration, the quantity of compound of formula I present is at least 0.5% by weight and can be up to 33% by weight with respect to the total weight of the composition. For the preferred parenteral compositions, the dosage unit is in the range 0.5 mg to 3000 mg of compounds of formula I.

The daily dose can fall within a wide range of dosage units of compound of formula I and is generally in the range 0.5 to 3000 mg. However, it should be understood that the specific doses can be adapted to particular cases depending on the individual requirements, at the physician's discretion.

The compounds of formula I according to the invention can be prepared analogously to conventional methods as understood by the person skilled in the art of synthetic organic chemistry.

According to one embodiment, some compounds of general formula I-A may be prepared by reaction of an acid of formula II with an amine of formula III (or a corresponding salt) according to the equation:

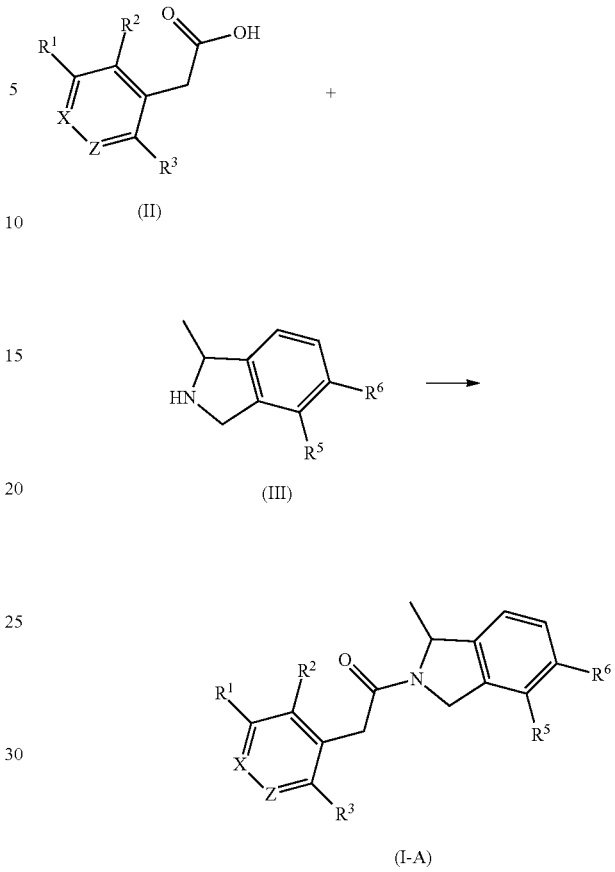

This reaction may be performed in the presence of classical coupling agents such as benzotriazolyl derivatives (BOP and the like) or 1-chloro-N,N-2-trimethylpropenylamine (Ghosez's reagent) or other reagents known by the person skilled in the art, in the presence of a base such as triethylamine or diisopropylethylamine in a solvent such as N,N-dimethylformamide or dichloromethane at a temperature ranging from 20 to 60° C.

Alternatively, some compounds of general formula I-A may be prepared by reaction of a dibromovinyl derivative of formula IV with an amine of formula III (or a corresponding salt) according to the equation:

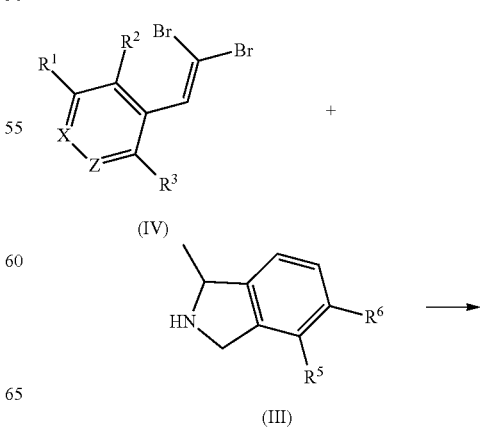

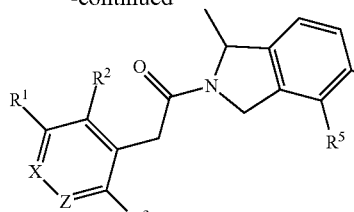

(I-A)

This reaction may be performed in the presence of a base such as potassium hydroxide in a polar solvent mixture such as tetrahydrofuran and water at 0° C. followed by the addition of an acid such as hydrochloric acid at 0° C.

Dibromovinyl derivatives of formula IV may be prepared by olefination of aldehydes of formula IV' using Corey-Fuchs reagent (carbon tetrabromide-triphenylphosphine) or according to any method known to the person skilled in the art.

Compounds of formula IV' are commercially available or may be prepared according to any procedure known to the person skilled in the art.

Alternatively, some compounds of general formula I-A may be prepared by reaction of an amide of formula V with a dibromo derivative of formula VI according to the equation:

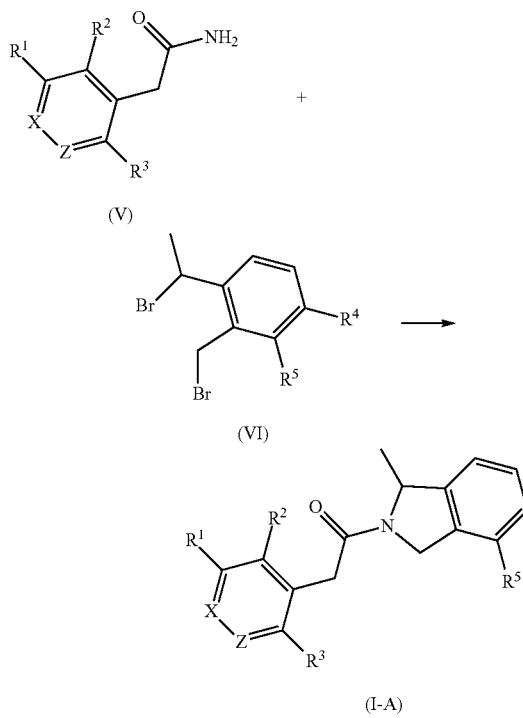

This reaction may be performed in the presence of a base such as sodium hydride in a polar solvent such as N,N-dimethylformamide at room temperature.

Amides V are either commercially available or may be prepared according to any method known to the person skilled in the art.

Dibromo derivatives VI may be prepared by dibromination of a derivative of formula VII according to the equation:

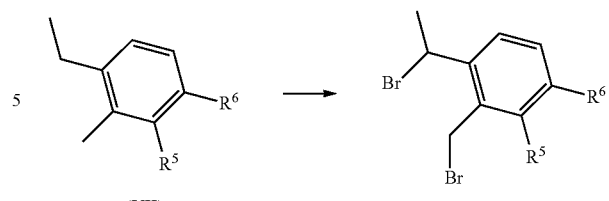

This reaction may be performed using a bromine source such as N-bromosuccinimide (NBS) in the presence of a radical initiator such as benzoyl peroxide in a perchlorinated solvent such as carbon tetrachloride at a temperature ranging from 70 to 90° C.

Derivatives of formula VII are either commercially available or may be prepared according to any method known to the person skilled in the art.

Alternatively, some compounds of formula VI may be prepared by dibromination of diol of formula VIII according to the equation:

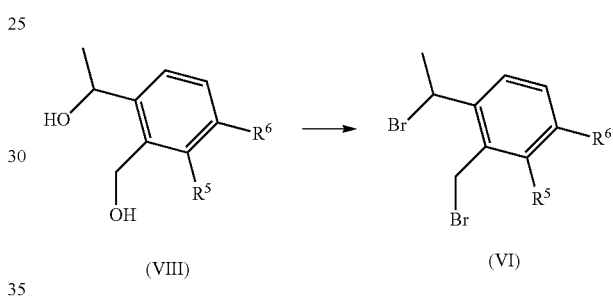

This reaction may be performed in the presence of a brominating agent such as phosphorus tribromide in a solvent such as dichloromethane at room temperature or according to any method known to the person skilled in the art.

Derivatives of formula VIII may be prepared by reduction of lactones of formula IX according to the equation:

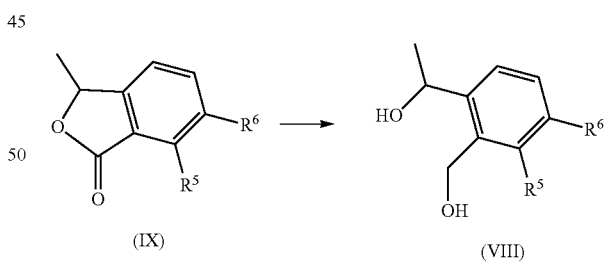

This reaction may be performed in the presence of a reducing agent such as lithium borohydride in a polar solvent such as tetrahydrofuran at 0° C. or according to any method known to the person skilled in the art.

Derivatives of formula IX are either commercially available or may be prepared according to any method known to the person skilled in the art.

According to another embodiment, some compounds of general formula I-B may be prepared by reaction of an isocyanate of formula X with an amine of formula III (or a corresponding salt) according to the equation:

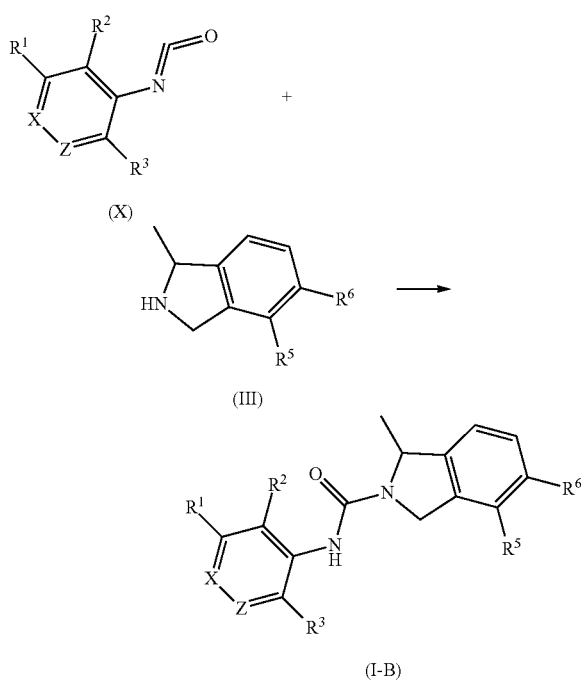

This reaction may be performed in the presence of a base such as triethylamine in a polar solvent such as tetrahydrofuran at 60° C.

Alternatively, some compounds of formula I-B may be prepared by reaction of an acid of formula XI with an amine of formula III (or a corresponding salt) according to the equation:

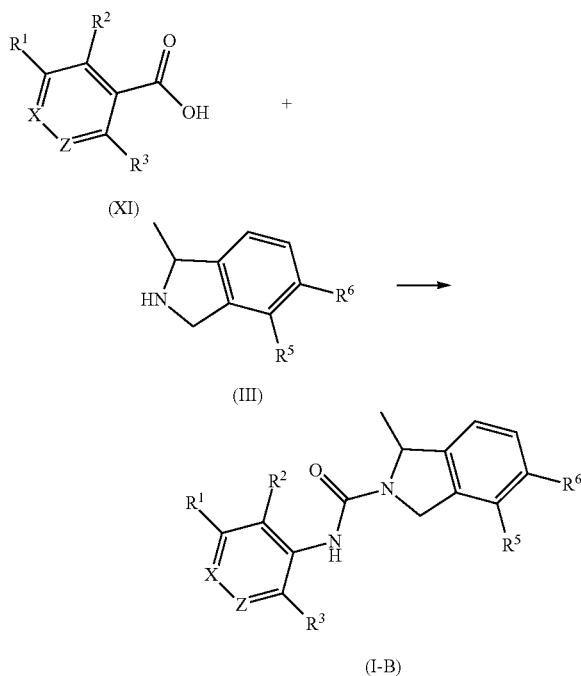

This reaction may be performed in the presence of diphenylphosphoryl azide and triethylamine in an aprotic solvent such as toluene at high temperature such as 120° C.

Alternatively, some compounds having the general formula I may be prepared by functional group conversion on already assembled analogs of compounds having the general formula I, using procedures described in the literature or known to the person skilled in the art.

In particular, compounds of formula I wherein $R^5$ is ($C_{1-6}$-alkylsulfonyl)amino group may be prepared starting from an intermediate of formula XII wherein $R^5$ is an halogen, preferentially bromine or iodine, with ($C_{1-6}$-alkyl)sulfonamide in the presence of a copper salt such as copper iodide and a diamine such as 1,2-diaminocyclohexane in the presence of a base such as potassium phosphate in a polar solvent such as N,N-dimethylformamide at high temperature such as 140° C.

Alternatively, compounds of formula I wherein $R^5$ is alkoxycarbonyl may be prepared by carbonylation of intermediate of formula XII wherein $R^5$ is an halogen, preferentially bromine or iodine, with gaseous carbon monoxide in an autoclave under pressure, in the presence of a palladium salt as a catalyst and a base such as diisopropylethylamine in a polar solvent and an alcohol at a temperature ranging from 70 to 90° C.

Alternatively, compounds of formula I wherein $R^5$ is hydroxy may be prepared by reaction of a compound of formula I wherein $R^5$ is $NH_2$. This reaction may be performed in the presence of potassium bromide and sodium nitrite in water at room temperature or according to any method known to the person skilled in the art.

Compound of formula I wherein $R^5$ is $NH_2$ may be prepared by reduction of compound of formula I wherein $R^5$ is a nitro group according to any method known to the person skilled in the art.

Alternatively, compounds of formula I wherein $R^5$ is acylamino may be prepared starting from a compound of formula I wherein $R^5$ is an amino group according to methods known to the person skilled in the art.

Alternatively, compounds I wherein $R^5$ is —$(CH_2)_n$—$NHR^{5a}$, n=1 and $R^{5a}$ is methylsulfonyl, may be prepared starting from compounds XIII wherein $R^5$ is —$(CH_2)$—$NH_2$ according to any procedure known by the person skilled in the art. Compound XIII wherein $R^5$ is —$(CH_2)$—$NH_2$ may be prepared according to any method known to the person skilled in the art starting from an intermediate XIV wherein $R^5$ is a cyano using a reducing agent such as Raney®-Nickel under hydrogen pressure. Intermediate XIV may be prepared starting from an intermediate XII wherein $R^5$ is a halogen atom, preferentially bromine or iodine using a source of cyanide such as zinc cyanide in the presence of a palladium salt as catalyst at high temperature.

Alternatively, compounds of formula I wherein $R^5$ is —$CONR^{5b}R^{5c}$ may be prepared by coupling starting from an intermediate XV wherein $R^5$ is a carboxylic acid. Intermediate XV may be prepared starting from a compound of formula I wherein $R^5$ is alkoxycarbonyl according to methods known to the person skilled in the art.

Alternatively, compounds of formula I wherein $R^5$ is an optionally substituted alkoxy group may be prepared starting from compounds of formula I wherein $R^5$ is hydroxy according to methods known to the person skilled in the art.

Alternatively, compounds of formula I wherein $R^5$ is an optionally substituted aminosulfonyl group may be prepared by substitution of a chlorosulfonyl intermediate of formula XVI with amine derivatives. Intermediate of formula XVI may be prepared starting from a compound a formula I wherein $R^5$ is an amino group by treatment with sodium nitrite in hydrochloric acid at low temperature followed by the addition of thionyl chloride and copper chloride in water or according to any other method known to the person skilled in the art.

Alternatively, compounds of formula I wherein $R^5$ is a $C_{1-4}$ alkyl group substituted by hydroxyl or (methoxycarbonyl)oxy may be prepared starting from a compound of formula I wherein $R^5$ is alkoxycarbonyl according to methods known to the person skilled in the art.

Alternatively, compounds of formula I wherein $R^5$ is $-SO_2R^{5d}$ and $R^{5d}$ is an optionally substituted alkyl group may be prepared by reaction of an intermediate XVII wherein $R^5$ is a sodium sulfinate salt with an alkyl iodide in a polar solvent such as dimethylsulfoxide. Intermediate XVII wherein $R^5$ is a sodium sulfinate salt may be prepared by coupling from intermediate XII wherein $R^5$ is a halogen atom, preferentially iodine or bromine, in the presence of sodium metabisulfite, tetrabutylammonium bromide, a palladium salt, preferably palladium (II) acetate, 1,10-phenanthroline and triphenylphosphine in a polar solvent such as tetrahydrofuran.

Alternatively, compounds of formula I wherein $R^5$ is $-SO_2R^{5d}$ and $R^{5d}$ is a $C_{1-4}$ alkyl may be prepared by oxidation of an intermediate XVIII wherein $R^5$ is $SR^{5d}$, $R^{5d}$ having the same definition as above according to any method known to the person skilled in the art. Intermediate XVIII wherein $R^5$ is $SR^{5d}$ may be prepared starting from an intermediate XII wherein $R^5$ is a halogen atom, preferentially bromine or iodine according to methods known to the person skilled in the art.

Alternatively, compounds of formula I wherein $R^1$ is an (alkyl)sulfonylaminomethyl may be prepared starting from a compound of formula I wherein $R^1$ is an hydroxymethyl by successive treatment with a chlorinating agent followed by substitution with alkylsulfonamide in the presence of a base such as sodium hydride in a polar solvent such as N,N-dimethylformamide at room temperature or according to any method known to the person skilled in the art.

Compounds of formula I wherein $R^1$ or $R^2$ is hydroxymethyl may be prepared starting from a compound of formula I wherein $R^1$ or $R^2$ is alkoxycarbonyl according to any method known to the person skilled in the art.

Alternatively, compounds of formula I wherein $R^5$ is an heterocycle such as 1H-pyrazol-4-yl may be prepared by a Suzuki-type coupling from intermediate XII wherein $R^2$ is a halogen atom, preferably bromine or iodine, in the presence of the corresponding boronic acid and a palladium salt such as tetrakis(triphenylphosphine)palladium(0) according to methods known to the person skilled in the art.

Alternatively, compounds of formula I wherein $R^5$ is a sulfoximine group such as [dimethyl(oxido)sulfanylidene]amino may be prepared by coupling from intermediate XII wherein $R^2$ is a halogen atom, preferably iodine, in the presence of a base such as cesium carbonate and a palladium salt such as palladium (II) acetate and a bulky phosphine ligand such as 2,2'-bis(diphenylphosphino)-1,1'-binaphthyl according to methods known to the person skilled in the art.

Alternatively, compounds of formula I wherein $R^5$ is a $C_{1-4}$ alkyl group such as 2,2,2-trifluoro-1-hydroxyethyl may be prepared starting from an intermediate XXII wherein $R^5$ is an aldehyde using (trifluoromethyl)trimethylsilane in the presence of a fluoride weak base such as cesium fluoride in a polar solvent such as N,N-dimethylformamide at a high temperature such as 75° C.; or by any method known to the person skilled in the art. Intermediate XXII wherein $R^5$ is an aldehyde may be prepared by carbonylation of an intermediate XII wherein $R^5$ is a halogen atom, preferably bromine or iodine, using a carbon monoxide source such as Syngas in the presence of a palladium salt such as palladium (II) acetate, a diamine such as TMEDA and a bulky diphosphine according to methods known from the person skilled in the art.

Acids of formula II may be prepared by functional group conversion using procedures described in the literature or known to the person skilled in the art. In particular, they may be prepared by hydrolysis of the corresponding cyanides of formula XIX or alkyl esters of formula XX. Cyanides or alkyl esters may be prepared according to classical procedures described in the literature or known to the person skilled in the art.

Amines of formula III are either commercially available or may be prepared according to any method known to the person skilled in the art.

In particular, amines of formula III may be prepared by deprotection of a tert-butylsulfinyl intermediate XXI according to the equation:

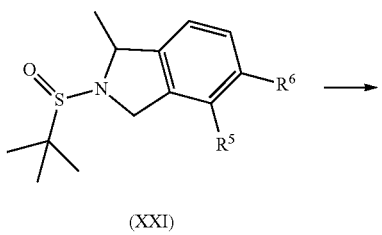

(XXI)

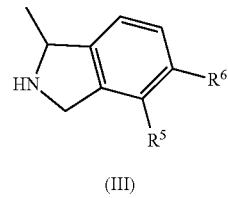

(III)

This reaction may be performed in the presence of an acid such as hydrochloric acid in a protic solvent such as ethanol at room temperature.

Intermediates of formula XXI may be prepared by cyclization of an intermediate of formula VI according to the equation:

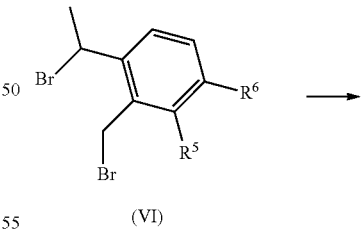

(VI)

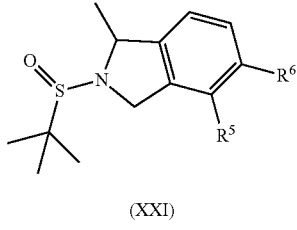

(XXI)

This reaction may be performed in the presence of tert-butylsulfinamide in the presence of a base such as sodium hydride in a polar solvent such as N,N-dimethylformamide at a temperature ranging from 0 to 10° C.

EXAMPLES

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

All reactions involving air- or moisture-sensitive reagents were performed under a nitrogen or argon atmosphere using dried solvents and glassware. Experiments requiring microwave irradiation are performed on a Biotage Initiator Sixty microwave oven upgraded with version 2.0 of the operating software. Experiments are run to reach the required temperature as quickly as possible (maximum irradiation power: 400 W, no external cooling). Commercial solvents and reagents were generally used without further purification, including anhydrous solvents when appropriate (generally Sure-Seal™ products from Aldrich Chemical Company or AcroSeal™ from ACROS Organics). In general reactions were followed by thin layer chromatography, HPLC or mass spectrometry analyses.

HPLC analyses are performed using an Agilent 1100 series HPLC system mounted with a Waters XBridge MS C18, 5 pm, 150×4.6 mm column. The gradient runs from 100% solvent A (water/ACN/ammonium formate solution 85/5/10 (v/v/v)) to 100% solvent B (water/ACN/ammonium formate solution 5/85/10 (v/v/v)) in 6 min. with a hold at 100% B of 5 minutes. The flow rate is set at 8 mL/min during 6 min. then increased at 3 mL/min during 2 min. with a hold at 3 mL/min during 3 minutes. A split of 1/25 is used just before API source. The chromatography is carried out at 45° C. The ammonium formate solution (pH~8.5) is prepared by dissolution of ammonium formate (630 mg) in water (1 L) and addition of ammonium hydroxide 30% (500 µL).

Mass spectrometric measurements in LC-MS mode are performed as follows:
for acidic elution, analyses are performed using:
Method A=A QDA Waters simple quadrupole mass spectrometer is used for LC-MS analysis. This spectrometer is equipped with an ESI source and an UPLC Acquity Hclass with diode array detector (210 to 400 nm). Data are acquired in a full MS scan from m/z 50 to 1000 in positive mode with an acidic elution. The reverse phase separation is carried out at 45° C. on a Waters Acquity UPLC HSS T3 1.8 µm (2.1×50 mm) column for acidic elution. Gradient elution is done with Water (solvent A), ACN (solvent B), Water/ACN/Formic Acid 0.5% (solvent C). HPLC flow rate: 0.6 ml/min to 0.7 mL/min, injection volume: 1 µL. Full flow in MS.
Method B=A SQD Waters single quadrupole mass spectrometer is used for LC-MS analysis. This spectrometer is equipped with an ESI source and an UPLC Waters with diode array detector (210 to 400 nm)
MS parameters: ESI capillary voltage 3.0 kV. Cone and Extractor voltage 25 and 2 V, respectively. Source block temperature 130° C. Desolvation temperature 370° C. Cone gaz flow 120 L/h (Nitrogen), Desolvation Gas flow 800 L/h. Multiplier voltage 470 V. Data are acquired in a full MS scan from m/z 50 to 750 in positive and negative mode.

LC parameters: The reverse phase separation is carried out at 45° C. on an Acquity UPLC HSS T3 C18 column (1.7 µm, 2.1×100 mm). Gradient elution is done with Formic Acid 0.5 mL/L in ACN/water 5/95 (pH~3) (solvent A1), Formic Acid 0.375 mL/L ACN (solvent B1). HPLC flow rate: 0.4 mL/min to 0.5 mL/min, injection volume: 0.4 µL. Full flow in MS.

For Basic Elution, Analyses are Performed Using:
Method C=A QM Waters triple quadrupole mass spectrometer is used for LC-MS analysis. This spectrometer is equipped with an ESI source and an HPLC Waters 2795 quaternary pump with diode array detector (210 to 400 nm).
MS parameters: ESI capillary voltage 2.8 kV, Cone and Extractor voltage 30 and 2 V, respectively, Source block temperature 120° C., Desolvation temperature 320° C., Cone gaz flow 120 L/h (Nitrogen), Desolvation Gas flow 550 L/h. Multiplier voltage 600 V. Data are acquired in a full MS scan from m/z 50 to 750 in positive mode with an acidic elution and both in positive and negative modes with a basic elution.

LC parameters: The reverse phase separation is carried out at 45° C. on a Waters XBridge MS C18 column (3.5 µm, 100×4.6 mm) for basic elution. Gradient elution is done with Water (solvent A), ACN (solvent B), Ammonium Formate in water 630 mg/L+500 µL/L NH$_4$OH 30% (solvent D) (pH~8.5). HPLC flow rate: 8 ml/min to 3 mL/min, injection volume: 5 µL. The splitting ratio is set at +/−150 µL to MS.

GC-MS (100-250° C., 75° C./min, He, EI-positive)

Some reaction mixtures could be treated using Isolute separator phase cartridges (from Biotage) or catch and release SPE (Solid Phase Extraction) cartridges. Crude materials could be purified by normal phase chromatography, (acidic or basic) reverse phase chromatography, chiral separation or recrystallization.

Normal phase chromatography are performed using silica gel columns (100:200 mesh silica gel or Puriflash®-50SIHC-JP columns from Interchim).

Preparative reverse phase chromatography are performed as follows:
LC-MS purification (Basic mode, LC-MS prep) using a SQD or QM Waters triple quadrupole mass spectrometer is used for LC-MS purification. This spectrometer is equipped with an ESI source and a Prep LC controller Waters quaternary pump with diode array detector (210 to 400 nm).
MS parameters: ESI capillary voltage 3 kV. Cone and Extractor voltage 10. Source block temperature 120° C. Desolvation temperature 300° C. Cone gaz flow 30 L/h (Nitrogen), Desolvation Gas flow 650 L/h. Data are acquired in a full MS scan from m/z 100 to 700 in positive mode with an acidic or a basic elution.

LC parameters: The reverse phase separation is carried out at rt on a Sunfire prep OBD C18 column (5 µm, 30×50 mm) for acidic elution a XBridge prep OBD C18 column (5 µm, 30×50 mm) for basic elution. Gradient elution is done with Water (solvent A), ACN (solvent B), Water/ACN/TFA: 49.5/49.5/1, v/v/v (solvent C) (pH~1), Ammonium bicarbonate in water 8 g/L+500 µL/L NH$_4$OH 30% (solvent D) (pH~8.5). HPLC flow rate: 35 mL/min to 60 mL/min, injection volume: 1 mL. The splitting ratio is set at +/−1/6000 to MS.

Standard acidic or basic reverse phase chromatography (Acidic or Basic mode, standard LC) is carried out at rt on a Kromasil C18 column (10 µm, 8×19 cm) for acidic or neutral elution and a Kromasil Eternity or Eternity XT column (10 µm, 8×14 cm) for basic elution. Gradient elution is done with Water (solvent A), ACN (solvent B), Water/TFA: 98/2 v/v (pH~1) OR: water/NH$_4$OH 99.5/0.5 v/v (pH~10) (solvent C).

Acidic "40-70" Gradient Program

| Time (min) | A (%) | B (%) | C (%) | Flow (mL/min) |
|---|---|---|---|---|
| 0 | 55 | 40 | 5 | 180 |
| 4 | 55 | 40 | 5 | 180 |
| 14 | 25 | 70 | 5 | 180 |
| 14.2 | 0 | 95 | 5 | 180 |
| 20 | 0 | 95 | 5 | 180 |
| 20.1 | 55 | 40 | 5 | 180 |
| 25 | 55 | 40 | 5 | 180 |

Basic "20-50" Gradient Program

| Time (min) | A (%) | B (%) | C (%) | Flow (mL/min) |
|---|---|---|---|---|
| 0 | 75 | 20 | 5 | 180 |
| 4 | 75 | 20 | 5 | 180 |
| 14 | 45 | 50 | 5 | 180 |
| 14.2 | 0 | 95 | 5 | 180 |
| 20 | 0 | 95 | 5 | 180 |
| 20.1 | 75 | 20 | 5 | 180 |
| 25 | 75 | 20 | 5 | 180 |

It will be apparent to the one skilled in the art that different retention times (RT) may be obtained for LC-MS data may be obtained if different analytical conditions are used.

Preparative Chiral Chromatographic separations are performed on using liquid phase chromatography or supercritical fluid chromatography (SFC) instruments with various mixtures of lower alcohols and C5 to C8 linear, branched or cyclic alkanes at 360 mL/min. Solvent mixtures as well as columns are described in individual procedures.

Products were generally dried under vacuum before final analyses and submission to biological testing.

NMR spectra are recorded on a BRUKER AVANCE 400 MHz NMR Spectrometer fitted with a Linux workstation running XWIN NMR 3.5 software and a 5 mm inverse $^1$H/BB probehead, or BRUKER DRX 400 NMR fitted with a SG Fuel running XWIN NMR 2.6 software and a 5 mm inverse geometry $^1$H/$^{13}$C/$^{19}$F triple probehead. The compound is studied in d$_6$-dimethylsulfoxide (or d$_3$-chloroform) solution at a probe temperature of 300 K and at a concentration of 10 mg/mL. The instrument is locked on the deuterium signal of d$_6$-dimethylsulfoxide (or d$_3$-chloroform). Chemical shifts are given in ppm downfield from TMS (tetramethylsilane) taken as internal standard.

Abbreviations

ACN: Acetonitrile
AcOH: Acetic acid
BINAP: (2,2'-bis(diphenylphosphino)-1,1'-binaphthyl
BOP: (Benzotriazol-1-yloxy)tris(dimethylamino)phosphonium hexafluorophosphate
tBuONO: tert-butyl nitrite
DCM: Dichloromethane
DIPEA: Diisopropylethylamine
DMAP: 4-(Dimethylamino)pyridine
DMF: N,N-Dimethylformamide
DMSO: Dimethylsulfoxide
ES$^+$: Electrospray Positive Ionisation
EtOH: Ethanol
Et$_2$O: Diethyl ether
EtOAc: Ethyl acetate
h: Hour
HCl: Hydrochloric acid
K$_2$CO$_3$: Potassium carbonate
LC: Liquid Chromatography
LCMS: Liquid Chromatography Mass Spectrometry
MeOH: Methanol
MgSO$_4$: Magnesium sulfate
min.: minutes
NaOH: Sodium hydroxide
Na$_2$SO$_4$: Sodium sulfate
NBS: N-bromosuccinimide
NMR: Nuclear magnetic resonance
PdCl$_2$(dppf): [1,1'-Bis(diphenylphosphino)ferrocene]dichloropalladium(II)
Pd$_2$(dba)$_3$: Tris(dibenzylideneacetone)dipalladium(0)
iPrOH: isopropanol
PTSA: ptoluenesulfonic acid
rt: room temperature
TEA: Triethyl amine
TFA: Trifluoroacetic acid
THF: Tetrahydrofuran
TLC: Thin Layer Chromatography
cAMP: cyclic adenosinemonophosphate
EC$_{20/50}$: concentration which produces 20%/50% of the maximum response
Erel: relative efficacy
HEPES: 4-(2-hydroxyethyl)-1-piperazineethanesulfonic acid
HTRF: homogenous time-resolved fluoresence
IBMX: 3-Isobutyl-1-methylxanthine Intermediates A. Synthesis of Acids of Formula II.

A.1. Synthesis of (3,5-dichloro-2-methylpyridin-4-yl)acetic acid a3

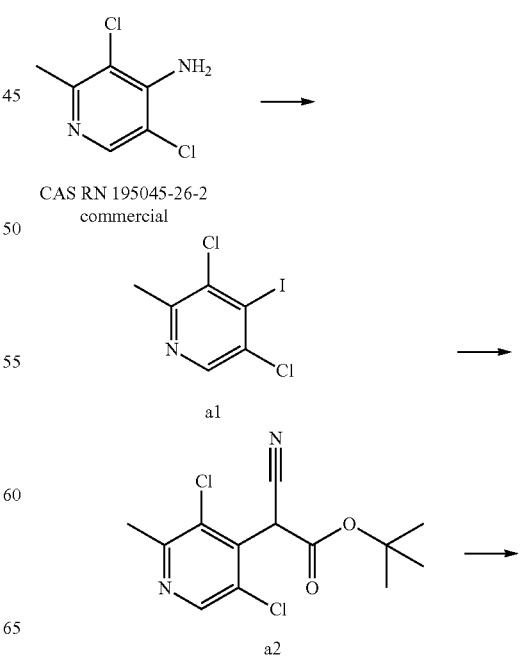

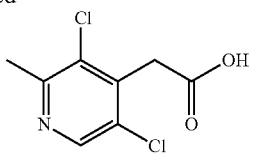

a3

A.1.1. Synthesis of 3,5-dichloro-4-iodo-2-methylpyridine a1

To a solution of CuI (4.3 g, 22.7 mmol) in ACN (100 mL) at 50° C. was added tBuONO (6.8 mL, 56.8 mmol) and the mixture was stirred at the same temperature for 30 min. 3,5-Dichloro-2-methylpyridin-4-amine (commercial, 2 g, 11.4 mmol) was added at 50° C. and the reaction mixture was heated from 50° C. to 80° C. for 30 min. The reaction mixture was concentrated under reduced pressure and extracted with EtOAc. The organic layer was washed with water, dried over $Na_2SO_4$, filtered and concentrated under reduced pressure. The residue was purified by column chromatography using 10% EtOAc in hexanes as eluent to afford 22 g of 3,5-dichloro-4-iodo-2-methylpyridine a1.

Yield: 68%.

$^1$H NMR (400 MHz, $CD_3OD$) δ 7.98 (s, 1H), 2.46 (s, 3H).

A.1.2. Synthesis of tert-butyl cyano(3,5-dichloro-2-methylpyridin-4-yl)acetate a2

To a solution of 3,5-dichloro-4-iodo-2-methylpyridine a1 (2 g, 6.9 mmol) in DMF (64 mL) were added tert-butyl 2-cyanoacetate (1.9 mL, 13.9 mmol), CuI (0.39 g, 2.07 mmol) and $K_2CO_3$ (3.8 g, 27.6 mmol). The mixture was heated at 120° C. for 12 h, then concentrated under reduced pressure. The residue was diluted with water and the aqueous layer was extracted in EtOAc. The organic layer was dried over $Na_2SO_4$, filtered and concentrated under reduced pressure. The residue was purified by column chromatography using 15% EtOAc in hexanes as eluent to afford 1.38 g of tert-butyl cyano(3,5-dichloro-2-methylpyridin-4-yl)acetate a2.

Yield: 66%.

LCMS: 301 (M+H)$^+$.

A.1.3. Synthesis of (3,5-dichloro-2-methylpyridin-4-yl)acetic acid a3

A solution of tert-butyl cyano(3,5-dichloro-2-methylpyridin-4-yl)acetate a2 (1.9 g, 6.33 mmol) in a 6N aqueous solution of HCl (20 mL) was heated at 95° C. for 12 h. The reaction mixture was concentrated under reduced pressure. The residue was diluted with water and the aqueous layer was extracted with EtOAc. The organic layer was dried over $Na_2SO_4$, filtered and concentrated under reduced pressure. The residue was purified by column chromatography using 5% MeOH in DCM as eluent to afford 0.7 g of (3,5-dichloro-2-methylpyridin-4-yl)acetic acid a3.

Yield: 52%.

$^1$H NMR (400 MHz, $CD_3OD$) δ 8.40 (s, 1H), 4.05 (s, 2H), 2.54-2.75 (m, 3H).

A.2. Synthesis of (3-bromo-5-chloropyridin-4-yl)acetic acid a9

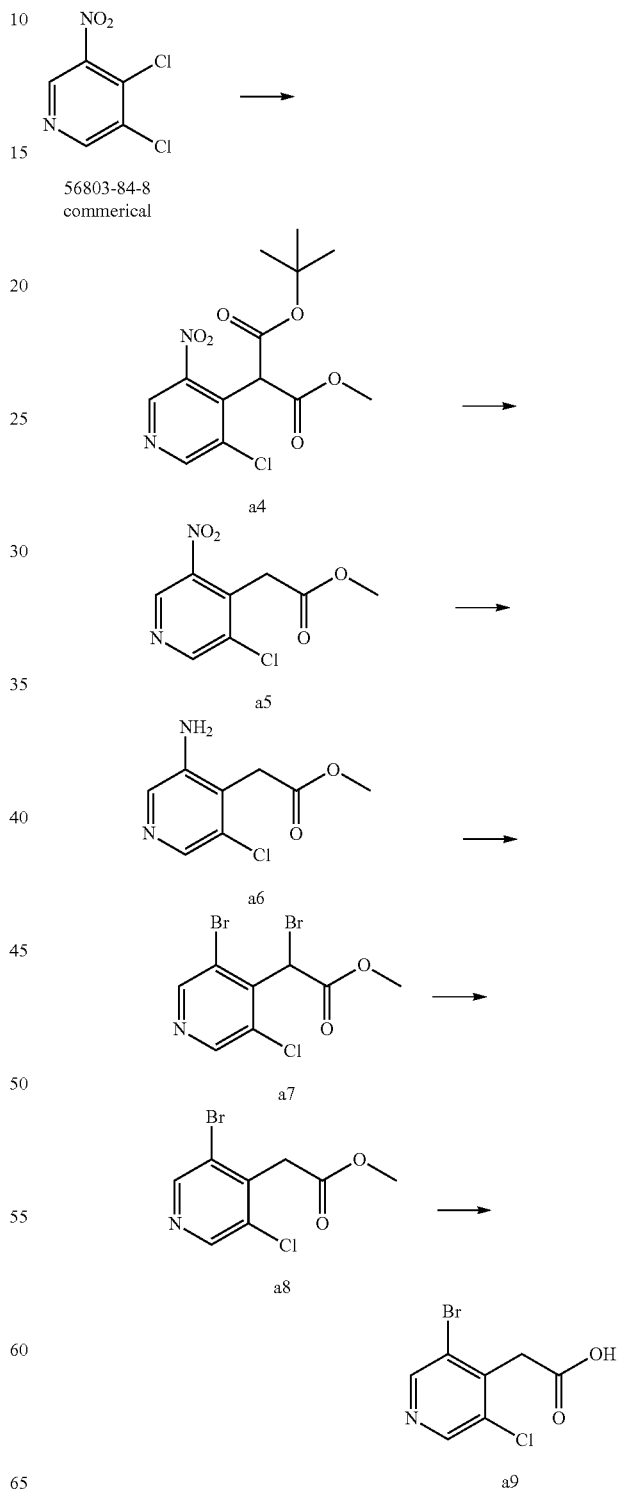

A.2.1. Synthesis of tert-butyl methyl (3-chloro-5-nitropyridin-4-yl)propanedioate a4

To a solution of NaH (60% in mineral oil, 1.33 g, 33.42 mmol) in DMF (40 mL) at 0° C. was added dropwise tert-butyl methyl malonate (5.65 mL, 33.42 mmol) in DMF (10 mL). The mixture was stirred at rt for 30 min., then 3,4-dichloro-5-nitropyridine (commercial, 4.3 g, 22.28 mmol) in DMF (10 mL) was added dropwise at 0° C. The reaction mixture was stirred at rt for 6 h, then acidified to pH 3 with a 2N aqueous solution of HCl. The reaction mixture was poured onto ice water and the compound was extracted in Et$_2$O. The organic layer was dried over Na$_2$SO$_4$, filtered and concentrated under reduced pressure. The residue was purified by column chromatography using 20% EtOAc in hexanes to afford 3.83 g of tert-butyl methyl (3-chloro-5-nitropyridin-4-yl)propanedioate a4 as pale yellow solid.

Yield: 52%.
$^1$H NMR (400 MHz, CDCl$_3$) δ 9.15 (s, 1H), 8.88 (s, 1H), 5.37-5.51 (m, 1H), 3.79 (s, 3H), 1.46 (s, 9H).

A.2.2. Synthesis of methyl (3-chloro-5-nitropyridin-4-yl)acetate a5

TFA (27 mL) was added at rt to a solution of tert-butyl methyl (3-chloro-5-nitropyridin-4-yl)propanedioate a4 (11.5 g, 34.84 mmol) in DCM (200 mL). The reaction mixture was refluxed for 2 h and concentrated under reduced pressure. The residue was dissolved in DCM and washed with an aqueous saturated solution of sodium bicarbonate. The organic layer was dried over Na$_2$SO$_4$, filtered and concentrated under vacuum to afford 7.9 g of crude methyl (3-chloro-5-nitropyridin-4-yl)acetate a5 which was used in next step without any further purification.

Yield: 98% (crude).
$^1$H NMR (400 MHz, CDCl$_3$) δ 9.09-9.21 (m, 1H), 8.74-8.98 (m, 1H), 4.25 (s, 2H), 3.64-3.83 (m, 3H).

A.2.3. Synthesis of methyl (3-amino-5-chloropyridin-4-yl)acetate a6

To a solution of methyl (3-chloro-5-nitropyridin-4-yl)acetate a5 (1 g, 4.33 mmol) in MeOH (125 mL) were added iron powder (3.63 g, 65 mmol) and ammonium chloride (3.47 g, 65 mmol). The reaction mixture was refluxed for 16 h, filtered through Celite® and the filtrate was concentrated under reduced pressure. The residue was dissolved in water and the compound was extracted in EtOAc. The organic layer was dried over Na$_2$SO$_4$, filtered and concentrated under vacuum. The residue was purified by column chromatography using 5% MeOH in DCM as eluent to afford 0.53 g of methyl (3-amino-5-chloropyridin-4-yl)acetate a6 as a white solid.

Yield: 61%.
LCMS: 201 (M+H)$^+$.
$^1$H NMR (400 MHz, DMSO-d$_6$) δ 7.91 (s, 1H), 7.76 (s, 1H), 3.75 (s, 2H), 3.62 (s, 3H).

A.2.4. Synthesis of methyl bromo(3-bromo-5-chloropyridin-4-yl)acetate a7

To a solution of CuBr$_2$ (1.11 g, 4.98 mmol) in ACN (15 mL) at 50° C. was added tBuONO (1.5 mL, 12.45 mmol) and the mixture was stirred at 80° C. for 30 min. Methyl (3-amino-5-chloropyridin-4-yl)acetate a6 (0.5 g, 2.49 mmol) as a solid compound was added and the reaction mixture was further refluxed for 1 h. The reaction mixture was warmed to rt, diluted with EtOAc and filtered through Celite®. The filtrate was concentrated under reduced pressure. The residue was taken up with EtOAc and washed with an aqueous saturated solution of sodium bicarbonate. The organic layer was dried over Na$_2$SO$_4$, filtered and concentrated under vacuum. The residue was purified by column chromatography to afford 0.57 g of methyl bromo(3-bromo-5-chloropyridin-4-yl)acetate a7 as a sticky solid.

Yield: 68%.
LCMS: 344 (M+H)$^+$.

A.2.5. Synthesis of methyl (3-bromo-5-chloropyridin-4-yl)acetate a8

To a solution of methyl bromo(3-bromo-5-chloropyridin-4-yl)acetate a7 (2.1 g, 6.11 mmol) in MeOH (50 mL) were added dropwise at rt indium metal (1.75 g, 15.28 mmol) and AcOH (3.5 mL, 61.11 mmol). The mixture was stirred at rt for 12 h and concentrated under reduced pressure. The residue was diluted with EtOAc and washed with an aqueous saturated solution of sodium bicarbonate. The organic layer was dried over Na$_2$SO$_4$, filtered and concentrated under vacuum to afford 1.6 g of crude methyl (3-bromo-5-chloropyridin-4-yl)acetate a8 as pale yellow oil which was used in next step without any further purification.

Yield: 99% (crude).
$^1$H NMR (400 MHz, DMSO-d$_6$) δ 8.75 (s, 1H), 8.67 (s, 1H), 4.06 (s, 2H), 3.62-3.72 (m, 3H).

A.2.6. Synthesis of (3-bromo-5-chloropyridin-4-yl)acetic acid a9

To a solution of methyl (3-bromo-5-chloropyridin-4-yl)acetate a8 (1.6 g, 6.04 mmol) in MeOH (50 mL) at 0° C. was added a solution of NaOH (1 g, 24.2 mmol) in water (15 mL).

The mixture was stirred at rt for 3 h, then quenched with ammonium chloride (2.66 g) and concentrated under reduced pressure. The residue was taken up with water and the pH was adjusted to 5-6. The compound was extracted with a solution of 5% MeOH in DCM. The organic layer was dried over Na$_2$SO$_4$, filtered and concentrated under vacuum. The residue was purified by column chromatography using 5% MeOH in DCM as eluent to afford 1.1 g of (3-bromo-5-chloropyridin-4-yl)acetic acid a9 as pale yellow solid.

Yield: 73%.
$^1$H NMR (400 MHz, DMSO-d$_6$) δ 12.98 (bs, 1H), 8.73 (s, 1H), 8.59-8.68 (m, 1H), 3.95 (s, 2H).

A.3. Synthesis of (5-chloro-1H-pyrrolo[2,3-b]pyridin-4-yl)acetic acid a13

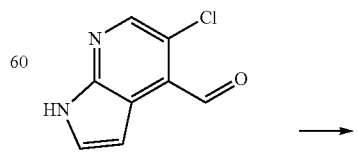

CAS RN 1015610-39-5
commercial

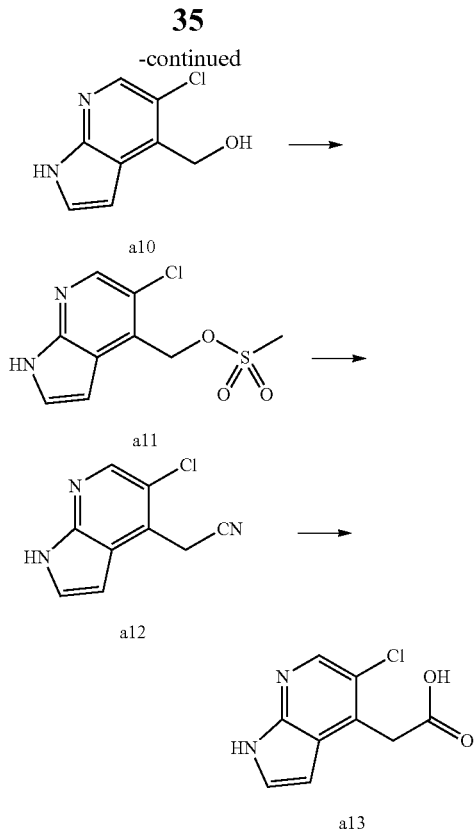

DMSO (9 mL) at rt. Sodium cyanide (255 mg, 5.20 mmol) was added. The mixture was stirred at room temperature for 3 h. The reaction mixture was quenched with an aqueous saturated solution of NaHCO$_3$, then extracted thrice with EtOAc.

The organic layer was washed with brine, dried over Na$_2$SO$_4$, filtered and concentrated under vacuum. The residue was purified by reverse phase chromatography (basic mode, standard LC) to yield 112 mg of (5-chloro-1H-pyrrolo[2,3-b]pyridin-4-yl)acetonitrile a12.

Yield: 22%.
LCMS (ES$^+$) 192/194 (M+H)$^+$.

A.3.4. Synthesis of (5-chloro-1H-pyrrolo[2,3-b]pyridin-4-yl)acetic acid a13

(5-chloro-1H-pyrrolo[2,3-b]pyridin-4-yl)acetonitrile a12 (112 mg, 0.59 mmol) was dissolved in a mixture of water (2 mL) and concentrated sulfuric acid (2 mL). The mixture was stirred at 110° C. for 1 h, then allowed to warm to rt and neutralized with a 1N aqueous solution of NaOH. The reaction mixture was filtered and EtOH was added. The residual solution was filtered again, then concentrated under vacuum to afford 121 mg of (5-chloro-1H-pyrrolo[2,3-b]pyridin-4-yl)acetic acid a13 as an off-white solid which was used in next step without any further purification.

Yield: 98% (crude).
LCMS (ES$^+$) 210/212 (M+H)$^+$.

A.4. Synthesis of (3,5-dichloro-2-methoxypyridin-4-yl)acetic acid a18

A.3.1. Synthesis of (5-chloro-1H-pyrrolo[2,3-b]pyridin-4-yl)methanol a10

5-chloro-1H-pyrrolo[2,3-b]pyridine-4-carbaldehyde (commercial, 450 mg, 2.49 mmol) was dissolved in MeOH (15 mL) and THF (15 mL) at 0° C. Sodium borohydride (189 mg, 4.98 mmol) was added. The mixture was stirred at 0° C. and allowed to warm to rt. The reaction mixture was poured on a catch and release acidic column (5 g). The product was released by an 1M solution of ammonia in MeOH (20 mL) and concentrated under vacuum to afford 474 mg of crude (5-chloro-1H-pyrrolo[2,3-b]pyridin-4-yl)methanol a10 which was used in the next step without any further purification.

Yield: 104% (crude).
LCMS (ES$^+$) 183/185 (M+H)$^+$.

A.3.2. Synthesis of (5-chloro-1H-pyrrolo[2,3-b]pyridin-4-yl)methyl methanesulfonate a11

To a solution of (5-chloro-1H-pyrrolo[2,3-b]pyridin-4-yl)methanol a10 (475 mg, 2.60 mmol) in DCM (27 mL) at 0° C. were added DIPEA (925 µL, 5.20 mmol) and methanesulfonyl chloride (300 µL, 3.90 mmol) were added. The mixture was stirred and allowed to warm to rt. The reaction mixture was concentrated under vacuum to afford 678 mg of crude (5-chloro-1H-pyrrolo[2,3-b]pyridin-4-yl)methyl methanesulfonate a11 as a yellow oil which was used in the next step without any further purification.

A.3.3. Synthesis of (5-chloro-1H-pyrrolo[2,3-b]pyridin-4-yl)acetonitrile a12

Crude (5-chloro-1H-pyrrolo[2,3-b]pyridin-4-yl)methyl methanesulfonate a11 (678 mg, 2.60 mmol) was dissolved in

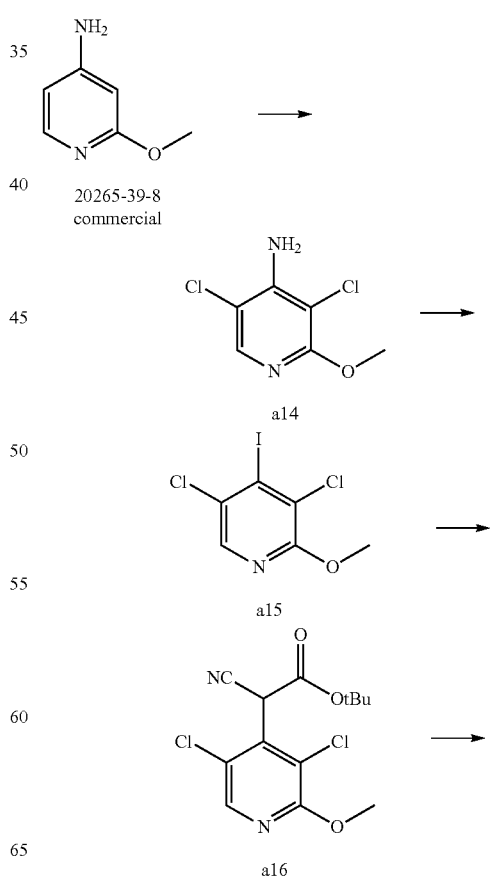

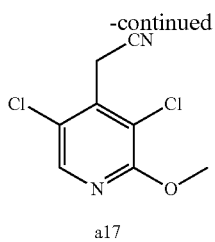

a17

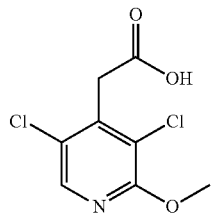

a18

A.4.1. Synthesis of 3,5-dichloro-2-methoxypyridin-4-amine a14

To a solution of 2-methoxypyridin-4-amine (commercial, 30 g, 241.6 mmol) in ACN (1 L) at rt, N-chlorosuccinimide (129 g, 966.6 mmol) was added by portions. The mixture was stirred at rt for 16 h, then concentrated under vacuum and taken up with a 20% aqueous solution of $K_2CO_3$ (500 mL). The compound was extracted with EtOAc. The organic layer was washed with brine, dried over $Na_2SO_4$, filtered and concentrated under vacuum. The residue was purified by column chromatography using 50% EtOAc in hexanes as eluent to afford 35.1 g of 3,5-dichloro-2-methoxypyridin-4-amine a14.

Yield: 75%.

$^1$H NMR (400 MHz, DMSO-$d_6$) δ 7.70-7.91 (m, 1H), 6.50 (s, 2H), 3.80-3.97 (m, 3H).

A.4.2. Synthesis of 3,5-dichloro-4-iodo-2-methoxypyridine a15

To a solution of CuI (59 g, 311 mmol,) in ACN (1 L) was added dropwise at 50° C. t-BuONO (93 mL, 777 mmol). The mixture was heated at 80° C. for 30 min, then a solution of 3,5-dichloro-2-methoxypyridin-4-amine a14 (30 g, 155 mmol) in ACN (500 mL) was added in portions (evolution of nitrogen gas was observed). The reaction mixture stirred at 80° C. for 2 h, then concentrated under vacuum. The residue was taken up with EtOAc (100 mL) and hexane (2 L). The resulting suspension was passed through a short silica bed and the filtrate was concentrated under vacuum to afford 34.9 g of 3,5-dichloro-4-iodo-2-methoxypyridine a15 as a pale yellow solid.

Yield: 74%.

$^1$H NMR (400 MHz, DMSO-$d_6$) δ 8.19-8.34 (m, 1H), 3.87-4.00 (m, 3H).

A.4.3. Synthesis of tert-butyl cyano(3,5-dichloro-2-methoxypyridin-4-yl)acetate a16

To a solution of 3,5-dichloro-4-iodo-2-methoxypyridine a15 (10 g, 32.9 mmol), tert-butyl 2-cyanoacetate (9.4 ml, 65.8 mmol), cesium carbonate (42.9 g, 131.6 mmol) in DMF (160 mL) was added CuI (0.63 g, 3.29 mmol). The reaction mixture was stirred at 100° C. for 3 h, then poured onto ice water and neutralized with a 6N aqueous solution of HCl. The compound was extracted in EtOAc. The organic layer was washed with brine, dried over $Na_2SO_4$, filtered and concentrated under vacuum. The residue was purified by column chromatography using 20% EtOAc in hexanes as eluent to afford 6.7 g of tert-butyl cyano(3,5-dichloro-2-methoxypyridin-4-yl)acetate a16.

Yield: 64%.

$^1$H NMR (400 MHz, DMSO-$d_6$) δ 8.39-8.53 (m, 1H), 6.32 (s, 1H), 3.92-4.07 (m, 3H), 1.42 (s, 9H).

A.4.4. Synthesis of (3,5-dichloro-2-methoxypyridin-4-yl)acetonitrile a17

To a solution of tert-butyl cyano(3,5-dichloro-2-methoxypyridin-4-yl)acetate a16 (20 g, 63.05 mmol) in DCM (500 mL) was added TFA (80 mL) at rt. The reaction mixture was refluxed for 2 h, concentrated under reduced pressure and the residue was neutralized with an aqueous saturated solution of sodium bicarbonate. The compound was extracted in EtOAc. The organic layer was dried over $Na_2SO_4$, filtered and concentrated under vacuum to afford 13.5 g of (3,5-dichloro-2-methoxypyridin-4-yl)acetonitrile a17 as yellow solid which was used in next step without any further purification.

Yield: 98% (crude).

$^1$H NMR (400 MHz, DMSO-$d_6$) δ 8.31-8.47 (m, 1H), 4.19-4.30 (m, 2H), 3.86-4.06 (m, 3H).

A.4.5. Synthesis of (3,5-dichloro-2-methoxypyridin-4-yl)acetic acid a18

A 10N aqueous solution of NaOH (93.5 mL, 933 mmol) was added to a solution of (3,5-dichloro-2-methoxypyridin-4-yl)acetonitrile a17 (13.5 g, 62 mmol) in EtOH (300 mL) and the mixture was refluxed for 12 h. The reaction mixture was diluted with water and ammonium chloride (60 g) was added. The solvent was concentrated under vacuum and the aqueous layer was acidified to pH 5 with a 6N aqueous solution of HCl. The compound was extracted with 5% MeOH in DCM. The organic layer was dried over $Na_2SO_4$, filtered and concentrated under vacuum. The residue was purified by column chromatography using 5% MeOH in DCM as eluent to afford 5 g of (3,5-dichloro-2-methoxypyridin-4-yl)acetic acid a17 as an off-white solid.

Yield: 34%.

$^1$H NMR (400 MHz, $CD_3OD$) δ 8.03-8.18 (m, 1H), 3.99 (d, J=3.02 Hz, 3H), 3.26-3.42 (m, 2H).

A.5. Synthesis of [2,6-dichloro-3-(methoxycarbonyl)phenyl]acetic acid a19

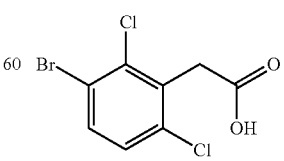

CAS RN 197711-05-0
commercial

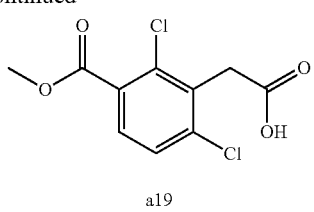

a19

To a solution of (3-bromo-2,6-dichlorophenyl)acetic acid (commercial, 2.3 g, 8.1 mmol) in MeOH (100 mL) were added TEA (1.6 g, 16.24 mmol) and PdCl$_2$(dppf) (0.59 g, 0.81 mmol). The mixture was heated at 120° C. under carbon monoxide atmosphere for 8 h, then concentrated under vacuum. The residue was purified by column chromatography using 40% EtOAc in hexanes as eluent to afford 1.5 g of [2,6-dichloro-3-(methoxycarbonyl)phenyl]acetic acid a19.

Yield: 70%.

$^1$H NMR (400 MHz, DMSO-d$_6$) δ 12.81 (s, 1H), 7.78-7.59 (m, 2H), 3.97 (m, 2H), 3.87 (s, 3H).

A.6. Synthesis of 2-(5-chloro-1H-indol-4-yl)acetic acid a54

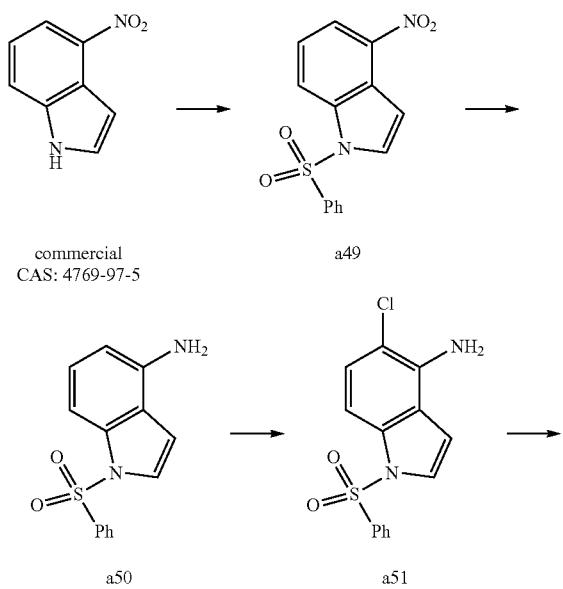

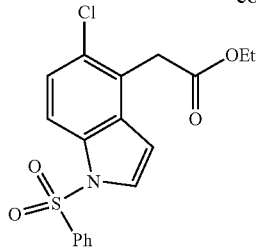

a53

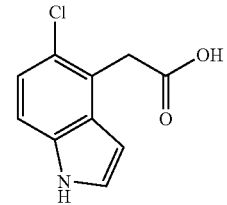

a54

A.6.1. Synthesis of 1-(benzenesulfonyl)-4-nitro-indole a49

To a solution of 4-nitro-1H-indole (25 g, 154.32 mmol) in ACN (250 mL), DIPEA (29.5 mL, 169.75 mmol) was added at rt. The reaction was cooled to 0° C. and benzenesulfonyl chloride (23 mL, 185.18 mmol) was added. The reaction was heated at 80° C. for 3 h. After completion, the reaction was quenched with an aqueous saturated solution of sodium bicarbonate and extracted with EtOAc. The organic layer was separated, washed with water, dried over Na$_2$SO$_4$, filtered and concentrated under vacuum to afford 34.95 g of 1-(benzenesulfonyl)-4-nitro-indole a49.

Yield: 97% (crude).

$^1$H NMR (400 MHz, DMSO-d$_6$) δ 8.47-8.39 (m, 1H), 8.26-8.17 (m, 2H), 8.12-8.04 (m, 2H), 7.78-7.68 (m, 1H), 7.67-7.54 (m, 3H), 7.38-7.26 (m, 1H).

A.6.2. Synthesis of 1-(benzenesulfonyl)indol-4-amine a50

To a stirred solution of 1-(benzenesulfonyl)-4-nitro-indole a49 (25 g, 82.78 mmol) in MeOH (250 mL), Fe (69.53 g, 1241.72 mmol) and NH$_4$Cl (67.05 g, 1241.72 mmol) were added and the reaction mixture was heated to reflux for 15 h. After completion, the reaction was filtered through Celite® and the filtrate was concentrated under reduced pressure. The crude product was purified by column chromatography using 10% EtOAc in n-hexane as eluent to afford 7 g of 1-(benzenesulfonyl)indol-4-amine a50.

Yield: 31%

LCMS (ES$^+$): 273 (M+H)$^+$.

$^1$H NMR (400 MHz, DMSO-d$_6$) δ 7.95-7.85 (m, 2H), 7.72-7.49 (m, 4H), 7.14-6.91 (m, 3H), 6.35 (d, J=7.7 Hz, 1H), 5.55 (s, 2H).

A.6.3. Synthesis of 1-(benzenesulfonyl)-5-chloro-indol-4-amine a51

To a stirred solution of 1-(benzenesulfonyl)indol-4-amine a50 (35.36 g, 130 mmol) in DCM (300 mL) at 0° C., a solution of N-chlorosuccinimide (17.29 g, 130 mmol) in DCM (100 mL) was added. The mixture was stirred at the same temperature for 1 h, then at rt for 1 h. After completion, the reaction mixture was quenched with an aqueous saturated solution of sodium bicarbonate and extracted with DCM. The organic layer was separated, washed with water, dried over Na$_2$SO$_4$, filtered and concentrated under vacuum. The crude product was purified by column chromatography using 10% EtOAc in hexanes as eluent to afford 14.8 g of 1-(benzenesulfonyl)-5-chloro-indol-4-amine a51, Yield: 37%

$^1$H NMR (400 MHz, DMSO-d$_6$) δ 7.95-7.87 (m, 2H), 7.76-7.54 (m, 4H), 7.09 (dd, J=17.3, 3.3 Hz, 3H), 5.82 (s, 2H).

A.6.4. Synthesis of 1-(benzenesulfonyl)-5-chloro-4-iodo-indole a52

To a solution of 1-(benzenesulfonyl)-5-chloro-indol-4-amine a51 (13.8 g, 45.09 mmol) in a 12N aqueous solution of HCl (414 mL) at 0° C., a solution of NaNO$_2$ (7.77 g, 112.74 mmol) in water (70 mL) was added dropwise. The mixture was stirred for 30 min at the same temperature. A solution of KI (74.84 g, 450.9 mmol) in water (137 mL) was then added dropwise at 0° C. and the mixture was stirred at the same temperature for 3 h. After completion, the reaction was extracted with EtOAc. The organic layer was separated, washed with water, dried over Na$_2$SO$_4$, filtered and concentrated under vacuum. The crude product was purified by column chromatography using 10% EtOAc in hexanes as eluent to afford 17.2 g of 1-(benzenesulfonyl)-5-chloro-4-iodo-indole a52.
Yield: 92%
$^1$H NMR (400 MHz, DMSO-d$_6$) δ 8.05-7.85 (m, 4H), 7.77-7.67 (m, 1H), 7.62 (t, J=7.8 Hz, 2H), 7.51 (d, J=8.8 Hz, 1H), 6.70 (d, J=3.7 Hz, 1H).

A.6.5. Synthesis of ethyl 2-[1-(benzenesulfonyl)-5-chloro-indol-4-yl]acetate a53

To a stirred solution of activated zinc (12.23 g, 188.2 mmol) in dry THF (75 mL), chlorotrimethylsilane (2.39 mL, 18.82 mmol) was added. The mixture was stirred at rt for 15 min followed by dropwise addition of ethyl bromo acetate (8.3 mL, 75.41 mmol) at rt. The molarity of Reformatsky reagent was measured by titration method NCI and iodine method). 1-(benzenesulfonyl)-5-chloro-4-iodo-indole a52 (5 g, 11.97 mmol) was dissolved in THF (50 mL) and purged with argon for 15 min. Pd(tBu$_3$P)$_2$ (0.608 g, 1.19 mmol) was added, followed by addition of Reformatsky reagent. The reaction was heated at 65° C. for 16 h. After completion, the reaction mixture was quenched with an aqueous saturated solution of ammonium chloride and extracted with EtOAc. The organic layer was separated, washed with water, dried over Na$_2$SO$_4$, filtered and concentrated under vacuum. The crude product was purified by column chromatography using 10% EtOAc in hexanes as eluent to afford 3.34 g of ethyl 2-[1-(benzenesulfonyl)-5-chloro-indol-4-yl]acetate a53.
Yield: 74%
LCMS (ES$^+$): 378 (M+H)$^+$.
$^1$H NMR (400 MHz, DMSO-d$_6$) δ 8.00 (dd, J=7.8, 1.6 Hz, 2H), 7.94-7.85 (m, 2H), 7.71 (t, J=7.4 Hz, 1H), 7.60 (t, J=7.8 Hz, 2H), 7.41 (d, J=8.8 Hz, 1H), 7.02 (d, J=3.8 Hz, 1H), 4.12 (q, J=7.1 Hz, 2H), 4.02 (s, 2H), 1.14 (t, J=7.1 Hz, 3H).

A.6.6. Synthesis of 2-(5-chloro-1H-indol-4-yl)acetic acid a54

To a stirred solution of ethyl 2-[1-(benzenesulfonyl)-5-chloro-indol-4-yl]acetate a53 (4.547 g, 12.06 mmol) in EtOH (40 mL), a 3N aqueous solution of NaOH (20 mL) was added. The mixture was heated to reflux for 8 h. After completion, the reaction was evaporated under reduced pressure. The residue was diluted with water, acidified to pH 2 using a 1N aqueous solution of HCl and extracted with EtOAc. The organic layer was separated, washed with water, dried over Na$_2$SO$_4$, filtered and concentrated under vacuum to afford 2.5 g of 2-(5-chloro-1H-indol-4-yl)acetic acid a54.
Yield: 99%
$^1$H NMR (400 MHz, DMSO-d$_6$) δ 12.31 (s, 1H), 11.27 (s, 1H), 7.38-7.40 (m, 1H), 7.32 (dd, J=8.6, 0.9 Hz, 1H), 7.10 (d, J=8.6 Hz, 1H), 6.50-6.52 (m, 1H), 3.91 (s, 2H).

B. Synthesis of Amines of Formula III.

B.1. Synthesis of (1S)-1-methyl-2,3-dihydro-1H-isoindole hydrochloride a22

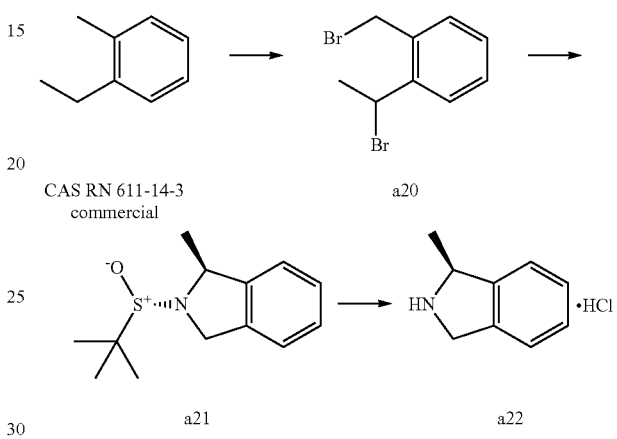

B.1.1. Synthesis of 1-(1-bromoethyl)-2-(bromomethyl)benzene a20

A stirred mixture of 1-ethyl-2-methylbenzene (commercial, 50 g, 416 mmol), N-bromosuccinimide (155 g, 874 mmol) and benzoyl peroxide (6.72 g, 20.80 mmol) in carbon tetrachloride (1.25 L) was heated to reflux. After 2 h, the reaction mixture was allowed to warm to rt, then poured onto an aqueous saturated solution of Na$_2$CO$_3$ (1 L). The organic layer was successively washed with an aqueous saturated solution of Na$_2$CO$_3$ (0.5 L), brine (0.5 L) and dried over Na$_2$SO$_4$, filtered and concentrated under vacuum to obtain 203 g of 1-(1-bromoethyl)-2-(bromomethyl)benzene a20 as a yellow oil which was used in next step without any further purification.
GC-MS (EI-positive): 199/201 [M−Br]$^+$.

B.1.2. Synthesis of tert-butyl-[(1S,2S)-1-methyl-1,3-dihydro-2H-isoindol-2-yl]-oxido-sulfonium a21

1-(1-bromoethyl)-2-(bromomethyl)benzene a20 (203 g, 730 mmol) was dissolved in DMF (2 L). (S)-(−)-tert-butylsulfinamide (97 g, 803 mmol) was added and the mixture was cooled with an ice-water bath and flushed with nitrogen gas. NaH (60% in mineral oil, 64.3 g, 1607 mmol) was added by portions, while the temperature was kept below 10° C. The reaction mixture was stirred for 30 min. at a temperature maintained below 10° C., then carefully quenched with water (2 L). The solution was extracted with Et$_2$O (6×2 L). The organic layer was washed in two batches with water (4×1 L, per batch), brine (1 L, per batch), dried over MgSO$_4$, filtered and concentrated under vacuum to yield 173 g of a red oil. The residue was filtered over silica (1 kg) using from 5 to 50% EtOAc in heptane as eluent. The fractions containing the diastereoisomeric products were collected. This material was purified by column chromatography (1.5 kg silica, by batches of 25 g) using from 3 to 25% EtOAc in heptane as eluent. Final purification by reverse phase chromatography (batches of 3 g, basic mode, standard LC) to afford 45.4 g of tert-butyl-[(1S,2S)-1-methyl-1,3-dihydro-2H-isoindol-2-yl]-oxido-sulfonium a21 as a white solid.

Yield: 26%.

LCMS (ES+): 238 (M+H+).

$^1$H-NMR (300 MHz, CDCl$_3$) δ 7.23-7.11 (m, 4H), 5.03-4.98 (m, 2H), 4.09 (dd, 1H, J=15.7, J=2.6 Hz), 1.46 (d, J=6.5 Hz, 3H), 1.28 (s, 9H).

B.1.3. Synthesis of (1S)-1-methyl-2,3-dihydro-1H-isoindole hydrochloride a22

(tert-butyl-[(1S,2S)-1-methyl-1,3-dihydro-2H-isoindol-2-yl]-oxido-sulfonium a21 (12.7 g, 53.5 mmol, 1 eq) was dissolved in EtOH (125 mL) and cooled with an ice water bath. Concentrated HCl (17.8 mL, 214 mmol) was added. The mixture was allowed to warm to it and stirred for 1 h. The reaction mixture was concentrated, stripped three times with toluene and the residue was triturated in Et$_2$O (125 mL). The solids were filtered and dried to obtain 10.70 g of (1S)-1-methyl-2,3-dihydro-1H-isoindole hydrochloride a22 as a white solid.

Yield: 88%.

LCMS (ES+): 143 (M+H+).

Chiral analysis (LC, Chiralcel OD-H, eluent: EtOH/n-heptane/DEA: 15/85/0.1): RT 9.81 min, >95% ee.

$^1$H NMR (300 MHz, DMSO-d$_6$) δ 10.06 (bs, 1H), 7.42-7.33 (m, 4H), 4.90 (q, J=6.8 Hz, 1H), 4.46 (q, J=5.3 Hz, 2H), 1.59 (d, J=6.8 Hz, 3H).

B.2. Synthesis of (1S)-4-iodo-1-methyl-2,3-dihydro-1H-isoindole hydrochloride a27

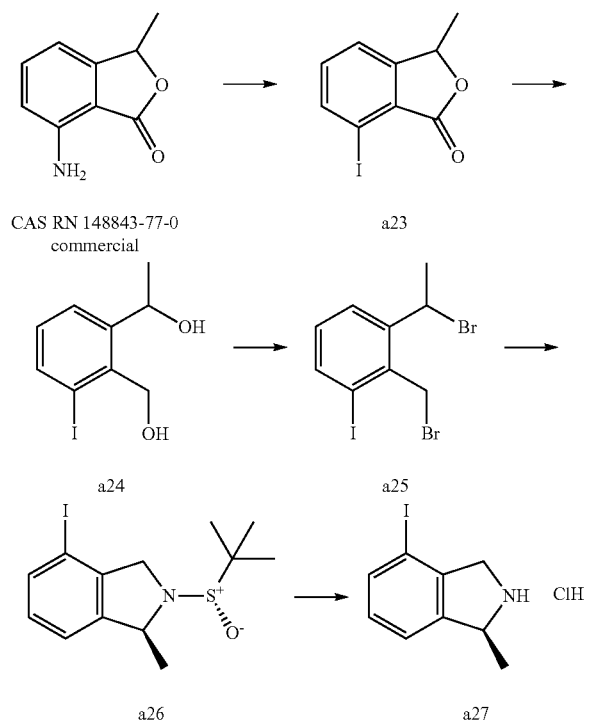

B.2.1. Synthesis of 7-iodo-3-methyl-2-benzofuran-1(3H)-one a23

To a solution of 7-amino-3-methyl-2-benzofuran-1(3H)-one (commercial, 13.3 g, 81.5 mmol) in acetone (170 mL) was added 37% concentrated HCl (17 mL, 203.56 mmol) at 0° C. The solution became heterogeneous. A solution of sodium nitrite (6.2 g, 90 mmol) in water (35 mL) was added dropwise, then after 5 min. of stirring, a solution of KI (27.1 g, 163 mmol) in water (70 mL) was added. The reaction mixture was stirred overnight at rt. Sodium acetate (9 g, 108.4 mmol) was added and the reaction mixture was taken up with DCM (200 mL). The aqueous layer was extracted twice with DCM (200 mL). The organic layer was successively washed with an aqueous solution of Na$_2$S$_2$O$_3$ solution (200 mL, 10% wt) and with water (200 mL). The organic layer was dried over MgSO$_4$, filtered and concentrated under vacuum to afford 21 g of 7-iodo-3-methyl-2-benzofuran-1(3H)-one a23 as a solid.

Yield: 94%.

HPLC (Basic Mode): RT 4.63 min, 85% purity.

B.2.2. Synthesis of 1-[2-(hydroxymethyl)-3-iodophenyl]ethanol a24

To a solution of 7-iodo-3-methyl-2-benzofuran-1(3H)-one a23 (4.24 g, 15.5 mmol) in THF (250 mL) was added at 0° C. lithium borohydride (1.77 g, 77.2 mmol) and the reaction mixture was stirred at 0° C. overnight. Lithium borohydride (1.77 g, 77.2 mmol) was added again. The reaction mixture was stirred at 0° C. for 48 h, then quenched carefully with a 1N aqueous solution of HCl (100 mL). The mixture was stirred at 0° C. for 3 h and concentrated under vacuum. The aqueous layer was extracted twice with DCM (300 mL). The organic layer was dried over MgSO$_4$, filtered and concentrated under vacuum to afford 3.25 g of 1-[2-(hydroxymethyl)-3-iodophenyl]ethanol a24 as a solid.

Yield: 53% (crude).

HPLC (Basic Mode): RT 3.70 min (70% purity) & 2.68 min (30% purity).

B.2.3. Synthesis of 1-(1-bromoethyl)-2-(bromomethyl)-3-iodobenzene a25

To a solution of 1-[2-(hydroxymethyl)-3-iodophenyl]ethanol a24 (3.25 g, 11.7 mmol) in DCM (150 mL) was added phosphorus tribromide (3.3 mL, 35 mmol) and the reaction mixture was stirred overnight at rt. The reaction mixture was diluted with DCM (100 mL), then washed with an aqueous saturated solution of NaHCO$_3$ (100 mL). The organic layer was dried over MgSO$_4$, filtered and concentrated under vacuum to yield 4.3 g of 1-(1-bromoethyl)-2-(bromomethyl)-3-iodobenzene a25 as an oil.

Yield: 91% (crude).

HPLC (Basic Mode): RT 5.95 min (52% purity) & 6.43 min (39% purity).

B.2.4. Method F. Synthesis of tert-butyl [(1S,2S)-4-iodo-1-methyl-1,3-dihydro-2H-isoindol-2-yl]-oxido-sulfonium a26

To a solution of 1-(1-bromoethyl)-2-(bromomethyl)-3-iodobenzene a25 (4.2 g, 10 mmol) and (R)-(+)-2-methyl-2-propanesulfinamide (1.3 g, 11 mmol) in DMF (50 mL) was added by portions NaH (60% in mineral oil, 830 mg, 20.75 mmol) at rt. The reaction mixture was allowed to stir for 2 h at rt and EtOAc (100 mL) was added. The reaction mixture was stirred overnight, then the solid formed was filtered and the organic layer was washed with brine (200 mL) and water (100 mL). The organic layer was dried over MgSO$_4$, filtered and concentrated under vacuum. The residue was purified by column chromatography using 10% EtOAc in n-heptane as eluent, then by reverse phase chromatography (basic mode, standard LC). Chiral resolution (SFC, Whelko-01 (R,R), 50*227 mm, 360 mL/min, 220 nm, 40° C., eluent: 20% MeOH) afforded 484 mg of tert-butyl [(1S,2S)-4-iodo-1-methyl-1,3-dihydro-2H-isoindol-2-yl]-oxido-sulfonium a26 as a pink oil.

Yield: 13%.

LCMS (ES$^+$) 364 (M+H)$^+$, 100% purity.

Chiral analysis (LC, Whelko-01 (R,R), 250*4.6 mm, 1 mL/min, 220 nm, 30° C., eluent: EtOH/DEA 100/0.1): RT 4.40 min (other enantiomer 7.43 min), 100% ee.

tert-butyl [(1S,2S)-4-bromo-1-methyl-1,3-dihydro-2H-isoindol-2-yl]-oxido-sulfonium a55 may be synthesized according to a method analogous to Method F using 1-bromo-3-(1-bromoethyl)-2-(bromomethyl)benzene a28 as starting material. Purification by column chromatography using DCM as eluent, followed by chiral resolution (SFC, Whelko-01 (R,R), 50*227 mm, 360 mL/min, 220 nm, 25° C., eluent: from 10 to 40% MeOH) afforded tert-butyl [(1S,2S)-4-bromo-1-methyl-1,3-dihydro-2H-isoindol-2-yl]-oxido-sulfonium a55.

Yield: 12%.

LCMS (ES$^+$): 318 (M+H)$^+$.

Chiral analysis (LC, Whelko-01 (R,R), 250*4.6 mm, 1 mL/min, 220 nm, 30° C., eluent: EtOH/DEA 100/0.1): RT 4.32 min (other enantiomer 7.45 min), 100% ee.

B.2.5. Method G. Synthesis of (1S)-4-iodo-1-methyl-2,3-dihydro-1H-isoindole hydrochloride a27

To a solution of tert-butyl [(1S,2S)-4-iodo-1-methyl-1,3-dihydro-2H-isoindol-2-yl]-oxido-sulfonium a26 (480 mg, 1.321 mmol) in EtOH (20 mL) was added at 0° C. a concentrated solution of HCl in EtOH (5 mL) and the reaction mixture was stirred at rt overnight. The solid formed was filtered off and dried under vacuum to afford 360 mg of pure (1S)-4-iodo-1-methyl-2,3-dihydro-1H-isoindole hydrochloride a27 as a white solid.

Yield: 92%

HPLC (Basic Mode): RT 4.44 min, 98% purity.

(1S)-4-bromo-1-methyl-isoindoline hydrochloride a56 may be synthesized according a method analogous to Method G using tert-butyl [(1S,2S)-4-bromo-1-methyl-1,3-dihydro-2H-isoindol-2-yl]-oxido-sulfonium a55 as starting material.

Yield: 92% (crude).

LCMS (ES$^+$): 212/214 (M+H)$^+$.

C. Synthesis of Dibromo Derivatives of Formula VI

C.1. Synthesis of 1-bromo-3-(1-bromoethyl)-2-(bromomethyl)benzene a28

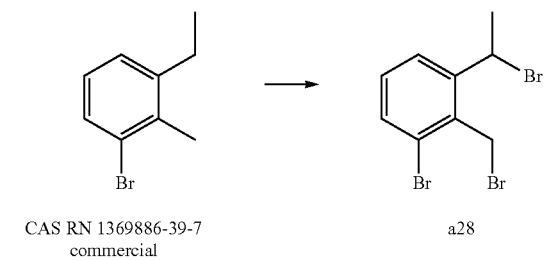

CAS RN 1369886-39-7
commercial a28

1-Bromo-3-ethyl-2-methylbenzene (commercial, 175 mg, 0.88 mmol) was dissolved in carbon tetrachloride (4 mL). NBS (330 mg, 1.85 mmol) and benzoyl peroxide (11 mg, 40 µmol) were added and the resulting mixture was heated at 80° C. overnight. DCM (10 mL) was added and the organic layer was successively washed with an aqueous saturated solution of sodium bicarbonate (5 mL), a 1N aqueous solution of HCl (5 mL) and water (5 mL). The resulting organic layer was dried over MgSO$_4$, filtered and concentrated under vacuum to yield 293 mg of 1-bromo-3-(1-bromoethyl)-2-(bromomethyl)benzene a28 as a yellow oil.

Yield: 93% (crude).

C.2. Synthesis of 4-(1-bromoethyl)-3-(bromomethyl)benzonitrile a29

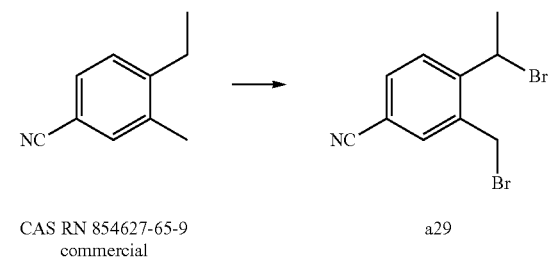

CAS RN 854627-65-9
commercial a29

4-Ethyl-3-methylbenzonitrile (commercial, 500 mg, 3.34 mmol) was dissolved in carbon tetrachloride (10 mL). NBS (1.25 g, 7.01 mmol) and benzoyl peroxide (41 mg, 0.17 mmol) were added and the resulting mixture heated at 80° C. overnight. The organic layer was successively washed with water (10 mL), an aqueous saturated solution of sodium bicarbonate (10 mL), a 1N aqueous solution of HCl (10 mL) and water (10 mL). The organic layer was dried over MgSO$_4$, filtered and concentrated under vacuum to 1.16 g of 4-(1-bromoethyl)-3-(bromomethyl)benzonitrile a29 as a yellow oil.

Yield: 100% (crude).

Examples

D. Synthesis of Compounds of Formula I-A.

D.1. Method A. Synthesis of 2-(2,6-dichlorophenyl)-1-(1-methyl-1,3-dihydro-2H-isoindol-2-yl)ethanone 1 and enantiomers

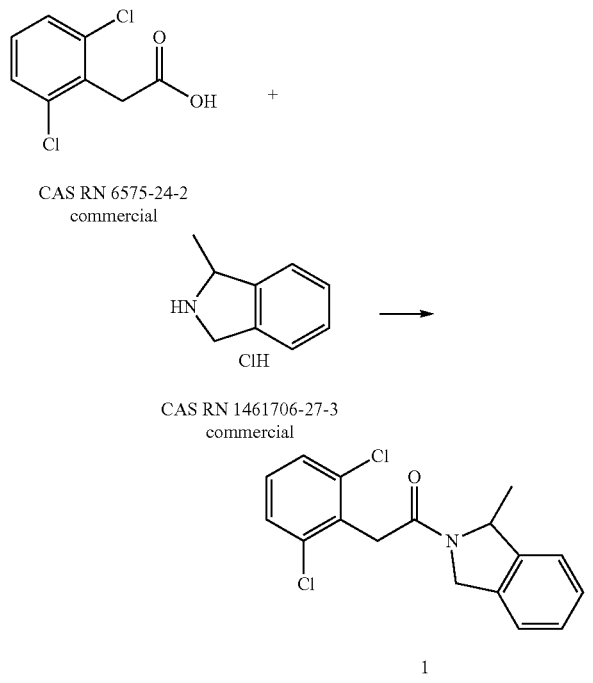

CAS RN 6575-24-2
commercial

CAS RN 1461706-27-3
commercial

1

(2,6-Dichlorophenyl)acetic acid (commercial, 246 mg, 1.2 mmol) was dissolved in DCM (25 mL). 1-Chloro-N,N-2-trimethylpropenylamine (188 μL, 14 mmol) was added under argon at rt. After 30 min., a mixture of 1-methyl-2,3-dihydro-1H-isoindole hydrochloride (commercial, 140 mg, 1 mmol) and TEA (420 μL, 3 mmol) in DCM (25 mL) was added. The mixture was stirred overnight at rt. The reaction mixture was diluted with DCM (15 mL), then successively washed with a 1N aqueous solution of HCl (50 mL) and an aqueous saturated solution of $Na_2CO_3$. The organic layer was dried over $MgSO_4$, filtered and concentrated under vacuum. The residue was recrystallized from MeOH (5 mL) to afford 115 mg of racemate 2-(2,6-dichlorophenyl)-1-(1-methyl-1,3-dihydro-2H-isoindol-2-yl)ethanone 1.

LCMS ($ES^+$): 320/322/324 $(M+H)^+$, 90% purity.

Chiral resolution (SFC, Chiralcel OJ, 50*275 mm, 360 mL/min, 220 nm, 25° C., eluent: from 20% iPrOH) afforded:

30 mg of 2-(2,6-dichlorophenyl)-1-[(1S)-1-methyl-1,3-dihydro-2H-isoindol-2-yl]ethanone 2 as a white solid. Yield: 9%.

LCMS ($ES^+$): 320/322/324 $(M+H)^+$, 97.7% purity.

Chiral analysis (LC, Chiralcel OJ-H, 250*4.6 mm, 1 mL/min, 220 nm, 30° C., eluent: iPrOH/n-heptane/DEA 50/50/0.1): RT 7.37 min, 100% ee.

20 mg of 2-(2,6-dichlorophenyl)-1-[(1R)-1-methyl-1,3-dihydro-2H-isoindol-2-yl]ethanone 3 as a white solid. Yield: 6%.

LCMS ($ES^+$): 320/322/324 $(M+H)^+$, 94.74% purity.

Chiral analysis (LC, Chiralcel OJ-H, 250*4.6 mm, 1 mL/min, 220 nm, 30° C., eluent: iPrOH/n-heptane/DEA 50/50/0.1): RT 13.13 min, 99.5% ee.

2-(2-chloro-6-iodophenyl)-1-(1-methyl-1,3-dihydro-2H-isoindol-2-yl)ethanone 4 may be synthesized according to a method analogous to Method A using 1-methyl-2,3-dihydro-1H-isoindole hydrochloride and 2-(2-chloro-6-iodo-phenyl)acetic acid as starting materials. Conditions: DCM, TEA (3 eq), rt, overnight. Purification: reverse phase chromatography (acidic mode, standard LC).

Yield: 12%.

LCMS ($ES^+$): 412/414/416 $(M+H)^+$, 97.3% purity.

Appearance: off-white solid.

D.2. Method B. Synthesis of 2-(2,4-dichloropyridin-3-yl)-1-(1-methyl-1,3-dihydro-2H-isoindol-2-yl)ethanone 5

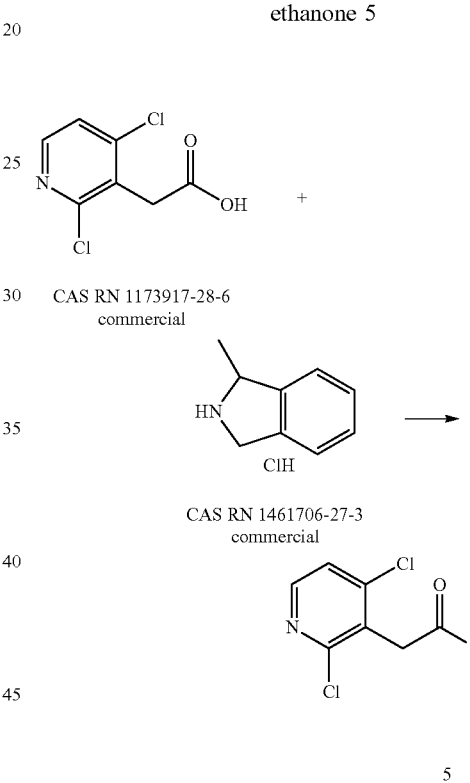

CAS RN 1173917-28-6
commercial

CAS RN 1461706-27-3
commercial

5

(2,4-Dichloropyridin-3-yl)acetic acid (commercial, 100 mg, 0.47 mmol) was dissolved in DMF (5 mL). 1-Methyl-2,3-dihydro-1H-isoindole hydrochloride (commercial, 66 mg, 0.47 mmol) and TEA (130 μL, 0.9 mmol) were added at rt, then BOP (242 mg, 0.55 mmol) was added. The mixture was stirred overnight at 50° C. Water was added, then the reaction mixture was extracted thrice with DCM. The organic layer was washed with brine, dried over $MgSO_4$, filtered and concentrated under vacuum. The residue was first purified by reverse phase chromatography (basic mode, standard LC) to yield 83 mg of 2-(2,4-dichloropyridin-3-yl)-1-(1-methyl-1,3-dihydro-2H-isoindol-2-yl)ethanone 5.

LCMS ($ES^+$): 321/323/325 $(M+H)^+$, 100% purity. The following compounds may be synthesized according to a method analogous to Method B.

| N° | Starting material | Conditions | Reaction time | Purification conditions | Yield (%) |
|---|---|---|---|---|---|
| 6 | acid II: 2,6-Dichloro-phenylacetic acid amine III: 1-methyl-4-nitro-isoindoline hydrochloride | DMF, TEA (3 eq), rt | overnight | NA | 100 |
| 7 | acid II: 2-Chloro-6-cyanophenylacetic acid amine III: a22 | DMF, TEA (3 eq), 70° C. | 15 min. | Basic RP-LCMS | 28 |
| 8 | acid II: a3 amine III: a22 | DCM, DIPEA (2 eq), rt | overnight | Basic RP (standard LC) | 71 |
| 9 | acid II: a9 amine III: a22 | DCM, DIPEA (2 eq), rt | overnight | Basic mode, standard LC | 71 |
| 10 | acid II: a13 amine III: a22 | DMF, DIPEA (2 eq), 30° C. | 48 h | Basic mode, standard LC | 29 |
| 11 | acid II: a18 amine III: a22 | DCM, DIPEA (2 eq), rt | overnight | Basic mode, standard LC | 85 |

2-(2,6-dichlorophenyl)-1-(1-methyl-4-nitro-1,3-dihydro-2H-isoindol-2-yl)ethanone 6

LCMS (ES+): 365/367/369 (M+H)+, 100% purity.
Appearance: pink solid.

3-chloro-2-{2-[(1S)-1-methyl-1,3-dihydro-2H-isoindol-2-yl]-2-oxoethyl}benzonitrile 7

LCMS (ES+): 311/313/315 (M+H)+, >98% purity.
Appearance: off-white solid powder.

2-(3,5-dichloro-2-methylpyridin-4-yl)-1-[(1S)-1-methyl-1,3-dihydro-2H-isoindol-2-yl]ethanone 8

LCMS (ES+): 335/337/339 (M+H)+, 100% purity.
Appearance: orange oil.

2-(3-bromo-5-chloropyridin-4-yl)-1-[(1S)-1-methyl-1,3-dihydro-2H-isoindol-2-yl]ethanone 9

LCMS (ES+): 365/367/369 (M+H)+, 100% purity.
Appearance: white solid.

2-(5-chloro-1H-pyrrolo[2,3-b]pyridin-4-yl)-1-[(1S)-1-methyl-1,3-dihydro-2H-isoindol-2-yl]ethanone 10

LCMS (ES+): 326/328 (M+H)+, 99.3% purity.
Appearance: beige solid.

2-(3,5-dichloro-2-methoxypyridin-4-yl)-1-[(1S)-1-methyl-1,3-dihydro-2H-isoindol-2-yl]ethanone 11

LCMS (ES+): 351/353/355 (M+H)+, 96.2% purity.
Appearance: colorless oil.

D.3. Synthesis of 2-(3,5-dichloropyridin-4-yl)-1-[(1S)-1-methyl-1,3-dihydro-2H-isoindol-2-yl]ethanone 12

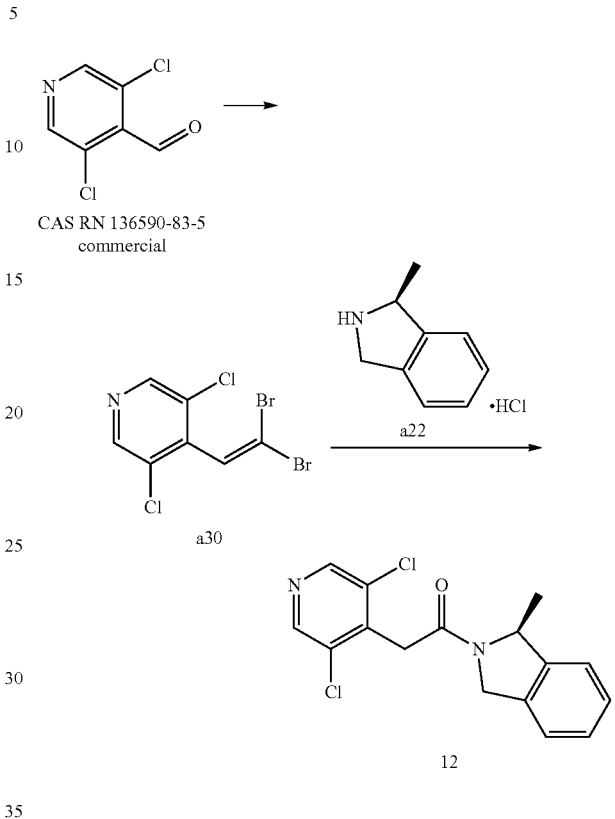

D.3.1. Synthesis of 3,5-dichloro-4-(2,2-dibromovinyl)pyridine a30

3,5-Dichloropyridine-4-carbaldehyde (commercial, 5 g, 27.55 mmol) was dissolved in DCM (150 mL) at 0° C. Carbon tetrabromide (14.1 g, 42.6 mmol) was added. The mixture was stirred at 0° C., then a solution of triphenylphosphine (15 g, 57 mmol) in DCM (150 ml) was added dropwise. The reaction mixture was stirred at 0° C. for 4 h, then concentrated under vacuum. The residual triphenylphosphine oxide was precipitated thrice with chloroform and filtered off. The filtrate was concentrated under vacuum and the residue was purified by column chromatography using 20% n-heptane in DCM as eluent to yield 5.6 g of 3,5-dichloro-4-(2,2-dibromovinyl)pyridine a30 as a colorless oil which was stored at 4° C.
Yield: 61%.
GC-MS: (330 M+).

D.3.2. Synthesis of 2-(3,5-dichloropyridin-4-yl)-1-[(1S)-1-methyl-1,3-dihydro-2H-isoindol-2-yl]ethanone 12

A solution of 3,5-dichloro-4-(2,2-dibromovinyl)pyridine a30 (3.34 g, 10 mmol) in water (36 mL) and THF (48 mL) was stirred at rt, then cooled to 0° C. (1S)-1-Methyl-2,3-dihydro-1H-isoindole hydrochloride a22 (2.2 g, 13 mmol) was added, then potassium hydroxide (2.24 g, 40 mmol) was added portion wise at 0° C. The reaction mixture was stirred at 0° C. for 1 h, then a 3N aqueous solution of HCl (45 mL) was added and the mixture was allowed to warm to rt. The reaction mixture was extracted thrice with DCM (200 mL). The organic layer was successively washed with a 1N aqueous solution of HCl (100 mL), an aqueous saturated solution of sodium carbonate (100 mL) and brine (100 mL). The resulting organic layer was dried over MgSO$_4$ and filtered. Charcoal (25 g) was added to the filtrate and the resulting mixture was filtered and concentrated under vacuum to yield a brown solid. The residue was triturated in MeOH (5 mL), filtered off and washed twice with MeOH (5 mL) and MeOH/hexanes (1:1; 5 mL). The resulting solid was dried under vacuum to afford 2.2 g of 2-(3,5-dichloro-pyridin-4-yl)-1-[(1S)-1-methyl-1,3-dihydro-2H-isoindol-2-yl]ethanone 12 as a white solid.

Yield: 68%.

LCMS (ES$^+$): 321/323/325 (M+H)$^+$, 96.3% purity.

Chiral analysis (LC, Chiralpak IA, 250*4.6 mm, 1 mL/min, 220 nm, 30° C., eluent: n-heptane/EtOAc/DEA 50/50/0.1): RT 10.06 min (other enantiomer at 6.87 min), 100% ee.

D.4. Synthesis of N-{(1S)-2-[(2,6-dichlorophenyl) acetyl]-1-methyl-2,3-dihydro-1H-isoindol-4-yl}methanesulfonamide 13

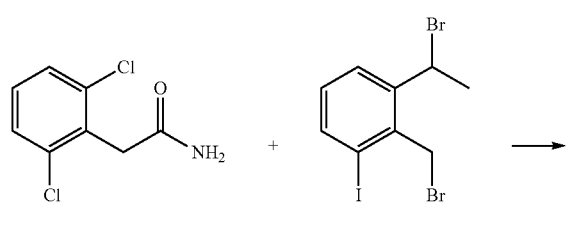

D.4.1. Method C. Synthesis of 2-(2,6-dichlorophenyl)-1-(4-iodo-1-methyl-1,3-dihydro-2H-isoindol-2-yl)ethanone a31

1-(1-bromoethyl)-2-(bromomethyl)-3-iodobenzene a25 (1.5 g, 3.7 mmol) was dissolved in anhydrous DMF (13 mL) at rt, then 2-(2,6-dichlorophenyl)acetamide (commercial, 0.76 g, 3.7 mmol), sodium hydride (60% in mineral oil, 0.3 g, 7.4 mmol) were added at 0° C. The reaction mixture was stirred at rt for few hours, then poured on ice/water mixture. The white precipitate formed was filtered off and washed thrice with water (15 mL). The solid was recrystallized from EtOH-water to yield 1.43 g of 2-(2,6-dichlorophenyl)-1-(4-iodo-1-methyl-1,3-dihydro-2H-isoindol-2-yl)ethanone a31 as a white solid.

Yield: 86%.

LCMS (ES$^+$): 446/448/450 (M+H)$^+$.

D.4.2. Synthesis of N-{(1S)-2-[(2,6-dichlorophenyl) acetyl]-1-methyl-2,3-dihydro-1H-isoindol-4-yl}methanesulfonamide 13

2-(2,6-dichlorophenyl)-1-(4-iodo-1-methyl-1,3-dihydro-2H-isoindol-2-yl)ethanone a31 (250 mg, 0.56 mmol), methanesulfonamide (109 mg, 1.12 mmol), potassium phosphate tribasic (368 mg, 1.681 mmol), CuI (53 mg, 0.28 mmol) were dissolved in DMF (6 mL) in a schlenk tube under nitrogen atmosphere. (1R,2R)-(–)-1,2-diaminocyclohexane (64 mg, 0.56 mmol) was added and the mixture was stirred overnight at 140° C. The reaction mixture was poured onto water and the aqueous layer was extracted thrice with DCM. The organic layer was dried over MgSO$_4$, filtered and concentrated under vacuum. The residue was purified by reverse phase chromatography (Basic mode, standard LC) to afford 47 mg of racemate derivative as a beige solid (Yield: 20%, LCMS (ES$^+$): 413/415/417 (M+H)$^+$). Chiral resolution (SFC, Chiralcel OJ, 50*275 mm, 360 mL/min, 220 nm, 25° C., eluent: from 20% MeOH for 11 min., then 40% MeOH for 20 min.) afforded 17 mg of N-{(1S)-2-[(2,6-dichlorophenyl)acetyl]-1-methyl-2,3-dihydro-1H-isoindol-4-yl}methanesulfonamide 13 as a white solid.

Yield: 7%.

LCMS (ES$^+$): 413/415/417 (M+H)$^+$, 95% purity.

Chiral analysis (LC, Chiralcel OJ-H, 250*4.6 mm, 1 mL/min, 220 nm, 30° C., eluent: MeOH/DEA 100/0.1): RT 3.82 min (other enantiomer at 6.23 min), 100% ee.

D.5. Synthesis of 1-[(1S)-4-amino-1-methyl-1,3-dihydro-2H-isoindol-2-yl]-2-(2,6-dichlorophenyl) ethanone 14

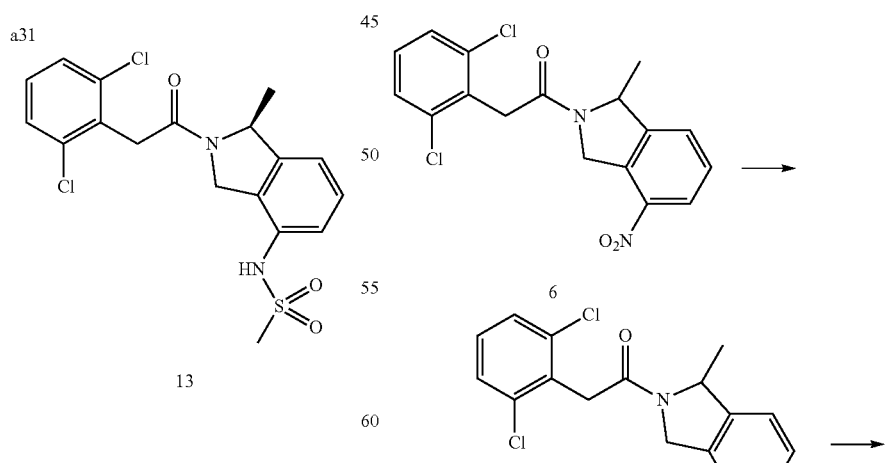

-continued

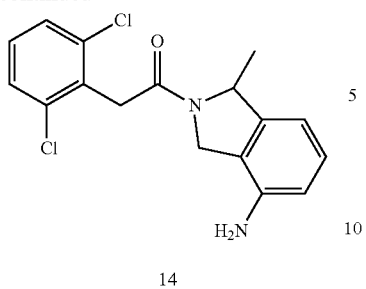

14

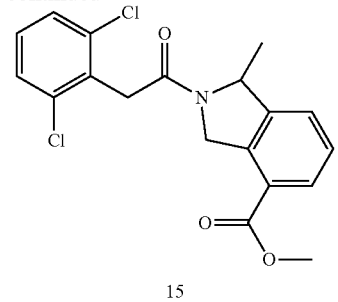

15

2-(2,6-dichlorophenyl)-1-(1-methyl-4-nitro-1,3-dihydro-2H-isoindol-2-yl)ethanone 6 (222 mg, 18.4 mmol) was hydrogenated in dioxane (5 mL), with platinum on carbon (5% loading, 15 mg) at 50° C. and 50 bars overnight. The reaction mixture was filtered through a pad of Celite® and the filtrate was concentrated under vacuum to afford 200 mg of racemate 1-(4-amino-1-methyl-1,3-dihydro-2H-isoindol-2-yl)-2-(2,6-dichlorophenyl)ethanone 14-(Rac) as a white solid (Yield: 100%, LCMS (ES$^+$): 335/337/339 (M+H)$^+$, 99.3% purity).

Chiral resolution (SFC, Chiralcel IA, 50*266 mm, 360 mL/min, 220 nm, 25° C., eluent: from 20 to 35% iPrOH) afforded 16 mg of 1-[(1S)-4-amino-1-methyl-1,3-dihydro-2H-isoindol-2-yl]-2-(2,6-dichlorophenyl)ethanone 14 as a white solid.

LCMS (ES$^+$): 335/337/339 (M+H)$^+$, 100% purity.

Chiral analysis (LC, Chiralcel OD, 250*4.6 mm, 1 mL/min, 220 nm, 30° C., eluent: MeOH/DEA 100/0.1): RT 5.60 min (other enantiomer at 6.98 min), 97% ee.

D.6. Synthesis of methyl 2-[(2,6-dichlorophenyl)acetyl]-1-methyl-2,3-dihydro-1H-isoindole-4-carboxylate 15

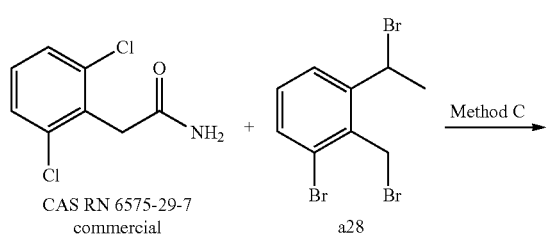

CAS RN 6575-29-7
commercial a28

Method C

D.6.1. Synthesis of 1-(4-bromo-1-methyl-1,3-dihydro-2H-isoindol-2-yl)-2-(2,6-dichlorophenyl)ethanone a32

1-Bromo-3-(1-bromoethyl)-2-(bromomethyl)benzene a28 (293 mg, 0.82 mmol) was dissolved in DMF (4 mL) at rt, then 2-(2,6-dichlorophenyl)acetamide (commercial 184 mg, 0.9 mmol) and sodium hydride (66 mg, 1.65 mmol) were added at 0° C. The reaction mixture was stirred at rt, then poured on a water (35 mL). The precipitate formed was filtered off and washed with water (10 mL). The solid was dried under vacuum to afford 185 mg of 1-(4-bromo-1-methyl-1,3-dihydro-2H-isoindol-2-yl)-2-(2,6-dichlorophenyl)ethanone a32 as a white solid which was used in next step without any further purification.

Yield: 74% (crude)

D.6.2. Synthesis of methyl 2-[(2,6-dichlorophenyl)acetyl]-1-methyl-2,3-dihydro-1H-isoindole-4-carboxylate 15

In a vial, 1-(4-bromo-1-methyl-1,3-dihydro-2H-isoindol-2-yl)-2-(2,6-dichlorophenyl)ethanone a32 (50 mg, 0.12 mmol) was dissolved in MeOH (5 mL), then DIPEA (44 µL, 0.25 mmol), dibromo[(S)-(+2,2'-bis(diphenylphosphino)-1,1'-binaphthyl]palladium(II) (6 mg, 6.74 µmol) were added. The vial was placed in an autoclave under 8 bars of carbon monoxide. The reaction mixture was stirred overnight at 80° C. The reaction mixture was poured on water and extracted thrice with DCM. The organic layer was dried over MgSO$_4$, filtered and concentrated under vacuum. The residue was purified by reverse phase chromatography (Basic mode, LCMS prep) to yield 21 mg of methyl 2-[(2,6-dichlorophenyl)acetyl]-1-methyl-2,3-dihydro-1H-isoindole-4-carboxylate 15 as a beige solid.

Yield: 44%.

LCMS (ES$^+$): 378/380/382 (M+H)$^+$, 95.9% purity.

D.7. Synthesis of 2-[2,6-dichloro-3-(hydroxymethyl)phenyl]-1-(1-methyl-1,3-dihydro-2H-isoindol-2-yl)ethanone 16

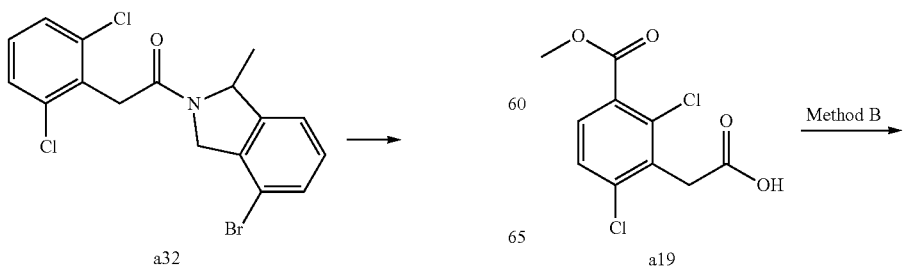

a32 a19

Method B

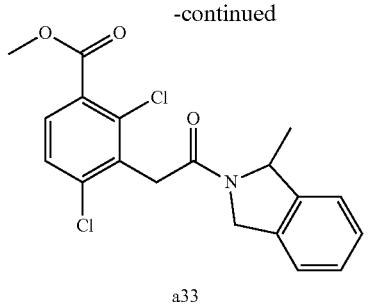

a33

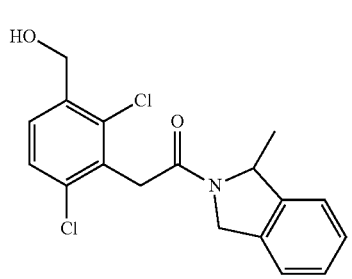

16

D.7.1. Synthesis of methyl 2,4-dichloro-3-[2-(1-methyl-1,3-dihydro-2H-isoindol-2-yl)-2-oxoethyl]benzoate a33

Compound a33 may be synthesized according to a method analogous to Method B using [2,6-dichloro-3-(methoxycarbonyl)phenyl]acetic acid a19 and 1-methyl-2,3-dihydro-1H-isoindole hydrochloride as starting materials. Conditions: DCM, DIPEA (3 equiv), rt, overnight. Purification: column chromatography using from 0 to 4% MeOH in DCM as eluent.

Yield: 70%.

LCMS (ES$^+$): 378/380/382 (M+H)$^+$.

D.7.2. Synthesis of 2-[2,6-dichloro-3-(hydroxymethyl)phenyl]-1-(1-methyl-1,3-dihydro-2H-isoindol-2-yl)ethanone 16

Methyl 2,4-dichloro-3-[2-(1-methyl-1,3-dihydro-2H-isoindol-2-yl)-2-oxoethyl]benzoate a33 (60 mg, 0.16 mmol) was dissolved in THF (5 mL). The mixture was cooled to 0° C., then lithium aluminium hydride (19 mg, 0.48 mmol) was added. The mixture was stirred overnight at rt, then quenched with a 1N aqueous solution of HCl (1 mL) and extracted with DCM. The organic layer was washed twice with an aqueous saturated solution of NaHCO$_3$, dried over MgSO$_4$, filtered and concentrated under vacuum. The residue was triturated with ACN/water (70:30) and the precipitate was filtered off then dried under vacuum to yield 11 mg of 2-[2,6-dichloro-3-(hydroxymethyl)phenyl]-1-(1-methyl-1,3-dihydro-2H-isoindol-2-yl)ethanone 16 as a grey solid.

Yield: 20%.

LCMS (ES$^+$): 350/352/354 (M+H)$^+$, 93.6% purity.

D.8. Synthesis of 2-[2,6-dichloro-3-(hydroxymethyl)phenyl]-1-[(1S)-1-methyl-1,3-dihydro-2H-isoindol-2-yl]ethanone 17

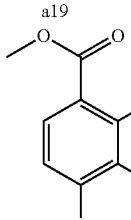

a19

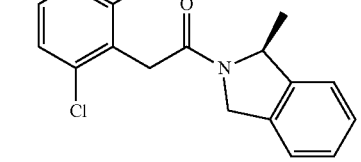

a34

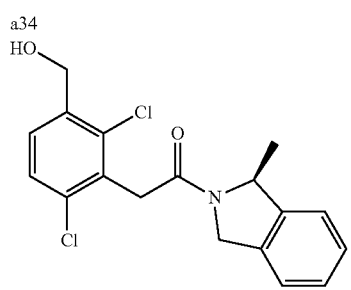

17

D.8.1. Synthesis of methyl 2,4-dichloro-3-{2-[(1S)-1-methyl-1,3-dihydro-2H-isoindol-2-yl]-2-oxoethyl}benzoate a34

Compound a34 may be synthesized according to a method analogous to Method B using [2,6-dichloro-3-(methoxycarbonyl)phenyl]acetic acid a19 and (1S)-1-methyl-2,3-dihydro-1H-isoindole hydrochloride a22 as starting materials. Conditions: DCM, DIPEA (3 eq), rt, overnight. Purification: column chromatography using from 0 to 4% MeOH in DCM as eluent.

Yield: 66%.

LCMS (ES$^+$): 378/380/382 (M+H)$^+$.

D.8.2. Synthesis of 2-[2,6-dichloro-3-(hydroxymethyl)phenyl]-1-[(1S)-1-methyl-1,3-dihydro-2H-isoindol-2-yl]ethanone 17

Compound 17 may be synthesized according to a method analogous to the method described in D.7.2. Purification: reverse phase chromatography (Basic mode, standard LC).

Yield: 66%.

LCMS (ES$^+$): 350/352/354 (M+H)$^+$, 100% purity.

Appearance: white solid.

D.9. 2-(2,6-dichlorophenyl)-1-(4-hydroxy-1-methyl-1,3-dihydro-2H-isoindol-2-yl)ethanone 18

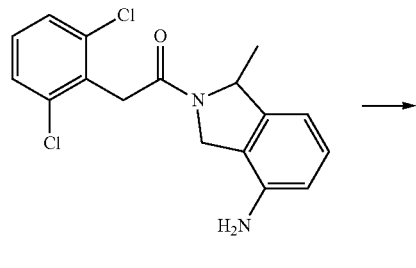

14-(Rac)

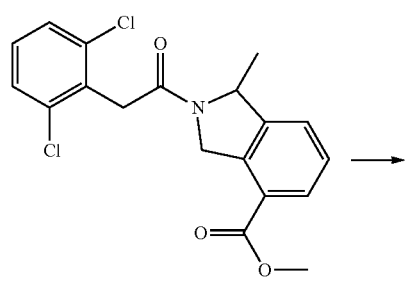

18

1-(4-amino-1-methyl-1,3-dihydro-2H-isoindol-2-yl)-2-(2,6-dichlorophenyl)ethanone 14-(Rac) (100 mg, 0.3 mmol) was dissolved in water (5 mL). KBr (124 mg 1.044 mmol) was added and the mixture was cooled to 0° C. A solution sodium nitrite (0.42 mmol) in water was added dropwise. The reaction mixture was stirred at rt for 48 h. The beige precipitate formed was filtered off, washed thrice with Et$_2$O (10 mL) and dried under vacuum to afford 115 mg of 2-(2,6-dichlorophenyl)-1-(4-hydroxy-1-methyl-1,3-dihydro-2H-isoindol-2-yl)ethanone 18 as a beige solid.

Yield: 96%

LCMS (ES$^+$): 336/338/340 (M+H)$^+$, 95% purity.

D.10. Synthesis of 2-[(2,6-dichlorophenyl)acetyl]-1-methyl-2,3-dihydro-1H-isoindole-4-carboxamide 19

15

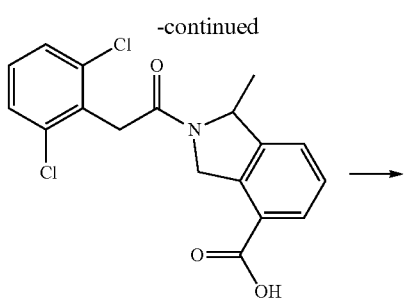

a35

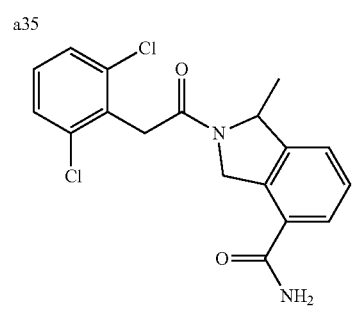

19

D.10.1. Synthesis of 2-[(2,6-dichlorophenyl)acetyl]-1-methyl-2,3-dihydro-1H-isoindole-4-carboxylic acid a35

Methyl 2-[2-(2,6-dichlorophenyl)acetyl]-1-methyl-isoindoline-4-carboxylate 15 (50 mg, 0.13 mmol) was dissolved in THF (5 mL) and water (2 mL). Lithium hydroxide (6 mg, 0.26 mmol) was added at rt and the mixture was stirred overnight at rt. The reaction mixture was concentrated under vacuum and the residue washed thrice with DCM (10 mL). The organic layer was washed with brine, dried on MgSO$_4$, filtered and concentrated under vacuum to afford 36 mg of 2-[(2,6-dichlorophenyl)acetyl]-1-methyl-2,3-dihydro-1H-isoindole-4-carboxylic acid a35 as a yellow solid which was used in next step without any further purification.

Yield: 75% (crude).

LCMS (ES$^+$): 364/366/368 (M+H)$^+$.

D.10.2. Synthesis of 2-[(2,6-dichlorophenyl)acetyl]-1-methyl-2,3-dihydro-1H-isoindole-4-carboxamide 19

2-[(2,6-dichlorophenyl)acetyl]-1-methyl-2,3-dihydro-1H-isoindole-4-carboxylic acid a35 (36 mg, 99 µmol) was dissolved in DMF (1 mL). A 7M solution of ammonia (70 µL, 0.49 mmol) and TEA (42 µL, 1.98 mmol) were added at rt, then BOP (47 mg, 0.11 mmol) was added. The reaction mixture was stirred overnight at rt, then concentrated under vacuum. The residue was purified by reverse phase chromatography (basic mode, LCMS prep) to yield 5 mg of 2-[(2,6-dichlorophenyl)acetyl]-1-methyl-2,3-dihydro-1H-isoindole-4-carboxamide 19 as a yellow solid.

Yield: 14%.

LCMS (ES$^+$): 363/365/367 (M+H)$^+$, 95% purity.

D.11. Synthesis of N-{2-[(2,6-dichlorophenyl)acetyl]-1-methyl-2,3-dihydro-1H-isoindol-4-yl}acetamide 20

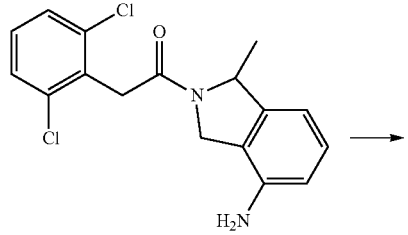

14-(Rac)

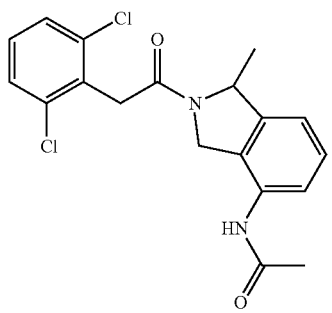

20

To a solution of 1-(4-amino-1-methyl-1,3-dihydro-2H-isoindol-2-yl)-2-(2,6-dichlorophenyl)ethanone 14-(Rac) (78 mg, 0.23 mmol) and TEA (65 μL, 0.46 mmol) in DCM (5 mL) at 0° C. was added acetyl chloride (25 μL, 0.35 mmol). The mixture was stirred at rt for 3 h, then quenched with brine (50 mL) and extracted thrice with DCM (10 mL). The organic layer was dried over MgSO₄, filtered and concentrated under vacuum. The residue was purified by reverse phase chromatography (basic mode, LC-MS prep) to yield 47 mg of N-{2-[(2,6-dichlorophenyl)acetyl]-1-methyl-2,3-dihydro-1H-isoindol-4-yl}acetamide 20 as a white solid.

Yield: 57%.

LCMS (ES⁺): 377/379/381 (M+H)⁺, 96.4% purity.

D.12. Synthesis of 2-({2-[(2,6-dichlorophenyl)acetyl]-1-methyl-2,3-dihydro-1H-isoindol-4-yl}oxy)-N-methylacetamide 21

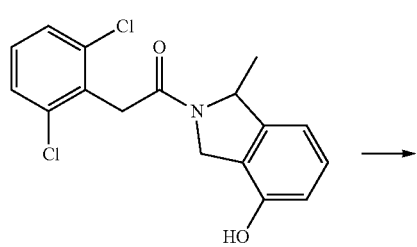

18

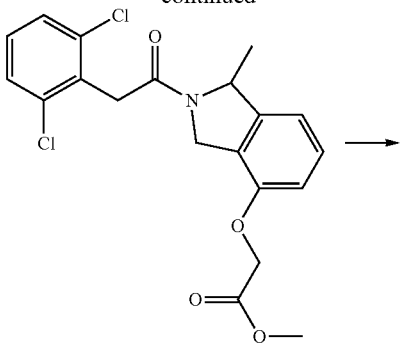

a36

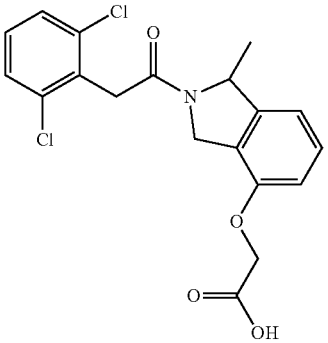

a37

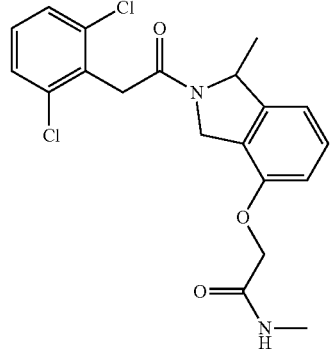

21

D.12.1. Synthesis of methyl ({2-[(2,6-dichlorophenyl)acetyl]-1-methyl-2,3-dihydro-1H-isoindol-4-yl}oxy)acetate a36

2-(2,6-dichlorophenyl)-1-(4-hydroxy-1-methyl-isoindolin-2-yl)ethanone 18 (115 mg, 0.34 mmol) and methyl bromoacetate (40 μL, 0.43 mmol) were dissolved in THF (10 mL) at rt, then sodium hydride (60% in mineral oil, 20 mg, 0.68 mmol) was added. The mixture was stirred at rt. The reaction mixture was quenched with water, extracted thrice with DCM, dried over MgSO₄, filtered and concentrated under vacuum to yield 90 mg of methyl ({2-[(2,6-dichlorophenyl)acetyl]-1-methyl-2,3-dihydro-1H-isoindol-4-yl}oxy)acetate a36 as a brown oil which was used in next step without any further purification.

Yield: 64% (crude).

LCMS (ES⁺): 408/410/412 (M+H)⁺.

D.12.2. Synthesis of ({2-[(2,6-dichlorophenyl)acetyl]-1-methyl-2,3-dihydro-1H-isoindol-4-yl}oxy)acetic acid a37

Methyl ({2-[(2,6-dichlorophenyl)acetyl]-1-methyl-2,3-dihydro-1H-isoindol-4-yl}oxy)acetate a36 (295 mg, 0.72 mmol) was dissolved in THF (7 mL) and water (3 mL). Lithium hydroxide (35 mg, 1.44 mmol) was added overnight at rt. The reaction mixture was acidified with a 1N aqueous solution of HCl and extracted with DCM. The organic layer was dried on MgSO$_4$, filtered and concentrated under vacuum to afford 242 mg of ({2-[(2,6-dichlorophenyl)acetyl]-1-methyl-2,3-dihydro-1H-isoindol-4-yl}oxy)acetic acid a37 as a brown oil which was used in next step without any further purification.

Yield: 85% (crude).

LCMS (ES$^+$): 394/396/398 (M+H)$^+$.

D.12.3. Synthesis of 2-({2-[(2,6-dichlorophenyl)acetyl]-1-methyl-2,3-dihydro-1H-isoindol-4-yl}oxy)-N-methylacetamide 21

({2-[(2,6-Dichlorophenyl)acetyl]-1-methyl-2,3-dihydro-1H-isoindol-4-yl}oxy)acetic acid a37 (120 mg, 0.3 mmol) was dissolved in DCM (5 mL). Methylamine hydrochloride (104 mg, 1.54 mmol) and TEA (130 µL, 0.92 mmol) were added at rt, then BOP (146 mg, 0.33 mmol) was added. The reaction mixture was stirred overnight at rt, quenched with a 0.5N aqueous solution of HCl and extracted with DCM. The organic layer was dried over MgSO$_4$, filtered and concentrated under vacuum. The residue was purified by reverse phase chromatography (Basic mode, standard LC) to yield 30 mg of 2-({2-[(2,6-dichlorophenyl)acetyl]-1-methyl-2,3-dihydro-1H-isoindol-4-yl}oxy)-N-methylacetamide 21 as a pink solid.

Yield: 24%.

LCMS (ES$^+$): 407/409/410 (M+H)$^+$, 93.3% purity.

D.13. Synthesis of 2-({2-[(2,6-dichlorophenyl)acetyl]-1-methyl-2,3-dihydro-1H-isoindol-4-yl}oxy)-N,N-dimethylacetamide 22

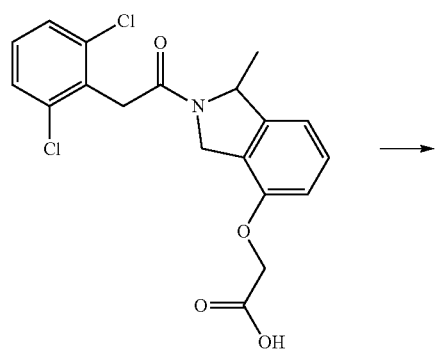

a37

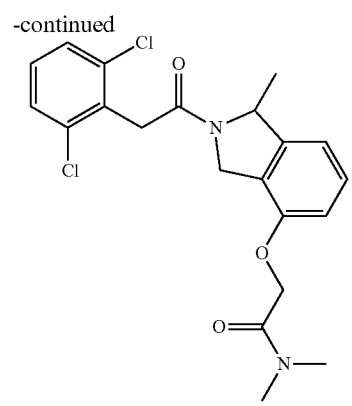

22

({2-[(2,6-Dichlorophenyl)acetyl]-1-methyl-2,3-dihydro-1H-isoindol-4-yl}oxy)acetic acid a37 (120 mg, 0.3 mmol) was dissolved in DCM (5 mL). Dimethylamine (89 µL, 1.52 mmol) and TEA (130 µL, 0.92 mmol) were added at rt, then BOP (146 mg, 0.33 mmol) was added. The reaction mixture was stirred overnight at rt, quenched with a 0.5 N aqueous solution of HCl and extracted with DCM. The organic layer was dried over MgSO$_4$, filtered and concentrated under vacuum. The residue was purified by reverse phase chromatography (Basic mode, standard LC) to yield 16 mg of 2-({2-[(2,6-dichlorophenyl)acetyl]-1-methyl-2,3-dihydro-1H-isoindol-4-yl}oxy)-N,N-dimethylacetamide 22 as a pink solid.

Yield: 12%.

LCMS (ES$^+$): 421/423/425 (M+H)$^+$, 100% purity.

D.14. Synthesis of 2-(2,6-dichlorophenyl)-1-(4-methoxy-1-methyl-1,3-dihydro-2H-isoindol-2-yl)ethanone 23

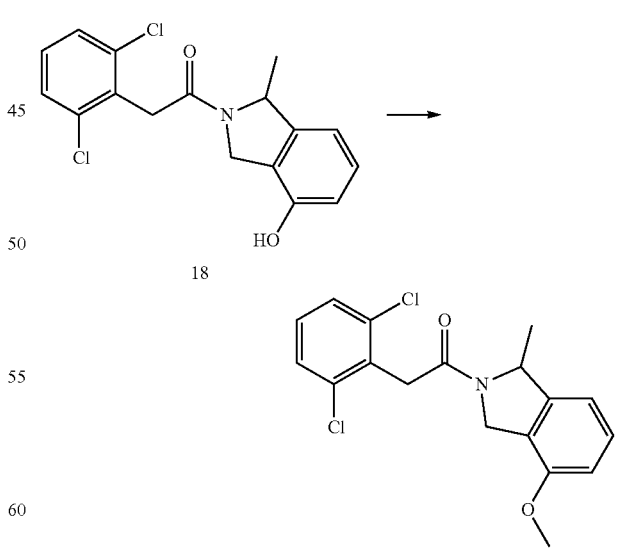

2-(2,6-Dichlorophenyl)-1-(4-hydroxy-1-methyl-1,3-dihydro-2H-isoindol-2-yl)ethanone 18 (50 mg, 0.15 mmol) was dissolved in THF (5 mL) at rt, then NaH (60% in mineral oil, 9 mg, 0.22 mmol) was added at 0° C. and the mixture was stirred at 0° C. for 2 min. Iodomethane (10 μL, 0.16 mmol) was added and the reaction mixture was stirred at 0° C. and then at rt overnight. The reaction mixture was quenched with water and extracted thrice with DCM. The organic layer was dried over MgSO$_4$, filtered and concentrated under vacuum. The residue was purified by reverse phase chromatography (Basic mode, LCMS prep) to afford mg of 2-(2,6-dichlorophenyl)-1-(4-methoxy-1-methyl-1,3-dihydro-2H-isoindol-2-yl)ethanone 23 as a yellow solid.

Yield: 29%.

LCMS (ES$^+$): 350/352/354 (M+H)$^+$, 100% purity.

D.15. Method D. Synthesis of (1S)-2-[(2,6-dichlorophenyl)acetyl]-N,1-dimethyl-2,3-dihydro-1H-isoindole-4-sulfonamide 24

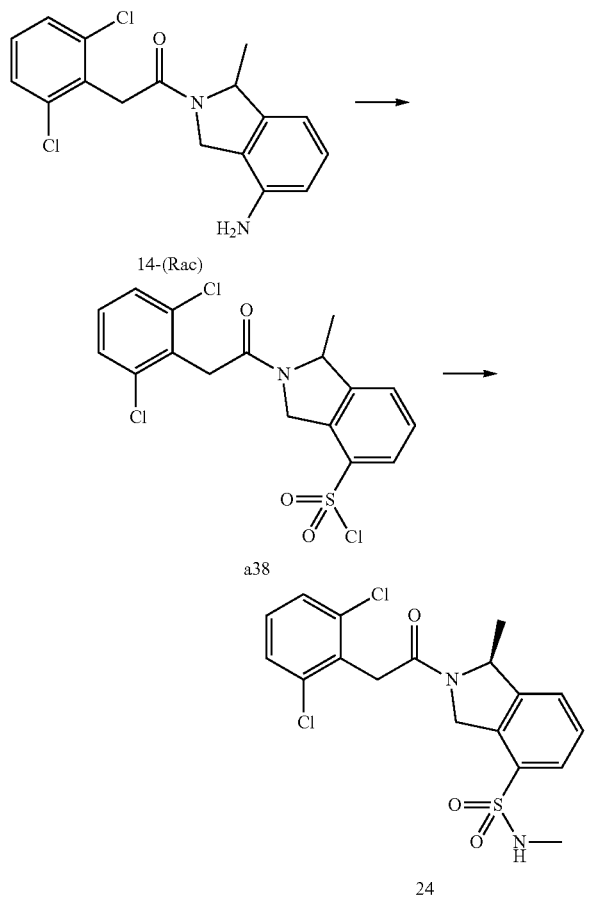

D.15.1. Synthesis of 2-[(2,6-dichlorophenyl)acetyl]-1-methyl-2,3-dihydro-1H-isoindole-4-sulfonyl chloride a38

Solution A was prepared as followed: thionyl chloride (237 μL, 3.28 mmol) was added to water (4 mL) at 5° C. and the solution was stirring overnight at rt. Copper chloride (I) (50 mg, 0.60 mmol) was added and stirring at 5° C. was maintained.

To a solution of 1-(4-amino-1-methyl-1,3-dihydro-2H-isoindol-2-yl)-2-(2,6-dichlorophenyl)ethanone 14-(Rac) (200 mg, 0.60 mmol) in hydrochloric acid 37% (4 mL) was added a solution of sodium nitrite (58 mg, 0.84 mmol) in water (10 mL) at 0° C. The reaction mixture was stirred at 0° C. for 15 min., then added dropwise at 5° C. to Solution A. The reaction mixture was stirred at rt for 3 h, then extracted thrice with DCM (20 mL). The organic layer was dried over MgSO$_4$, filtered and concentrated under vacuum to yield 234 mg of 2-[(2,6-dichlorophenyl)acetyl]-1-methyl-2,3-dihydro-1H-isoindole-4-sulfonyl chloride a38 which was used without further purification for the next step.

Yield: 93% (crude).

LCMS (ES$^+$): 418/420/422 (M+H)$^+$.

D.15.2. Synthesis of (1S)-2-[(2,6-dichlorophenyl)acetyl]-N,1-dimethyl-2,3-dihydro-1H-isoindole-4-sulfonamide 24

To a solution of 2-[(2,6-dichlorophenyl)acetyl]-1-methyl-2,3-dihydro-1H-isoindole-4-sulfonyl chloride a38 (234 mg, 0.56 mmol) in DCM (5 mL) was added a solution of methylamine in EtOH (33%) (0.153 mL, 1.23 mmol). After overnight stirring at room temperature, the reaction mixture was washed with brine and extracted with 3×10 mL of DCM. The combined organic phase was dried over MgSO$_4$ and evaporated under vacuum. The residue was resolved by Chiral resolution (SFC, Chiralcel OD, 50*266 mm, 360 mL/min, 220 nm, 25° C., eluent: from 20% MeOH for 15 min., then 40% MeOH for 20 min.) to yield mg of (1S)-2-[(2,6-dichlorophenyl)acetyl]-N,1-dimethyl-2,3-dihydro-1H-isoindole-4-sulfonamide 24 as a white solid.

Yield: 25%.

LC-MS (ES$^+$) 413/415/417 (M+H)$^+$.

Chiral analysis (LC, Chiralcel OD, 250*4.6 mm, 1 mL/min, 220 nm, 30° C., eluent: i-PrOH/n-heptane/DEA: 50/50/0.1): RT 5.37 min (other enantiomer at 8.14 min), 100% ee.

D.16. Synthesis of 2-[(2,6-dichlorophenyl)acetyl]-1-methyl-2,3-dihydro-1H-isoindole-5-carbonitrile, enantiomer A 25

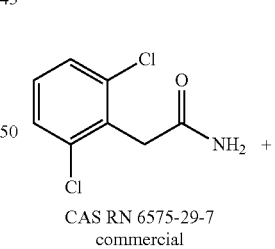

CAS RN 6575-29-7
commercial

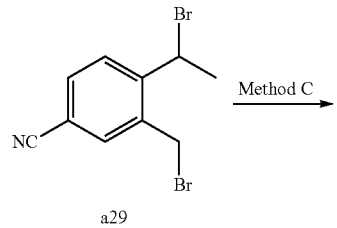

a29

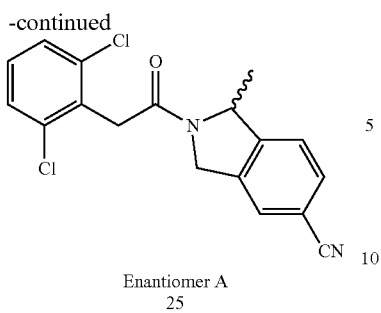

Enantiomer A
25

4-(1-Bromoethyl)-3-(bromomethyl)benzonitrile a29 (700 mg, 2.31 mmol) was dissolved in DMF (7 mL), 2-(2,6-dichlorophenyl)acetamide (475 mg, 2.31 mmol) was added and the resulting mixture cooled down to 0° C. NaH (60% in mineral oil, 185 mg, 4.62 mmol) was added and the reaction mixture was stirred at 0° C. during 30 min., then overnight at rt. EtOAc (100 mL) was added and the reaction mixture was washed with water (6×50 mL). The organic layer was dried over MgSO$_4$, filtered and concentrated under vacuum. The residue was triturated with MeOH (25 mL). The filtered solid was dried under vacuum. The residue was resolved by Chiral resolution (SFC, Chiralcel AD, 50*216 mm, 360 mL/min, 220 nm, 25° C., eluent: from 20% MeOH) to yield 35 mg of 2-[(2,6-dichlorophenyl)acetyl]-1-methyl-2,3-dihydro-1H-isoindole-5-carbonitrile, enantiomer A 25 as a white solid.

Yield: 4%.
LC-MS (ES$^+$) 345/347/349 (M+H)$^+$, 83.7% purity.
Chiral analysis (LC, Chiralcel AD-H, 250*4.6 mm, 1 mL/min, 220 nm, 30° C., eluent: EtOH/n-heptane/DEA: 50/50/0.1): RT 8.98 min (other enantiomer at 6.94 min), 97% ee.

D.17. Synthesis of 2-[2-chloro-6-(hydroxymethyl)phenyl]-1-[(1S)-1-methyl-1,3-dihydro-2H-isoindol-2-yl]ethanone 26

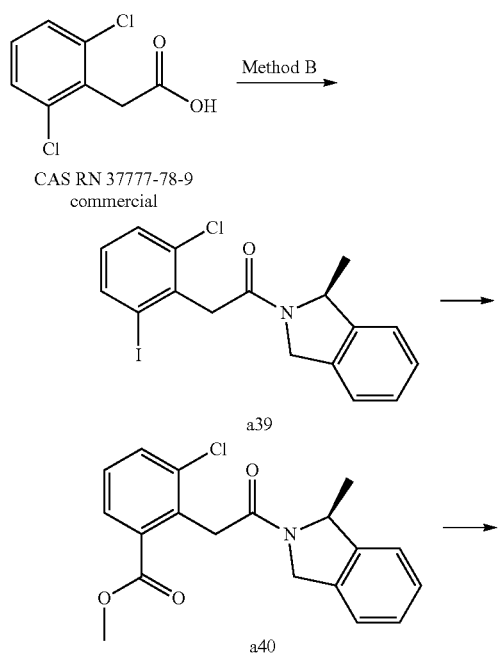

D.17.1. Synthesis of 2-(2-chloro-6-iodophenyl)-1-[(1S)-1-methyl-1,3-dihydro-2H-isoindol-2-yl]ethanone a39

Compound a39 may be synthesized according to a method analogous to Method B using (1S)-1-methyl-2,3-dihydro-1H-isoindole hydrochloride a22 and 2-(2-chloro-6-iodophenyl)acetic acid as starting material. Conditions: DCM, DIPEA (3 eq), rt, overnight.

Purification: column chromatography using from 0 to 4% MeOH in DCM as eluent.

Yield: 86%.
LCMS (ES$^+$): 412/414 (M+H)$^+$.

D.17.2. Synthesis of methyl 3-chloro-2-{2-[(1S)-1-methyl-1,3-dihydro-2H-isoindol-2-yl]-2-oxoethyl}benzoate a40

2-(2-Chloro-6-iodophenyl)-1-[(1S)-1-methyl-1,3-dihydro-2H-isoindol-2-yl]ethanone a39 (240 mg, 0.58 mmol) was dissolved in MeOH (10 mL) at rt. TEA (118 mg, 1.16 mmol) and ((S)-BINAP)PdBr$_2$ (41 mg, 0.08 mmol) were added. The mixture was placed under an atmosphere of carbon monoxide (8 Bars) at 60° C. for 5 h. The reaction mixture was filtered through Celite®, washed with MeOH and concentrated under vacuum. The residue was purified by column chromatography using 5% MeOH in DCM as eluent to yield 115 mg of methyl 3-chloro-2-{2-[(1S)-1-methyl-1,3-dihydro-2H-isoindol-2-yl]-2-oxoethyl}benzoate a40.

Yield: 57%.
LCMS (ES$^+$): 344/346 (M+H)$^+$.

D.17.3. Synthesis of 2-[2-chloro-6-(hydroxymethyl)phenyl]-1-[(1S)-1-methyl-1,3-dihydro-2H-isoindol-2-yl]ethanone 26

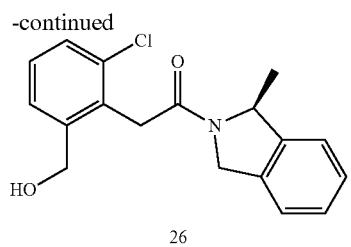

Methyl 3-chloro-2-{2-[(1S)-1-methyl-1,3-dihydro-2H-isoindol-2-yl]-2-oxoethyl}benzoate a40 (115 mg, 0.33 mmol) was dissolved in THF (8 mL), then lithium aluminium hydride (40 mg, 1 mmol) was added at 0° C. The mixture was stirred overnight at rt, then at 40° C. for 3 h. The reaction mixture was quenched with a 1N aqueous solution of HCl and extracted with DCM. The organic layer was washed twice with an aqueous saturated solution of NaHCO$_3$, dried over MgSO$_4$, filtered and concentrated under vacuum. The residue was purified by reverse phase chromatography (basic mode, LCMS prep) to yield 10 mg of 2-[2-chloro-6-(hydroxymethyl)phenyl]-1-[(1S)-1-methyl-1,3-dihydro-2H-isoindol-2-yl]ethanone 26 as a white solid.

Yield: 33%.
LCMS (ES$^+$): 316 (M+H)$^+$, 100% purity.

D.18. Syntheses of 2-(2,6-dichlorophenyl)-1-[(1R)-4-(hydroxymethyl)-1-methyl-1,3-dihydro-2H-isoindol-2-yl]ethanone 27 and 2-(2,6-dichlorophenyl)-1-[(1S)-4-(hydroxymethyl)-1-methyl-1,3-dihydro-2H-isoindol-2-yl]ethanone 28

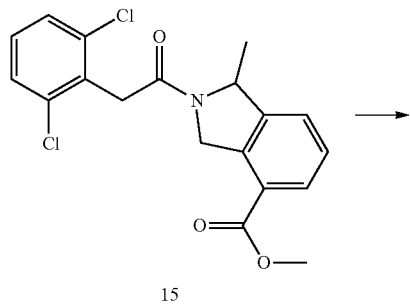

15

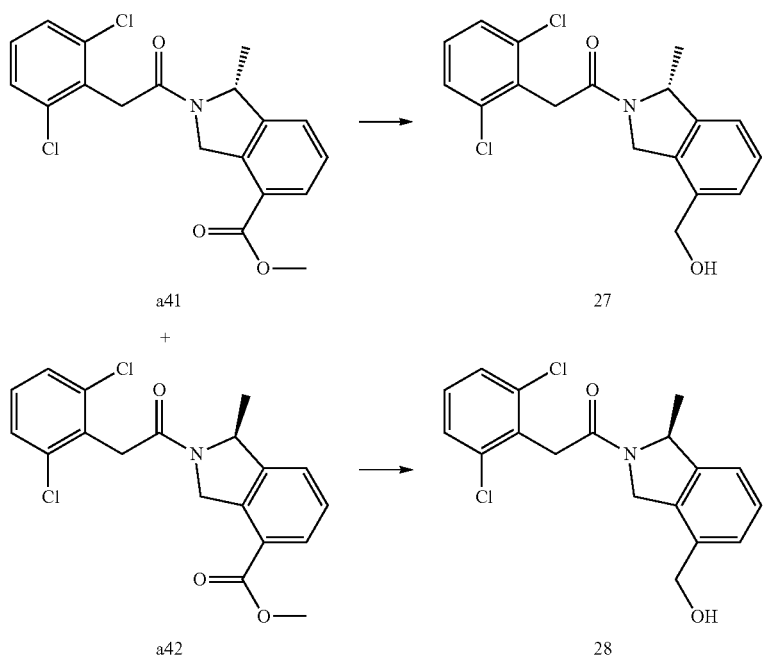

D.18.1. Synthesis of methyl (1R)-2-[(2,6-dichlorophenyl)acetyl]-1-methyl-2,3-dihydro-1H-isoindole-4-carboxylate a41 and methyl (1S)-2-[(2,6-dichlorophenyl)acetyl]-1-methyl-2,3-dihydro-1H-isoindole-4-carboxylate a42

Chiral resolution (SFC, Chiralpak AS, 50*265 mm, 360 mL/min, 220 nm, 40° C., eluent: 20% MeOH) of 1.26 g of methyl 2-[(2,6-dichlorophenyl)acetyl]-1-methyl-2,3-dihydro-1H-isoindole-4-carboxylate 15 afforded:

356 mg of methyl (1R)-2-[(2,6-dichlorophenyl)acetyl]-1-methyl-2,3-dihydro-1H-isoindole-4-carboxylate a41.
Yield: 32%.
LCMS (ES$^+$): 378/380/382 (M+H)$^+$.
Chiral analysis (LC, Chiralpak AS-H, 250*4.6 mm, 1 mL/min, 220 nm, 30° C., eluent: EtOH/DEA 100/0.1): RT 4.14 min, 99.2% ee.

276 mg of methyl (1S)-2-[(2,6-dichlorophenyl)acetyl]-1-methyl-2,3-dihydro-1H-isoindole-4-carboxylate a42.
Yield: 25%.
LCMS (ES$^+$): 378/380/382 (M+H)$^+$.
Chiral analysis (LC, Chiralpak AS-H, 250*4.6 mm, 1 mL/min, 220 nm, 30° C., eluent: EtOH/DEA 100/0.1): RT 7.84 min, 93.8% ee.

D.18.2. Synthesis of 2-(2,6-dichlorophenyl)-1-[(1R)-4-(hydroxymethyl)-1-methyl-1,3-dihydro-2H-isoindol-2-yl]ethanone 27

Methyl (1R)-2-[(2,6-dichlorophenyl)acetyl]-1-methyl-2,3-dihydro-1H-isoindole-4-carboxylate a41 (356 mg, 0.94 mmol) was dissolved in THF (5 mL). Lithium borohydride (20 mg, 0.92 mmol) was added. The mixture was stirred at rt for 48 h, then another equivalent of lithium borohydride (20 mg, 0.92 mmol) was added. The reaction mixture was quenched with a 0.5N aqueous solution of HCl and extracted thrice with DCM. The organic layer was dried over MgSO$_4$, filtered and concentrated under vacuum. The residue was purified by reverse phase chromatography to yield 110 mg of 2-(2,6-dichlorophenyl)-1-[(1R)-4-(hydroxymethyl)-1-methyl-1,3-dihydro-2H-isoindol-2-yl]ethanone 27 as a white solid.

Yield: 33%.
LCMS (ES$^+$): 350/352/354 (M+H)$^+$, 100% purity.

D.18.3. Synthesis of 2-(2,6-dichlorophenyl)-1-[(1S)-4-(hydroxymethyl)-1-methyl-1,3-dihydro-2H-isoindol-2-yl]ethanone 28

Methyl (1S)-2-[(2,6-dichlorophenyl)acetyl]-1-methyl-2,3-dihydro-1H-isoindole-4-carboxylate a42 (276 mg, 0.73 mmol) was dissolved in THF (5 mL). Lithium borohydride (17 mg, 0.78 mmol) was added. The mixture was stirred at rt for 48 h, then additional lithium borohydride (17 mg, 0.78 mmol) was added. The reaction mixture was quenched with a 0.5N aqueous solution of HCl and extracted thrice with DCM. The organic layer was dried over MgSO$_4$, filtered and concentrated under vacuum. The residue was purified by reverse phase chromatography to yield 100 mg of 2-(2,6-dichlorophenyl)-1-[(1S)-4-(hydroxymethyl)-1-methyl-1,3-dihydro-2H-isoindol-2-yl]ethanone 28 as a beige solid.

Yield: 39%.
LCMS (ES$^+$): 350/352/354 (M+H)$^+$, 100% purity.

D.19. Synthesis of 3,5-dichloro-4-{2-[(1S)-1-methyl-1,3-dihydro-2H-isoindol-2-yl]-2-oxoethyl}pyridin-2(1H)-one 29

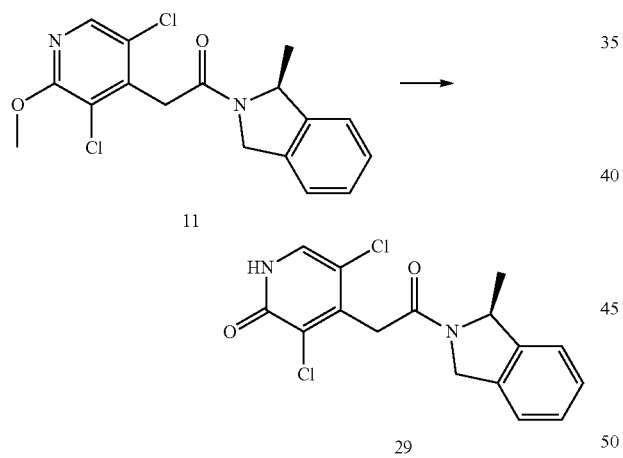

2-(3,5-Dichloro-2-methoxypyridin-4-yl)-1-[(1S)-1-methyl-1,3-dihydro-2H-isoindol-2-yl]ethanone 11 (100 mg, 0.28 mmol) was dissolved in ACN (10 mL). NaI (43 mg, 0.28 mmol) and chlorotrimethylsilane (42 µL, 0.28 mmol) were added. The mixture was stirred at rt overnight, then an additional amount of NaI (43 mg, 0.28 mmol) and chlorotrimethylsilane (42 µL, 0.28 mmol) was added. The mixture was stirred at rt for 3 days. The reaction mixture was concentrated under vacuum. The residue was purified by reverse phase chromatography (basic mode, LCMS prep). The crude material was triturated with Et$_2$O to yield 83 mg of 3,5-dichloro-4-{2-[(1S)-1-methyl-1,3-dihydro-2H-isoindol-2-yl]-2-oxoethyl}pyridin-2(1H)-one 29 as an beige solid.

Yield: 86%.
LCMS (ES$^+$): 337/339/341 (M+H)$^+$, 100% purity.

D.20. Synthesis of 2-(2,6-dichlorophenyl)-1-[1-methyl-4-(methylsulfonyl)-1,3-dihydro-2H-isoindol-2-yl]ethanone, enantiomer A 30

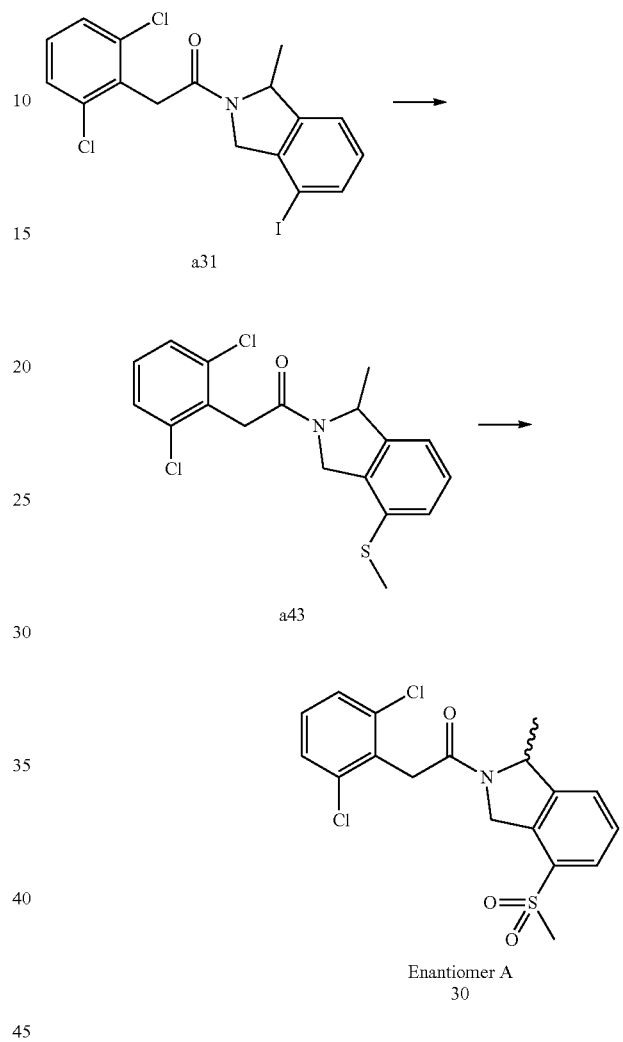

D.20.1. Synthesis of 2-(2,6-dichlorophenyl)-1-[1-methyl-4-(methylsulfanyl)-1,3-dihydro-2H-isoindol-2-yl]ethanone a43

2-(2,6-dichlorophenyl)-1-(4-iodo-1-methyl-1,3-dihydro-2H-isoindol-2-yl)ethanone a31 (250 mg, 0.56 mmol) was dissolved in toluene (20 mL). Sodium thiomethoxide (206 mg, 2.8 mmol), DIPEA (195 µL, 1.21 mmol), 4,5-bis(diphenylphosphino)-9,9-dimethylxanthene (32 mg, 56 µmol), tris(dibenzylideneacetone)dipalladium(0) (25 mg, 28 µmol) were added in a tube and the reaction mixture was stirred under microwave irradiations at 150° C. for 20 min. The reaction mixture was quenched with water and extracted thrice with DCM. The organic layer was dried on MgSO$_4$, filtered and concentrated under vacuum to yield 250 mg of 2-(2,6-dichlorophenyl)-1-[1-methyl-4-(methylsulfanyl)-1,3-dihydro-2H-isoindol-2-yl]ethanone a43 as a yellow solid which was used in next step without any further purification.

Yield: 121% (crude).
LCMS (ES$^+$): 366/368/370 (M+H)$^+$.

D.20.2. Synthesis of 2-(2,6-dichlorophenyl)-1-[1-methyl-4-(methylsulfonyl)-1,3-dihydro-2H-isoindol-2-yl]ethanone, enantiomer A 30

2-(2,6-dichlorophenyl)-1-[1-methyl-4-(methylsulfanyl)-1,3-dihydro-2H-isoindol-2-yl]ethanone a43 (205 mg, 0.56 mmol) was dissolved in chloroform (20 mL). 3-chloroperbenzoic acid (376 mg, 1.68 mmol) was added. The reaction mixture was stirred overnight at rt, quenched with an aqueous saturated solution of $NaHCO_3$ (20 mL) and extracted thrice with DCM. The organic layer was dried on $MgSO_4$, filtered and concentrated under vacuum. The residue was purified by reverse phase chromatography (Basic mode, standard LC), followed by chiral resolution SFC (Chiralpak AD, 50*216 mm, 360 mL/min, 220 nm, 40° C., eluent: 20% MeOH) to afford 39 mg of 2-(2,6-dichlorophenyl)-1-[1-methyl-4-(methylsulfonyl)-1,3-dihydro-2H-isoindol-2-yl]ethanone, enantiomer A 30 as a white solid.

Yield: 17%.
LCMS (ES$^+$): 398/400/402 (M+H)$^+$, 100% purity.
Chiral analysis (LC, Chiralpak AD-H, 250*4.6 mm, 1 mL/min, 220 nm, 30° C., eluent: nPrOH/n-heptane/DEA 50/50/0.1): RT 6.31 min (other enantiomer at 4.77 min), 100% ee.

D.21. Synthesis of 2-(2,6-dichlorophenyl)-1-[(1S)-1-methyl-4-(pyrrolidin-1-ylsulfonyl)-1,3-dihydro-2H-isoindol-2-yl]ethanone 31

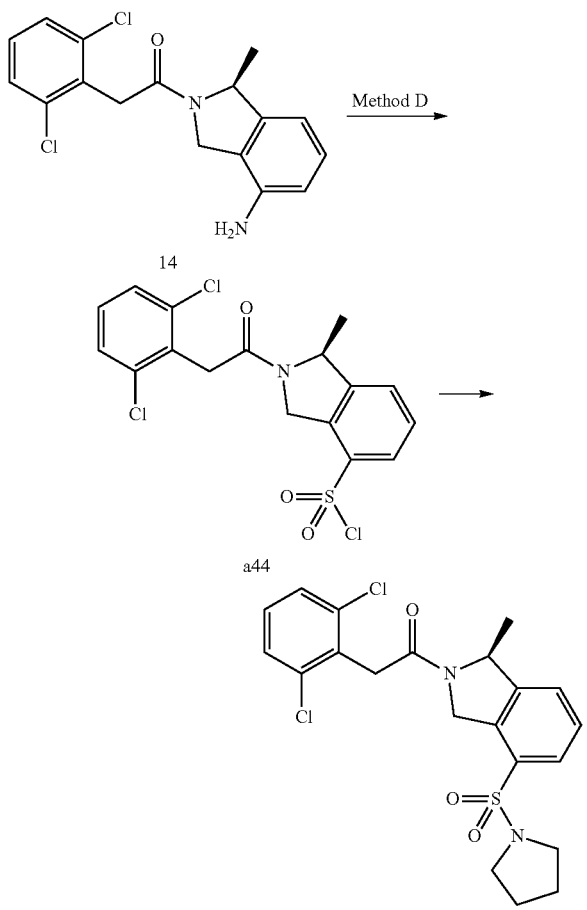

D.21.1. Synthesis of (1S)-2-[(2,6-dichlorophenyl)acetyl]-1-methyl-2,3-dihydro-1H-isoindole-4-sulfonyl chloride a44

Compound a44 may be synthesized according to method analogous to the method described in D.15.1. using 1-[(1S)-4-amino-1-methyl-1,3-dihydro-2H-isoindol-2-yl]-2-(2,6-dichlorophenyl)ethanone 14 as starting material.

Yield: 100% (crude).
LCMS (ES$^+$): 418/420/422 (M+H)$^+$.

D.21.2. Method E. Synthesis of 2-(2,6-dichlorophenyl)-1-[(1S)-1-methyl-4-(pyrrolidin-1-ylsulfonyl)-1,3-dihydro-2H-isoindol-2-yl]ethanone 31

A mixture of (1S)-2-[(2,6-dichlorophenyl)acetyl]-1-methyl-2,3-dihydro-1H-isoindole-4-sulfonyl chloride a44 (45 mg 0.11 mmol) and pyrrolidine (100 µL, 1.2 mmol) in chloroform (500 µL) was stirred at rt for 15 min. The reaction mixture was then diluted with DCM (5 mL) and washed with a 1N aqueous solution of HCl (3 mL). The organic layer was dried over $MgSO_4$, filtered and concentrated under vacuum. The residue was purified by reverse phase chromatography (basic mode, LCMS prep) to afford 49 mg of 2-(2,6-dichlorophenyl)-1-[(1S)-1-methyl-4-(pyrrolidin-1-ylsulfonyl)-1,3-dihydro-2H-isoindol-2-yl]ethanone 31 as an off-white solid.

Yield: 100%.
LCMS (ES$^+$): 453/455/457 (M+H)$^+$, 89.8% purity.
Compounds 32, 33, 34, 35, 36, 37, 38 and 39 may be synthesized according to a method analogous to Method E.

2-(2,6-dichlorophenyl)-1-[(1S)-1-methyl-4-(piperidin-1-ylsulfonyl)-1,3-dihydro-2H-isoindol-2-yl]ethanone 32

Compound 32 was synthesized using (1S)-2-[(2,6-dichlorophenyl)acetyl]-1-methyl-2,3-dihydro-1H-isoindole-4-sulfonyl chloride a44 and piperidine as starting materials.

Yield: 29%.
LCMS (ES$^+$): 467/469/471 (M+H)$^+$, 90% purity.
Appearance: brown solid.

1-[(1S)-4-(azetidin-1-ylsulfonyl)-1-methyl-1,3-dihydro-2H-isoindol-2-yl]-2-(2,6-dichlorophenyl)ethanone 33

Compound 33 was synthesized using (1S)-2-[(2,6-dichlorophenyl)acetyl]-1-methyl-2,3-dihydro-1H-isoindole-4-sulfonyl chloride a44 and azetidine as starting material.

Yield: 25%.
LCMS (ES$^+$): 439/441/443 (M+H)$^+$, 99% purity.
Appearance: off-white solid.

(1S)-2-[(2,6-dichlorophenyl)acetyl]-1-methyl-N-(propan-2-yl)-2,3-dihydro-1H-isoindole-4-sulfonamide 34

Compound 34 was synthesized using (1S)-2-[(2,6-dichlorophenyl)acetyl]-1-methyl-2,3-dihydro-1H-isoindole-4-sulfonyl chloride a44 and isopropylamine as starting materials.

Yield: 16%.
LCMS (ES$^+$) 441/443/445 (M+H)$^+$, 100% purity.
Appearance: off-white solid.

(1S)-2-[(2,6-dichlorophenyl)acetyl]-N-ethyl-1-methyl-2,3-dihydro-1H-isoindole-4-sulfonamide 35

Compound 35 was synthesized using (1S)-2-[(2,6-dichlorophenyl)acetyl]-1-methyl-2,3-dihydro-1H-isoindole-4-sulfonyl chloride a44 and ethylamine as starting material.

Yield: 24%.

LCMS (ES+): 427/429/431 (M+H)+, 92% purity.

Appearance: yellow solid.

(1S)-2-[(2,6-dichlorophenyl)acetyl]-1-methyl-N-(2,2,2-trifluoroethyl)-2,3-dihydro-1H-isoindole-4-sulfonamide 36

Compound 36 was synthesized using (1S)-2-[(2,6-dichlorophenyl)acetyl]-1-methyl-2,3-dihydro-1H-isoindole-4-sulfonyl chloride a44 and 2,2,2-trifluoroethylamine as starting material.

Yield: 9%.

LCMS (ES+): 481/483/485 (M+H)+, 85% purity.

Appearance: yellow solid.

(1S)-2-[(2,6-dichlorophenyl)acetyl]-1-methyl-N-(1-methyl-1H-pyrazol-3-yl)-2,3-dihydro-1H-isoindole-4-sulfonamide 37

Compound 37 was synthesized using (1S)-2-[(2,6-dichlorophenyl)acetyl]-1-methyl-2,3-dihydro-1H-isoindole-4-sulfonyl chloride a44 and 1-methyl-1H-pyrazol-3-amine as starting materials.

Yield: 11%.

LCMS (ES+): 479/481/483 (M+H)+, 88% purity.

Appearance: yellow solid.

(1S)-2-[(2,6-dichlorophenyl)acetyl]-1-methyl-N-(4H-1,2,4-triazol-3-yl)-2,3-dihydro-1H-isoindole-4-sulfonamide 38

Compound 38 was synthesized using (1S)-2-[(2,6-dichlorophenyl)acetyl]-1-methyl-2,3-dihydro-1H-isoindole-4-sulfonyl chloride a44 and 4H-1,2,4-triazol-3-amine as starting materials.

Yield: 16%.

LCMS (ES+): 466/468/470 (M+H)+, 95% purity.

Appearance: off-white solid.

(1S)-2-[(2,6-dichlorophenyl)acetyl]-1-methyl-N-(1-methyl-1H-pyrazol-5-yl)-2,3-dihydro-1H-isoindole-4-sulfonamide 39

Compound 39 was synthesized using (1S)-2-[(2,6-dichlorophenyl)acetyl]-1-methyl-2,3-dihydro-1H-isoindole-4-sulfonyl chloride a44 and 1-methyl-1H-pyrazol-5-ylamine as starting material.

Yield: 9%.

LCMS (ES+) 479/481/483 (M+H)+, 90% purity.

Appearance: White solid.

D.22. Synthesis of N-({2-[(2,6-dichlorophenyl)acetyl]-1-methyl-2,3-dihydro-1H-isoindol-4-yl}methyl)methanesulfonamide 40

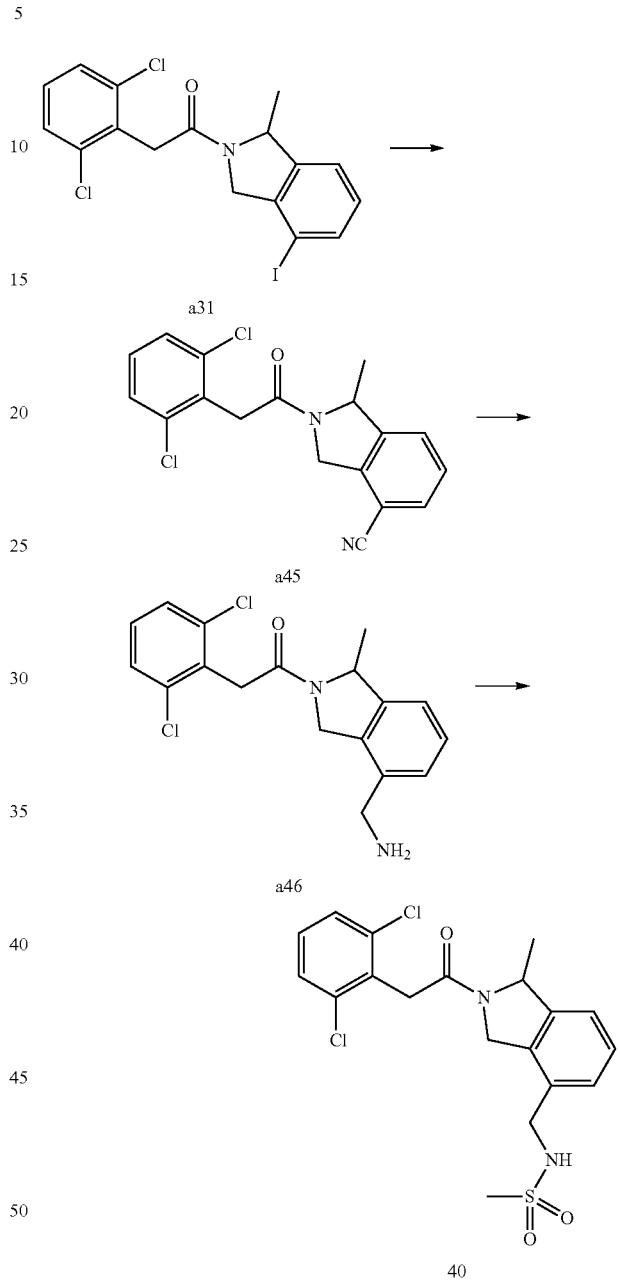

D.22.1. Synthesis of 2-[(2,6-dichlorophenyl)acetyl]-1-methyl-2,3-dihydro-1H-isoindole-4-carbonitrile a45

2-(2,6-Dichlorophenyl)-1-(4-iodo-1-methyl-1,3-dihydro-2H-isoindol-2-yl)ethanone a31 (500 mg, 1.12 mmol) was dissolved in DMF (5 mL), then zinc cyanide (136 mg, 1.12 mmol), tetrakis(triphenylphosphine)palladium(0) (131 mg, 0.11 mmol). The reaction mixture was stirred under microwave irradiations at 120° C. for 20 min, quenched with an aqueous saturated solution of NaHCO₃ (20 mL) and extracted thrice with DCM. The organic layer was dried on MgSO₄, filtered and concentrated under vacuum. The residue was purified by reverse phase chromatography (basic mode, standard LC) to afford 231 mg of 2-[(2,6-dichlorophenyl)acetyl]-1-methyl-2,3-dihydro-1H-isoindole-4-carbonitrile a45 as a white solid.

Yield: 60%.
LCMS (ES⁺): 345/347/349 (M+H)⁺.

D.22.2. Synthesis of 1-[4-(aminomethyl)-1-methyl-1,3-dihydro-2H-isoindol-2-yl]-2-(2,6-dichlorophenyl)ethanone a46

In an autoclave, 2-[(2,6-dichlorophenyl)acetyl]-1-methyl-2,3-dihydro-1H-isoindole-4-carbonitrile a45 (231 mg, 0.67 mmol) was dissolved in EtOH (25 mL). Raney®—Nickel (28 mg, 0.33 mmol) was added and the mixture was stirred under hydrogen pressure (5 bars). The reaction mixture was filtered through Celite®, rinsed with EtOH (20 mL) and concentrated under vacuum. The residue was purified by reverse phase chromatography (basic mode, standard LC) to afford 76 mg of 1-[4-(aminomethyl)-1-methyl-1,3-dihydro-2H-isoindol-2-yl]-2-(2,6-dichlorophenyl)ethanone a46 as a white solid.

Yield: 32%.
LCMS (ES⁺) 349/351/353 (M+H)⁺.

D.22.3. Synthesis of N-({2-[(2,6-dichlorophenyl)acetyl]-1-methyl-2,3-dihydro-1H-isoindol-4-yl}methyl)methanesulfonamide 40

1-[4-(aminomethyl)-1-methyl-1,3-dihydro-2H-isoindol-2-yl]-2-(2,6-dichlorophenyl)ethanone a46 (76 mg, 0.22 mmol) was dissolved in THF (5 mL). TEA (93 µL, 0.66 mmol) was added at 0° C. and the mixture was stirred at 0° C. for 5 min. Methanesulfonyl chloride (26 µL, 0.33 mmol) was added dropwise at 0° C. The reaction mixture was at rt for 1 h., quenched with an aqueous saturated solution of NaHCO₃ (20 mL) and extracted thrice with DCM. The organic layer was dried over MgSO₄, filtered and concentrated under vacuum. The residue was purified by reverse phase chromatography (basic mode, standard LC) to afford 70 mg of N-({2-[(2,6-dichlorophenyl)acetyl]-1-methyl-2,3-dihydro-1H-isoindol-4-yl}methyl)methanesulfonamide 40 as a white solid.

Yield: 74%.
LCMS (ES⁺): 427/429/431 (M+H)⁺, 96.5% purity.

D.23. Synthesis of N-(2,4-dichloro-3-{2-[(1S)-1-methyl-1,3-dihydro-2H-isoindol-2-yl]-2-oxoethyl}benzyl)methanesulfonamide 41

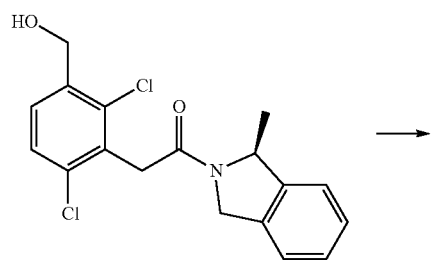

17

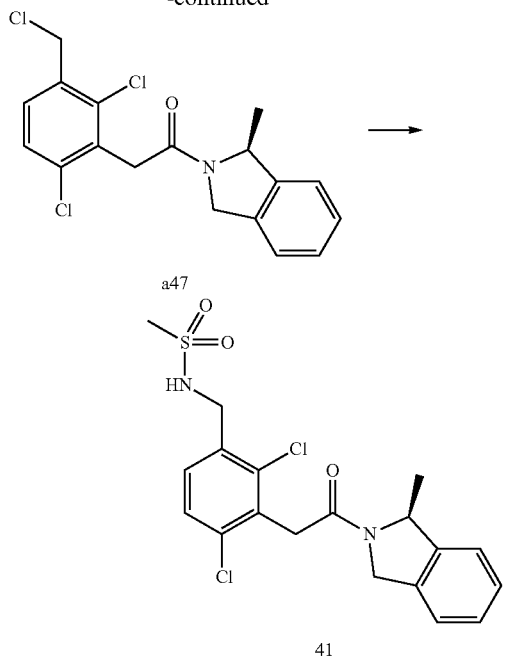

D.23.1. Synthesis of 2-[2,6-dichloro-3-(chloromethyl)phenyl]-1-[(1S)-1-methyl-1,3-dihydro-2H-isoindol-2-yl]ethanone a47

2-[2,6-dichloro-3-(hydroxymethyl)phenyl]-1-[(1S)-1-methyl-1,3-dihydro-2H-isoindol-2-yl]ethanone 17 (93 mg, 0.26 mmol) was dissolved in DCM (2 mL) at rt, then para-toluenesulfonyl chloride (81 mg, 0.42 mmol) and DIPEA (71 µL, 0.53 mmol) were added. The mixture was stirred at 150° C. for 1 h, cooled to rt, quenched with water, then extracted thrice with DCM. The organic layer was washed with an aqueous saturated solution of NaHCO₃, dried over Na₂SO₄, filtered and concentrated under vacuum to afford 100 mg of 2-[2,6-dichloro-3-(chloromethyl)phenyl]-1-[(1S)-1-methyl-1,3-dihydro-2H-isoindol-2-yl]ethanone a47 which was used in next step without any further purification.

Yield: 104% (crude).
LCMS (ES⁺): 368/370/372 (M+H)⁺.

D.23.2. Synthesis of N-(2,4-dichloro-3-{2-[(1S)-1-methyl-1,3-dihydro-2H-isoindol-2-yl]-2-oxoethyl}benzyl)methanesulfonamide 41

Methanesulfonamide (27 mg, 0.28 mmol) was dissolved in DMF (1 mL) at rt, then sodium hydride (60% in mineral oil), 12 mg, 0.3 mmol) was added at 0° C. and the mixture was stirred at rt for 1.5 h. 2-[2,6-Dichloro-3-(chloromethyl)phenyl]-1-[(1S)-1-methyl-1,3-dihydro-2H-isoindol-2-yl]ethanone a47 (100 mg, 0.27 mmol) was added at 0° C. The reaction mixture was stirred at rt for 160 h, quenched with an aqueous solution of NaHCO₃ and extracted thrice with EtOAc. The organic layer was washed with brine, dried over Na₂SO₄, filtered and concentrated under vacuum. The residue was purified reverse phase chromatography (basic mode, LCMS prep) to yield 20 mg of N-(2,4-dichloro-3-{2-[(1S)-1-methyl-1,3-dihydro-2H-isoindol-2-yl]-2-oxoethyl}benzyl)methanesulfonamide 41 as a beige solid foam.

Yield: 17%.
LCMS (ES⁺): 427/429/431 (M+H)⁺, 100% purity.

D.24. Synthesis of 2-(2,6-dichlorophenyl)-1-{(1S)-1-methyl-4-[(tetrahydro-2H-pyran-4-ylmethyl)sulfonyl]-1,3-dihydro-2H-isoindol-2-yl}ethanone 42

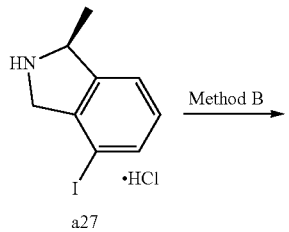

a27

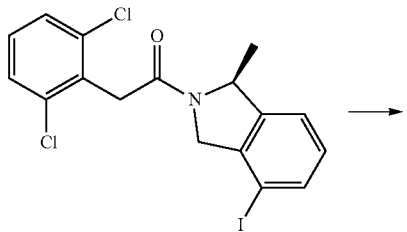

a48

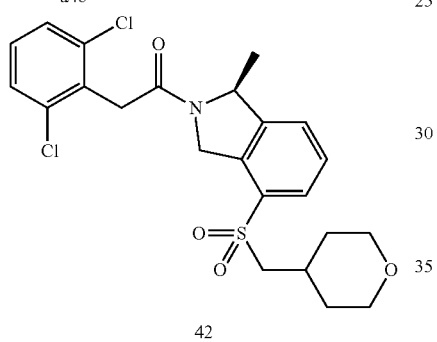

42

D.24.1. Synthesis of 2-(2,6-dichlorophenyl)-1-[(1S)-4-iodo-1-methyl-1,3-dihydro-2H-isoindol-2-yl]ethanone a48

Compound a48 may be synthesized according to a method analogous to Method B using (1S)-4-iodo-1-methyl-2,3-dihydro-1H-isoindole hydrochloride a27 and (2,6-dichlorophenyl)acetic acid as starting material. Conditions: DMF, TEA (3 eq), rt, 1 h. The crude compound was directly used in next step without any further purification.

Yield: 96% (crude).

LCMS (ES$^1$): 446/448/450 (M+H)$^1$.

D.24.2. Synthesis of 2-(2,6-dichlorophenyl)-1-{(1S)-1-methyl-4-[(tetrahydro-2H-pyran-4-ylmethyl)sulfonyl]-1,3-dihydro-2H-isoindol-2-yl}ethanone 42

2-(2,6-dichlorophenyl)-1-[(1S)-4-iodo-1-methyl-1,3-dihydro-2H-isoindol-2-yl]ethanone a48 (100 mg, 0.22 mmol), sodium metabisulfite (87 mg, 0.45 mmol), tetrabutylammonium bromide (80 mg, 0.25 mmol), sodium formate (34 mg, 0.49 mmol), palladium(II) acetate (5 mg, 0.02 mmol), 1,10-phenanthroline (12 mg, 0.07 mmol) and triphenylphosphine (18 mg, 0.07 mmol) were mixed in DMSO (2 mL). The mixture was stirred at 70° C. for 2 h. The reaction mixture was cooled to rt, then 4-(iodomethyl)tetrahydro-2H-pyran (100 mg, 0.44 mmol) was added. The mixture was stirred at rt for 16 h, then diluted with DCM (50 mL) and successively washed with water (50 mL) and brine (50 mL). The organic layer was dried over MgSO$_4$, filtered and concentrated under vacuum. The residue was purified by reverse phase chromatography (basic mode, LCMS prep) to yield 12 mg of 2-(2,6-dichlorophenyl)-1-{(1S)-1-methyl-4-[(tetrahydro-2H-pyran-4-ylmethyl)sulfonyl]-1,3-dihydro-2H-isoindol-2-yl}ethanone 42 as a white solid.

Yield: 10%.

LCMS (ES$^+$) 482/484/486 (M+H)$^+$, 96.78% purity.

D.25. Synthesis of 2-(2,6-dichlorophenyl)-1-[(1S)-4-{[dimethyl(oxido)-λ$^6$-sulfanylidene]amino}-1-methyl-1,3-dihydro-2H-isoindol-2-yl]ethanone 45

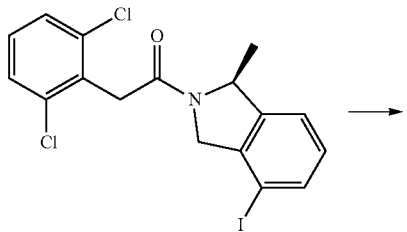

a48

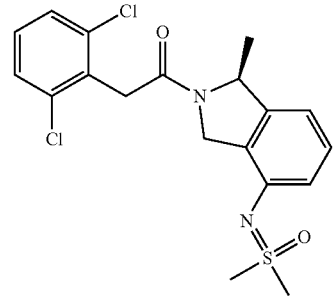

45

2-(2,6-dichlorophenyl)-1-[(1S)-4-iodo-1-methyl-isoindolin-2-yl]ethanone a48 (100 mg, 0.22 mmol), cesium carbonate (109 mg, 0.33 mmol), palladium(II) acetate (5 mg, 22 μmol), (+/−)-2,2'-bis(diphenylphosphino)-1,1'-binaphthyl (21 mg, 33 μmol), (dimethanesulfinylidene) amine (commercial, 26 mg, 0.27 mmol) were mixed in toluene (2 mL) in a sealed tube. The mixture was stirred overnight at 110° C. The reaction mixture was quenched with water (50 mL) and extracted with EtOAc (3×50 mL). The organic layer was dried over MgSO$_4$, filtered and concentrated under vacuum. The residue was purified by reverse phase chromatography (basic mode, LCMS prep) to yield 56 mg of 2-(2,6-dichlorophenyl)-1-[(1S)-4-{[dimethyl(oxido)-λ$^6$-sulfanylidene]amino}-1-methyl-1,3-dihydro-2H-isoindol-2-yl]ethanone 45 as a white solid.

Yield: 61%.

LCMS (ES$^+$): 411/413/415 (M+H)$^+$, 100% purity.

D.26. Synthesis of 2-(2,6-dichlorophenyl)-1-[(1S)-1-methyl-4-(1H-pyrazol-4-yl)-1,3-dihydro-2H-isoindol-2-yl]ethanone 46

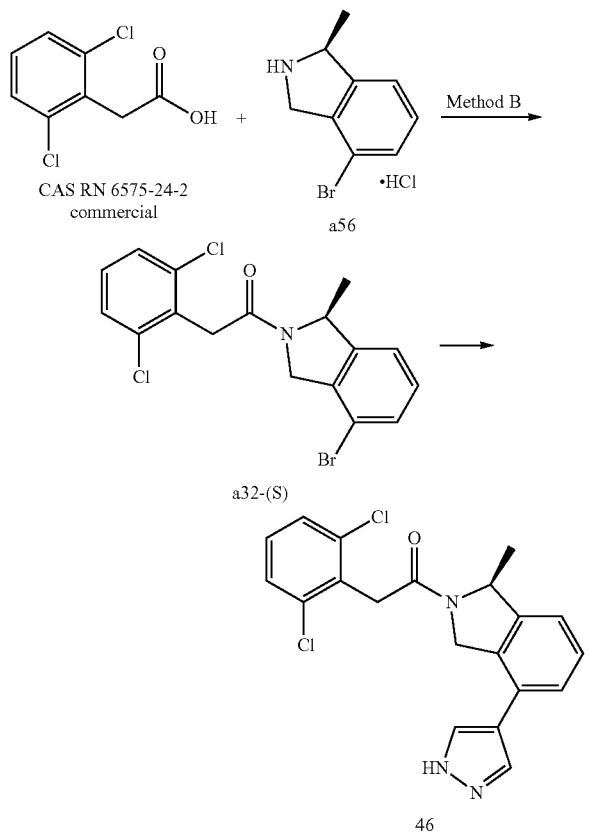

D.26.1. Synthesis of 1-[(1S)-4-bromo-1-methyl-isoindolin-2-yl]-2-(2,6-dichlorophenyl)ethanone a32-(S)

Compound a32-(S) may be synthesized according to a method analogous to Method B using (1S)-4-bromo-1-methyl-isoindoline hydrochloride a56 and (2,6-dichlorophenyl)acetic acid as starting materials. Conditions: DCM, DIPEA (3 equiv), rt, overnight. Purification: column chromatography using from 0 to 1% MeOH in DCM as eluent.
Yield: 98%.
LCMS (ES+): 399/401/403 (M+H)+, 94% purity.

D.26.2. Synthesis of 2-(2,6-dichlorophenyl)-1-[(1S)-1-methyl-4-(1H-pyrazol-4-yl)-1,3-dihydro-2H-isoindol-2-yl]ethanone 46

1-[(1S)-4-bromo-1-methyl-isoindolin-2-yl]-2-(2,6-dichlorophenyl)ethanone a32-(S) (50 mg, 0.12 mmol), 1-boc-pyrazole-4-boronic acid pinacol ester (57 mg, 0.19 mmol) and K$_2$CO$_3$ (52 mg, 0.37 mmol) were dissolved in 1,4-dioxane (3 mL) in a tube. Tetrakis(triphenylphosphine)palladium(0) (12 mg, 0.01 mmol) and water (0.3 mL) were added. The tube was sealed and heated at 130° C. during 1 h under microwave irradiation. The reaction mixture was concentrated under vacuum. The residue was diluted with EtOAc, sonicated, stirred, filtered, washed twice with EtOAc then concentrated under vacuum. The residue was purified by reverse phase chromatography (basic mode, standard LC) to yield mg of 2-(2,6-dichlorophenyl)-1-[(1S)-1-methyl-4-(1H-pyrazol-4-yl)-1,3-dihydro-2H-isoindol-2-yl]ethanone 46 as a white solid.
Yield: 54%.
LCMS (ES+): 386/388/390 (M+H)+, 100% purity.

D.27. Synthesis of 2-(5-chloro-1H-indol-4-yl)-1-[(1S)-1-methyl-1,3-dihydro-2H-isoindol-2-yl]ethanone 47

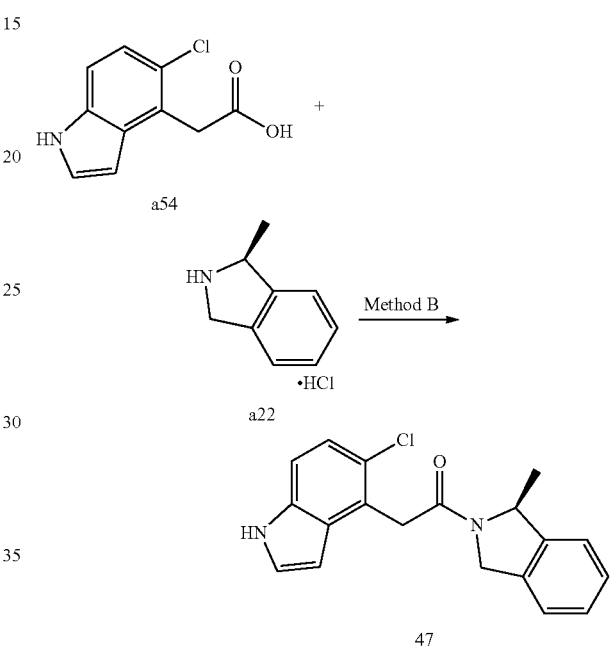

Compound 47 may be synthesized according to a method analogous to Method B using 2-(5-chloro-1H-indol-4-yl)acetic acid a54 and (1S)-1-methyl-2,3-dihydro-1H-isoindole hydrochloride a22 as starting materials. Conditions: DCM, Et$_3$N (3 equiv), rt, overnight. Purification: reverse phase chromatography (basic mode, LCMS prep).
Yield: 10%.
LCMS (ES+): 325/327 (M+H)+, 95% purity.

D.28. Synthesis of 3-chloro-2-[2-[(1S)-1-methyl-4-[(1R)-2,2,2-trifluoro-1-hydroxy-ethyl]isoindolin-2-yl]-2-oxo-ethyl]benzonitrile isomer A 48 and isomer B 49

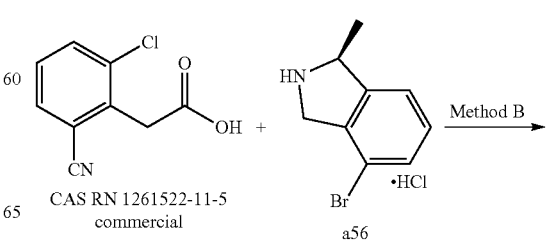

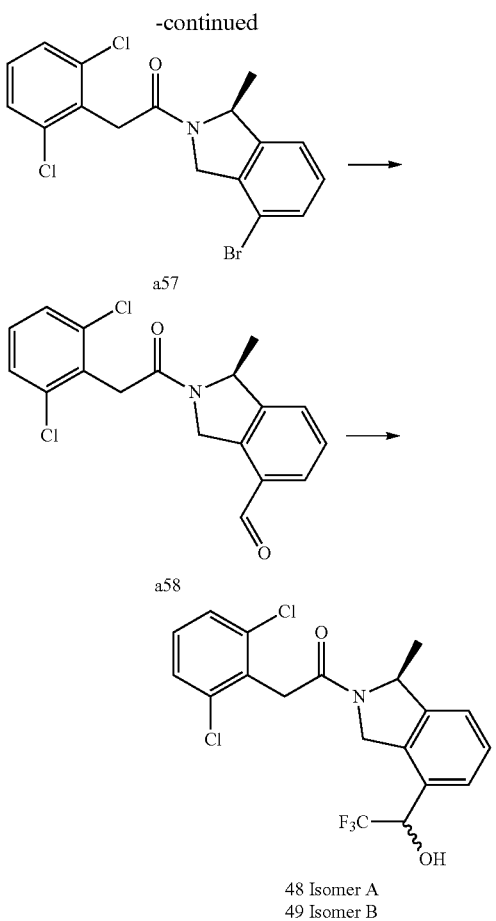

a57 a58

48 Isomer A
49 Isomer B

D.28.1. Synthesis of 2-[2-[(1S)-4-bromo-1-methyl-isoindolin-2-yl]-2-oxo-ethyl]-3-chloro-benzonitrile a57

Compound a57 may be synthesized according to a method analogous to Method B using 2-(2-chloro-6-cyano-phenyl) acetic acid and (1S)-4-bromo-1-methyl-isoindoline hydrochloride a56 and as starting materials. Conditions: DMAC, DIPEA (3 equiv), rt, overnight. Purification: column chromatography using from 0 to 1% MeOH in DCM as eluent.
Yield: 98%.
HPLC (Basic Mode): RT 5.82 min, 100% purity.

D.28.2. Synthesis of 3-chloro-2-[2-[(1S)-4-formyl-1-methyl-isoindolin-2-yl]-2-oxo-ethyl]benzonitrile a58

To a suspension of 2-[2-[(1S)-4-bromo-1-methyl-isoindolin-2-yl]-2-oxo-ethyl]-3-chloro-benzonitrile a57 (427 mg, 1.09 mmol) in toluene (15 mL) in an autoclave were added N,N,N',N'-tetramethylethylenediamine (340 μL, 2.21 mmol), butyldi-1-adamantylphosphine (62 mg, 0.17 mmol) and palladium(II)acetate (12 mg, 0.05 mmol). The reactor was flushed with nitrogen and placed under 5 bar of Syngas (CO/H$_2$ 1:1). The reaction mixture was heated at 120° C. for 6 h, then filtered through a pad of Celite®. The filtrate was washed with water (2×50 mL). The organic layer was dried over MgSO$_4$, filtered and concentrated under vacuum. The residue was purified by reverse phase chromatography (Basic mode, standard LC) to yield 189 mg of 3-chloro-2-[2-[(1S)-4-formyl-1-methyl-isoindolin-2-yl]-2-oxo-ethyl]benzonitrile a58 which was used in the next step without any further purification.
Yield: 51% (crude).
LCMS (ES$^+$): 339/341 (M+H)$^+$.

D.28.3. Synthesis of 3-chloro-2-[2-[(1S)-1-methyl-4-[-2,2,2-trifluoro-1-hydroxy-ethyl]isoindolin-2-yl]-2-oxo-ethyl]benzonitrile isomer A 48 and isomer B 49

To a solution of 3-chloro-2-[2-[(1S)-4-formyl-1-methyl-isoindolin-2-yl]-2-oxo-ethyl]benzonitrile a58 (189 mg, 0.56 mmol) in DMF (10 mL) were added cesium fluoride (173 mg, 1.12 mmol) and (trifluoromethyl)trimethylsilane (165 μL, 1.12 mmol). The reaction mixture was stirred overnight at 50° C., then quenched with an aqueous saturated solution of NaHCO$_3$ (50 mL) and extracted with EtOAc (3×30 mL). The organic layer was dried over MgSO$_4$, filtered and concentrated under vacuum. The residue was purified by reverse phase chromatography (basic mode, standard LC) to afford the racemate 3-chloro-2-[2-[(1S)-1-methyl-4-[2,2,2-trifluoro-1-hydroxy-ethyl]isoindolin-2-yl]-2-oxo-ethyl]benzonitrile.

Chiral resolution (SFC, Lux-Cell-2, 50*257 mm, 360 mL/min, 220 nm, 25° C., eluent: from 20 to 40% MeOH) afforded:
 38 mg of 3-chloro-2-[2-[(1S)-1-methyl-4-[2,2,2-trifluoro-1-hydroxy-ethyl]isoindolin-2-yl]-2-oxo-ethyl]benzonitrile isomer A 48 as a yellow oil.
Yield: 17%.
LCMS (ES$^+$): 409/411 (M+H)$^+$, 91% purity.
Chiral analysis (LC, Lux-Cell-2, 250*4.6 mm, 1 mL/min, 220 nm, 30° C., eluent: iPrOH/n-heptane/DEA 50/50/0.1): RT 4.97 min, 100% ee.—55 mg of 3-chloro-2-[2-[(1S)-1-methyl-4-[2,2,2-trifluoro-1-hydroxy-ethyl]isoindolin-2-yl]-2-oxo-ethyl]benzonitrile isomer B 49 as a brown solid.
Yield: 33%.
LCMS (ES$^+$): 409/411 (M+H)$^+$, 93% purity.
Chiral analysis (LC, Lux-Cell-2, 250*4.6 mm, 1 mL/min, 220 nm, 30° C., eluent: iPrOH/n-heptane/DEA 50/50/0.1): RT 7.71 min, 100% ee.

Example E. Synthesis of Compounds of Formula I-B

E.1. Synthesis of (1S)—N-(2,6-dichlorophenyl)-1-methyl-1,3-dihydro-2H-isoindole-2-carboxamide 43

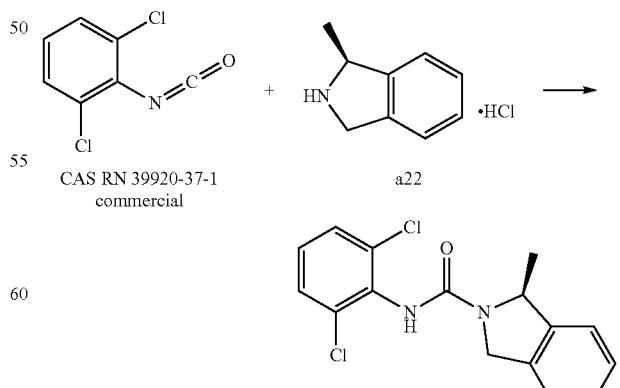

CAS RN 39920-37-1
commercial a22

43

(1S)-1-Methyl-2,3-dihydro-1H-isoindole hydrochloride a22 (848 mg, 5 mmol), 1,3-dichloro-2-isocyanatobenzene (commercial, 959 mg, 5 mmol) and TEA (2.1 mL, 15 mmol) were mixed in DCM (50 mL). The reaction mixture was stirred at rt for 60 h, then diluted with DCM (500 mL) and successively washed with water (250 mL), a 1N aqueous solution of HCl (250 mL) and an aqueous saturated solution of sodium carbonate (250 mL). The organic layer was dried over MgSO$_4$, filtered and concentrated under vacuum. The residue was purified by reverse phase chromatography (basic mode, standard LC). Chiral resolution (LC, Chiralcel OJ, 50*450 nm, 80 mL/min, 220 nm, 30° C., eluent: iPrOH/n-heptane: 30/70) yielded 900 mg of (1S)—N-(2,6-dichlorophenyl)-1-methyl-1,3-dihydro-2H-isoindole-2-carboxamide 43 as a white solid.

Yield: 56%.

LCMS (ES$^+$): 321/323/325 (M+H)$^+$, 95.2% purity.

Chiral analysis (LC, Chiralcel OJ-H, 250*4.6 mm, 1 mL/min, 220 nm, 30° C., eluent: iPrOH/n-heptane/DEA 30/70/0.1): RT 6.80 min (other enantiomer 9.86 min), 100% ee.

NMR (400 MHz, DMSO-d$_6$) δ: 8.31 (s, 1H), 7.52 (d, J=8.1 Hz, 2H), 7.33 (m, 5H), 5.19 (m, 1H), 4.76 (m, 2H), 1.48 (m, 3H).

E.2. Synthesis of (1S)—N-(2-chloro-6-methylphenyl)-1-methyl-1,3-dihydro-2H-isoindole-2-carboxamide 44

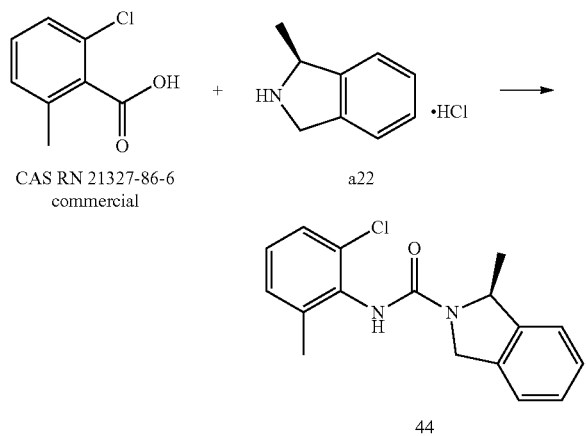

(1S)-1-Methyl-2,3-dihydro-1H-isoindole hydrochloride a22 (96 mg, 0.57 mmol), 2-chloro-6-methylbenzoic acid (commercial, 100 mg, 0.57 mmol), TEA (238 μL, 1.71 mmol), diphenylphosphoryl azide (176 mg, 0.63 mmol) were mixed in toluene (3 mL). The mixture was stirred at 120° C. for 4 h. The reaction mixture was then diluted with Et$_2$O (50 mL) and successively washed with water (20 mL), a 1N aqueous solution of HCl (20 mL), an aqueous saturated solution of sodium carbonate (20 mL) and brine (20 mL). The organic layer was dried over MgSO$_4$, filtered and concentrated under vacuum. The residue was purified by crystallization in Et$_2$O to yield 30 mg of (1S)—N-(2-chloro-6-methylphenyl)-1-methyl-1,3-dihydro-2H-isoindole-2-carboxamide 44 as a white solid.

Yield: 18%.

LCMS (ES$^+$): 301/303/305 (M+H)$^+$, 94.7% purity.

$^1$H NMR (400 MHz, DMSO-d$_6$) δ 8.00 (s, 1H), 7.34 (m, 5H), 7.21 (m, 2H), 5.20 (d, J=5.7 Hz, 1H), 4.77 (m, 2H), 2.25 (s, 3H), 1.48 (d, J=6.2 Hz, 3H).

E. cAMP HTRF Assay

Compounds according to the present invention do not directly activate the dopamine D1 receptor, but potentiate the effect of D1 agonists or the endogenous ligand on D1 receptors, dopamine, through an allosteric mechanism, and are therefore D1 positive allosteric modulators (D1 PAM).

Dopamine and other D1 agonists directly activate the dopamine D1 receptor by themselves.

The present assay allows to measure respectively the effects of compounds of the Examples in the absence of dopamine ("activation assay") and the effects of compounds of the Examples in the presence of dopamine ("potentiation assay").

The activation assay measures the stimulation of the production of cyclic adenosinemonophosphate (cAMP) in the HTRF assay, with the maximum increase in cAMP by increasing concentrations of the endogenous agonist, dopamine, defined as 100% activation. When tested compounds of the Examples lack significant direct agonist-like effects in that they produce less than 20% of activation (compared to dopamine maximal response) when present in a concentration of 10 μM.

The potentiation assay measures the ability of compounds to increase the levels of cAMP produced by a low-threshold concentration of dopamine. The concentration of dopamine used ([EC$_{20}$]) is designed to produce 20% stimulation compared to the maximal response (100%) seen with increasing the concentration of dopamine. To measure this potentiation we incubate increasing concentrations of the compound with the [EC$_{20}$] of dopamine and measure the potentiation as increases in cAMP production. The pEC$_{50}$ of a compound is the −log 10 of the concentration of the compound which produces 50% of the potentiation of the cAMP levels and the Erel is the relative efficacy, defined as the maximal % potentiation produced by the compound compared to the maximal response produced by increasing concentrations of dopamine (Erel of 1=dopamine maximum response).

The particular conditions in which the compounds have been tested are described here below.

Methods D1 Cell Culture

Cells were cultured at 37° C. in a humidified atmosphere of 5% CO$_2$. Cells were grown in DMEM-F12+GlutaMAX™-I medium (GIBCO®, Invitrogen, Merelbeke, Belgium) containing 10% fetal bovine serum (BioWhittaker®, Lonza, Verviers, Belgium), 400 μg/mL Geneticin (GIBCO®), 100 IU/mL Penicillin and 100 IU/mL Streptomycin (Pen-Strep solution, BioWhittaker®). LMtk (Ltk−) mouse fibroblast cells expressing the dopamine D1 receptor (BioSignal Inc, Montreal, Canada, now Perkin Elmer) were used as they have been shown to couple efficiently and give robust functional responses (Watts et al, 1995).

cAMP Assay

The measurement of changes in intracellular cyclic adenosinemonophosphate (cAMP) was determined using the HTRF cAMP dynamic assay kit from CisBio (Codolet, France). Using homogenous time-resolved fluoresence technology, the assay is based on competition between native cAMP produced by cells and cAMP labelled with the dye d2. The tracer binding is determined by an anti-cAMP antibody labeled with cryptate. The effects of the compound alone (agonism) was determined by performing the assay in the absence of dopamine, whilst the effect of the compound as a positive allosteric modulator (PAM) was determined in the presence of an EC$_{20}$ concentration of dopamine. Cells (20, 000 per well) are incubated in 384 plates for 1 hour at room temperature in a final volume of 20 μL HBSS (Lonza, with calcium, magnesium and HEPES buffer 20 mM, pH 7.4)

containing: isobutyl methylxanthine (Sigma, 0.1 mM final), varying concentrations of test compound (typically $10^{-9.5}$M to $10^{-4.5}$M) in the presence and absence of dopamine (1.1 nM final). The reaction is then terminated and the cells lysed by adding the d2 detection reagent in lysis buffer (10 μL) and the cryptate reagent in lysis buffer (10 μL) according to manufacturer's instructions. This is then incubated for a further 60 min. at room temperature and changes in HTRF fluorescent emission ratio determined according to manufacturer's instructions using an Envision plate reader (Perkin Elmer, Zaventem, Belgium) with laser excitation. All incubations were performed in duplicate and results were compared to a concentration-effect curve to dopamine. ($10^{-11}$M to $10^{-6}$M).

Data Analysis

Data was analyzed using Excel and PRISM (GraphPad Software) to obtain $pEC_{50}$ and Erel using the 4-parameter logistic equation (DeLean et al, 1978) where Erel is the fitted maximal response of the test compound minus basal expressed as a percentage relative to that obtained with dopamine which was defined as 100%.

When tested in the cAMP HTRF assay, compounds of the Examples exhibit values of $pEC_{50}$ greater than or equal to 5.5; ideally greater than or equal to 6.5; preferably greater than or equal to 7.0.

The invention claimed is:

1. A compound of formula (I), or a pharmaceutically acceptable salt thereof;

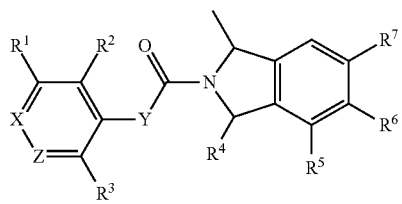

(I)

wherein

R$^1$ is hydrogen, halogen, cyano or hydroxy; $C_{1-6}$ alkyl, $C_{1-6}$ alkoxy, $C_{1-6}$ alkylsulfanyl, $C_{1-6}$ alkylsulfinyl, $C_{1-6}$ alkylsulfonyl, ($C_{1-6}$-alkylsulfonyl)amino or ($C_{1-6}$-alkylsulfonyl)amino($C_{1-6}$alkyl), any of which groups is optionally substituted by one or more substituents;

R$^2$ is hydrogen, cyano, halogen; or $C_{1-6}$ alkyl, $C_{1-6}$ alkoxy, $C_{1-6}$ alkylsulfanyl, $C_{1-6}$ alkylsulfinyl, $C_{1-6}$ alkylsulfonyl, $C_{1-6}$ alkylsulfonylamino, ($C_{1-6}$ alkylsulfonyl)amino($C_{1-6}$ alkyl), $C_{1-6}$ alkylamido, ($C_{1-6}$ alkylacyl)amino, ($C_{1-6}$ alkylacyl)amino($C_{1-6}$ alkyl), or heteroaryl, any of which groups is optionally substituted by one or more substituents; or R$^1$ and R$^2$ are linked together to form with the adjacent aromatic group a bicycle of formula (i):

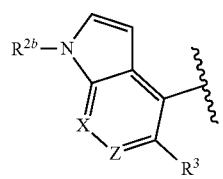

(i)

wherein R$^{2b}$ is hydrogen or $C_{1-6}$ alkylsulfonyl;

R$^3$ is halogen, $C_{1-6}$ alkyl, $C_{1-6}$ alkoxy or cyano;

R$^4$ is hydrogen, halogen, $C_{1-6}$ alkyl, hydroxy, $C_{1-6}$ alkoxy, $C_{1-6}$ alkylsulfonyl, $C_{1-6}$ alkoxycarbonyloxy or $C_{1-6}$ alkylaminocarbonyloxy;

R$^5$ is hydrogen, cyano, hydroxy or nitro; or $C_{1-6}$ alkyl; or $C_{1-6}$ alkoxy, $C_{1-6}$-alkylsulfonyl, $C_{1-6}$-alkylsulfonylamino; $C_{1-6}$-alkylsulfonylamino($C_{1-6}$ alkyl), heterocycle, $C_{1-6}$ alkylacylamino, $C_{1-6}$ alkylacylamino($C_{1-6}$ alkyl); $C_{1-6}$ alkylureido($C_{1-6}$ alkyl); $C_{1-6}$alkylcarbamate($C_{1-6}$ alkyl); amido; $C_{1-6}$alkoxycarbonyl, $C_{1-6}$alkoxycarbonyloxy($C_{1-6}$alkyl); amino group; N-cyano-S—($C_{1-6}$-alkyl)sulfonimidoyl, N,S-(di-$C_{1-6}$-alkyl)sulfonimidoyl, aminosulfinyl; $C_{1-6}$-alkylsulfinyl; aminosulfonyl; (di-$C_{1-6}$-alkyl)(oxido)-$\lambda^6$-sulfanylidene-amino; amino($C_{1-6}$ alkyl), amido($C_{1-6}$ alkyl) or amido($C_{1-6}$ alkoxy); any of which groups is optionally substituted by one or more substituents;

R$^6$ is hydrogen or cyano;

R$^7$ is either hydrogen or ($C_{1-6}$-alkylsulfonyl)amino;

X is either CR$^9$ or N; wherein R$^9$ is hydrogen, halogen or $C_{1-6}$-alkyl substituted by hydroxy;

Z is CH or N; and

Y is $CH_2$ or NH.

2. The compound according to claim 1 represented by formula I-A, or a pharmaceutically acceptable salt thereof,

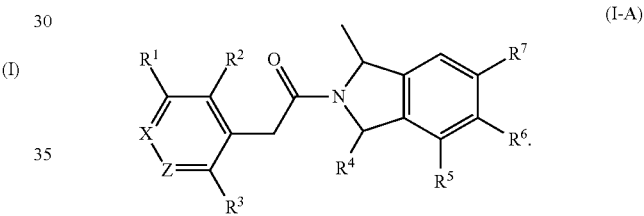

(I-A)

3. The compound according to claim 1 represented by formula I-B, or a pharmaceutically acceptable salt thereof,

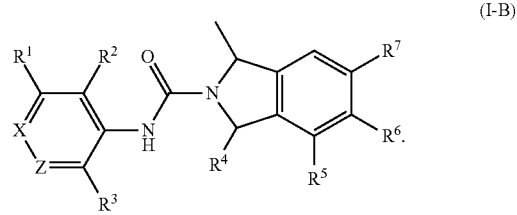

(I-B)

4. The compound according to claim 1 or a pharmaceutically acceptable salt thereof, wherein R$^1$ is hydrogen, halogen, or hydroxy; or $C_{1-6}$ alkyl, $C_{1-6}$ alkoxy or ($C_{1-6}$-alkylsulfonyl)amino($C_{1-6}$alkyl), any of which groups is optionally substituted by one or more substituents.

5. The compound according to claim 1 or a pharmaceutically acceptable salt thereof, wherein R$^1$ is hydrogen.

6. The compound according to claim 1 or a pharmaceutically acceptable salt thereof, wherein R$^2$ is cyano or halogen; or $C_{1-6}$ alkyl, which group is optionally substituted by one or more substituents.

7. The compound according to claim 1 or a pharmaceutically acceptable salt thereof, wherein R$^4$ is hydrogen.

8. The compound according to claim 1 or a pharmaceutically acceptable salt thereof wherein R$^6$ is hydrogen.

9. The compound according to claim 1 or a pharmaceutically acceptable salt thereof wherein $R^7$ is hydrogen.

10. The compound according to claim 1 or a pharmaceutically acceptable salt thereof wherein X is CH.

11. The compound according to claim 1 or a pharmaceutically acceptable salt thereof wherein Z is CH.

12. The compound as claimed in claim 2 represented by formula (I-A-A) or a pharmaceutically acceptable salt thereof;

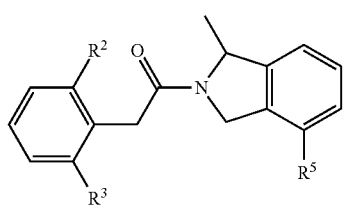

(I-A-A)

wherein $R^2$, $R^3$ and $R^5$ are as defined in claim 1.

13. The compound according to claim 1 or a pharmaceutically acceptable salt thereof wherein $R^2$ is halogen or cyano.

14. The compound according to claim 1 or a pharmaceutically acceptable salt thereof wherein $R^3$ is halogen or cyano.

15. The compound according to claim 1 or a pharmaceutically acceptable salt thereof wherein $R^2$ is chloro or cyano.

16. The compound according to claim 1 or a pharmaceutically acceptable salt thereof wherein $R^3$ is chloro or cyano.

17. The compound according to claim 1 or a pharmaceutically acceptable salt thereof wherein
$R^5$ is hydrogen, hydroxy or nitro; or $C_{1-6}$ alkyl; $C_{1-6}$ alkoxy, $C_{1-6}$-alkylsulfonyl, $C_{1-6}$-alkylsulfonylamino; $C_{1-6}$-alkylsulfonylamino($C_{1-6}$ alkyl), heterocycle, $C_{1-6}$ alkylacylamino; amido; $C_{1-6}$alkoxycarbonyl, amino group; aminosulfonyl; (di-$C_{1-6}$-alkyl)(oxido)-$\lambda^6$-sulfanylidene-amino or amido($C_{1-6}$ alkoxy); any of which groups is optionally substituted by one or more substituents.

18. The compound according to claim 1 or a pharmaceutically acceptable salt thereof wherein
$R^5$ is hydrogen, hydroxy, nitro; (trifluoro)(hydroxyl)ethyl, (hydroxy)methyl, methoxy, methylsulfonyl, methylsulfonylamino, methylsulfonylaminomethyl, pyrazolyl, methylcarbonylamino, carbamoyl, methoxycarbonyl, amino, methylaminosulfonyl, isopropylaminosulfonyl, ethylaminosulfonyl, (trifluromethyl)methylaminosufonyl, triazolylaminosulfonyl, (methy)pyrazolylaminosulfonyl, (tetrahydropyranyl)methylsulfonyl, pyrrolidinylaminosulfonyl, piperidinylaminosulfonyl, azetidinylaminosulfonyl, (di-methyl)(oxido)-$\lambda^6$-sulfanylidene-amino, methylaminocarbonylmethoxy, or dimethylaminocarbonylmethoxy.

19. The compound according to claim 1, selected from the group consisting of
2-(2,6-dichlorophenyl)-1-(1-methyl-1,3-dihydro-2H-isoindol-2-yl)ethanone;
2-(2,6-dichlorophenyl)-1-[(1S)-1-methyl-1,3-dihydro-2H-isoindol-2-yl]ethanone;
2-(2,6-dichlorophenyl)-1-[(1R)-1-methyl-1,3-dihydro-2H-isoindol-2-yl]ethanone;
2-(2-chloro-6-iodophenyl)-1-(1-methyl-1,3-dihydro-2H-isoindol-2-yl)ethanone;
2-(2,4-dichloropyridin-3-yl)-1-(1-methyl-1,3-dihydro-2H-isoindol-2-yl)ethanone;
2-(2,6-dichlorophenyl)-1-(1-methyl-4-nitro-1,3-dihydro-2H-isoindol-2-yl)ethanone;
3-chloro-2-{2-[(1S)-1-methyl-1,3-dihydro-2H-isoindol-2-yl]-2-oxoethyl}benzonitrile;
2-(3,5-dichloro-2-methylpyridin-4-yl)-1-[(1S)-1-methyl-1,3-dihydro-2H-isoindol-2-yl]ethanone;
2-(3-bromo-5-chloropyridin-4-yl)-1-[(1S)-1-methyl-1,3-dihydro-2H-isoindol-2-yl]ethanone;
2-(5-chloro-1H-pyrrolo[2,3-b]pyridin-4-yl)-1-[(1S)-1-methyl-1,3-dihydro-2H-isoindol-2-yl]ethanone;
2-(3,5-dichloro-2-methoxypyridin-4-yl)-1-[(1S)-1-methyl-1,3-dihydro-2H-isoindol-2-yl]ethanone;
2-(3,5-dichloropyridin-4-yl)-1-[(1S)-1-methyl-1,3-dihydro-2H-isoindol-2-yl]ethanone;
N-{(1S)-2-[(2,6-dichlorophenyl)acetyl]-1-methyl-2,3-dihydro-1H-isoindol-4-yl}methanesulfonamide;
1-[(1S)-4-amino-1-methyl-1,3-dihydro-2H-isoindol-2-yl]-2-(2,6-dichlorophenyl)ethanone;
methyl 2-[(2,6-dichlorophenyl)acetyl]-1-methyl-2,3-dihydro-1H-isoindole-4-carboxylate;
2-[2,6-dichloro-3-(hydroxymethyl)phenyl]-1-(1-methyl-1,3-dihydro-2H-isoindol-2-yl)ethanone;
2-[2,6-dichloro-3-(hydroxymethyl)phenyl]-1-[(1S)-1-methyl-1,3-dihydro-2H-isoindol-2-yl]ethanone;
2-(2,6-dichlorophenyl)-1-(4-hydroxy-1-methyl-1,3-dihydro-2H-isoindol-2-yl)ethanone;
2-[(2,6-dichlorophenyl)acetyl]-1-methyl-2, 3-dihydro-1H-isoindole-4-carboxamide;
N-{2-[(2,6-dichlorophenyl)acetyl]-1-methyl-2, 3-dihydro-1H-isoindol-4-yl}acetamide;
2-({2-[(2,6-dichlorophenyl)acetyl]-1-methyl-2,3-dihydro-1H-isoindol-4-yl}oxy)-N-methylacetamide;
2-({2-[(2,6-dichlorophenyl)acetyl]-1-methyl-2,3-dihydro-1H-isoindol-4-yl}oxy)-N,N-dimethylacetamide;
2-(2,6-dichlorophenyl)-1-(4-methoxy-1-methyl-1,3-dihydro-2H-isoindol-2-yl)ethanone;
(1S)-2-[(2,6-dichlorophenyl)acetyl]-N, 1-dimethyl-2,3-dihydro-1H-isoindole-4-sulfonamide;
2-[(2,6-dichlorophenyl)acetyl]-1-methyl-2, 3-dihydro-1H-isoindole-5-carbonitrile2-[2-chloro-6-(hydroxymethyl)phenyl]-1-[(1S)-1-methyl-1,3-dihydro-2H-isoindol-2-yl]ethanone;
2-(2,6-dichlorophenyl)-1-[(1R)-4-(hydroxymethyl)-1-methyl-1,3-dihydro-2H-isoindol-2-yl]ethanone;
2-(2,6-dichlorophenyl)-1-[(1S)-4-(hydroxymethyl)-1-methyl-1,3-dihydro-2H-isoindol-2-yl]ethanone;
3,5-dichloro-4-{2-[(1S)-1-methyl-1,3-dihydro-2H-isoindol-2-yl]-2-oxoethyl}pyridin-2(1H)-one;
2-(2,6-dichlorophenyl)-1-[1-methyl-4-(methylsulfonyl)-1,3-dihydro-2H-isoindol-2-yl]ethanone;
2-(2,6-dichlorophenyl)-1-[(1S)-1-methyl-4-(pyrrolidin-1-ylsulfonyl)-1,3-dihydro-2H-isoindol-2-yl]ethanone;
2-(2,6-dichlorophenyl)-1-[(1S)-1-methyl-4-(piperidin-1-ylsulfonyl)-1,3-dihydro-2H-isoindol-2-yl]ethanone;
1-[(1S)-4-(azetidin-1-ylsulfonyl)-1-methyl-1,3-dihydro-2H-isoindol-2-yl]-2-(2,6-dichlorophenyl)ethanone;
(1S)-2-[(2,6-dichlorophenyl)acetyl]-1-methyl-N-(propan-2-yl)-2, 3-dihydro-1H-isoindole-4-sulfonamide;
(1S)-2-[(2,6-dichlorophenyl)acetyl]-N-ethyl-1-methyl-2, 3-dihydro-1H-isoindole-4-sulfonamide;
(1S)-2-[(2,6-dichlorophenyl)acetyl]-1-methyl-N-(2,2,2-trifluoroethyl)-2, 3-dihydro-1H-isoindole-4-sulfonamide;

(1S)-2-[(2,6-dichlorophenyl)acetyl]-1-methyl-N-(1-methyl-1H-pyrazol-3-yl)-2,3-dihydro-1H-isoindole-4-sulfonamide;

(1S)-2-[(2,6-dichlorophenyl)acetyl]-1-methyl-N-(4H-1,2,4-triazol-3-yl)-2,3-dihydro-1H-isoindole-4-sulfonamide;

(1S)-2-[(2,6-dichlorophenyl)acetyl]-1-methyl-N-(1-methyl-1H-pyrazol-5-yl)-2,3-dihydro-1H-isoindole-4-sulfonamide;

N-({2-[(2,6-dichlorophenyl)acetyl]-1-methyl-2,3-dihydro-1H-isoindol-4-yl}methyl)methanesulfonamide;

N-(2,4-dichloro-3-{2-[(1S)-1-methyl-1,3-dihydro-2H-isoindol-2-yl]-2-oxoethyl}benzyl)methanesulfonamide;

2-(2,6-dichlorophenyl)-1-{(1S)-1-methyl-4-[(tetrahydro-2H-pyran-4-ylmethyl)sulfonyl]-1,3-dihydro-2H-isoindol-2-yl}ethanone;

(1S)—N-(2,6-dichlorophenyl)-1-methyl-1,3-dihydro-2H-isoindole-2-carboxamide;

(1S)—N-(2-chloro-6-methylphenyl)-1-methyl-1,3-dihydro-2H-isoindole-2-carboxamide;

2-(2,6-dichlorophenyl)-1-[(1S)-4-{[dimethyl(oxido)-$\lambda^6$-sulfanylidene]amino}-1-methyl-1,3-dihydro-2H-isoindol-2-yl]ethanone;

2-(2,6-dichlorophenyl)-1-[(1S)-1-methyl-4-(1H-pyrazol-4-yl)-1,3-dihydro-2H-isoindol-2-yl]ethanone;

2-(5-chloro-1H-indol-4-yl)-1-[(1S)-1-methyl-1,3-dihydro-2H-isoindol-2-yl]ethanone; and 3-chloro-2-(2-{(1S)-1-methyl-4-[2,2,2-trifluoro-1-hydroxyethyl]-1,3-dihydro-2H-isoindol-2-yl}-2-oxoethyl)benzonitrile.

20. A method of making a pharmaceutical composition comprising a compound according to claim 1 or a pharmaceutically acceptable salt thereof, the method comprising mixing the compound with a pharmaceutically acceptable carrier.

* * * * *